(12) United States Patent
Agresti et al.

(10) Patent No.: US 11,923,045 B2
(45) Date of Patent: Mar. 5, 2024

(54) MULTIPARAMETRIC DISCOVERY AND OPTIMIZATION PLATFORM

(71) Applicant: TripleBar Bio, Inc., Emeryville, CA (US)

(72) Inventors: Jeremy Agresti, Richmond, CA (US); Andres Ornelas Vargas, San Francisco, CA (US); Kevin Gregory Hoff, Emeryville, CA (US)

(73) Assignee: TRIPLEBAR BIO, INC., Emeryville, CA (US)

( * ) Notice: Subject to any disclaimer, the term of this patent is extended or adjusted under 35 U.S.C. 154(b) by 0 days.

(21) Appl. No.: 18/085,269

(22) Filed: Dec. 20, 2022

(65) Prior Publication Data

US 2023/0154562 A1    May 18, 2023

Related U.S. Application Data

(63) Continuation of application No. PCT/US2021/059275, filed on Nov. 13, 2021.
(Continued)

(51) Int. Cl.
*G01N 33/48* (2006.01)
*C12N 15/10* (2006.01)
(Continued)

(52) U.S. Cl.
CPC ......... *G16B 20/00* (2019.02); *C12N 15/1037* (2013.01); *C12N 15/1058* (2013.01);
(Continued)

(58) Field of Classification Search
CPC ........ G16B 20/00; G16B 20/50; G16B 35/10; G16B 40/00; G16B 99/00; C12N 15/1058; C12N 15/1089
See application file for complete search history.

(56) References Cited

U.S. PATENT DOCUMENTS 10,527,529 B2    1/2020   Miller et al.
10,710,078 B2    7/2020   Merten et al.
(Continued)

FOREIGN PATENT DOCUMENTS

WO    WO-2016174229 A1    11/2016
WO    WO-2017100377 A1    6/2017
(Continued)

OTHER PUBLICATIONS

Agresti et al. Ultrahigh-throughput screening in drop-based microfluidics for directed evolution. PNAS 107(9):4004-4009 (Mar. 2, 2010).
Corrections and Editorial Expression of Concern, PNAS 107(14):6550-6551 (Apr. 6, 2010).
(Continued)

*Primary Examiner* — Russell S Negin
(74) *Attorney, Agent, or Firm* — Wilson Sonsini Goodrich & Rosati

(57) ABSTRACT

Provided herein are systems and methods for screening desirable biological variants using a high-throughput integrated system. The integrated system may be configured to input a plurality of parameters from functional studies of biological variants under applied conditions, in conjunction with integrated libraries of biological variants, and filter the inputs to produce desirable biological variants based on an input performance requirement. The system may output optimized strains, molecules, or novel molecules expected to have a desirable functional characteristic. Accordingly, the (Continued)

methods and systems disclosed herein enable multi-parametric studies of biological diversity and conditional diversity in systems biology.

29 Claims, 18 Drawing Sheets

Related U.S. Application Data

(60) Provisional application No. 63/113,571, filed on Nov. 13, 2020.

(51) Int. Cl.
| | | |
|---|---|---|
| G01N 33/50 | (2006.01) | |
| G16B 20/00 | (2019.01) | |
| G16B 20/50 | (2019.01) | |
| G16B 35/10 | (2019.01) | |
| G16B 40/00 | (2019.01) | |
| G16B 99/00 | (2019.01) | |

(52) U.S. Cl.
CPC ......... *C12N 15/1089* (2013.01); *G16B 20/50* (2019.02); *G16B 35/10* (2019.02); *G16B 40/00* (2019.02); *G16B 99/00* (2019.02)

(56) References Cited

U.S. PATENT DOCUMENTS

| | | | |
|---|---|---|---|
| 10,960,398 | B2 | 3/2021 | Fobel et al. |
| 2009/0130718 | A1 | 5/2009 | Short |
| 2010/0100331 | A1 | 4/2010 | Gustafsson et al. |
| 2014/0256557 | A1 | 9/2014 | Fox |
| 2016/0210403 | A1 | 7/2016 | Zhang et al. |
| 2019/0315815 | A1* | 10/2019 | Hittinger ............... C12N 1/16 |
| 2019/0345566 | A1* | 11/2019 | Khera ................... G16H 50/20 |

FOREIGN PATENT DOCUMENTS

| | | | |
|---|---|---|---|
| WO | WO-2019006022 A1 | 1/2019 | |
| WO | WO-2019178427 A1 * | 9/2019 | ........... C12N 15/102 |
| WO | WO-2021050923 A1 | 3/2021 | |
| WO | WO-2022104164 A1 | 5/2022 | |

OTHER PUBLICATIONS

Aharoni, et al. High-throughput screening of enzyme libraries: thiolactonases evolved by fluorescence-activated sorting of single cells in emulsion compartments. Chem Biol. Dec. 2005;12(12):1281-9.
Beneyton et al. CotA laccase: high-throughput manipulation and analysis of recombinant enzyme libraries expressed in *E. coli* using droplet-based microfluidics. Analyst, 2014, 139, 3314. 10 pages.
Christen et al. Design, Fabrication, and Testing of a Hybrid CMOS/PDMS Microsystem for Cell Culture and Incubation. IEEE Transactions on Biomedical Circuits and Systems, vol. 1, No. 1, pp. 3-18, (Mar. 2007).
Colin et al. Enzyme engineering in biomimetic compartments. Current Opinion in Structural Biology, vol. 33, pp. 42-51 (Aug. 2015). Retrieved Jan. 5, 2023 at URL: https://core.ac.uk/download/pdf/77408761.pdf.
Co-pending U.S. Appl. No. 18/084,975, inventors Agresti; Jeremy et al., filed Dec. 20, 2022.
DFC, "self-learning" flow rate control algorithm. Web page. Fluigent. Retrieved Jun. 3, 2022 at URL: https://www.fluigent.com/resources-support/expertise/expertise-reviews/advantages-of-pressure-based-microfluidics/dfc-self-learning-flow-rate-control-algorithm/. 6 pages.
Dove. Screening for content-the evolution of high throughput. Nature Biotechnology, vol. 21, No. 8, pp. 859-864 (Aug. 2003).
Duarte et al. Bacterial Microcolonies in Gel Beads for High-Throughput Screening of Libraries in Synthetic Biology. ACS Synth. Biol. 2017, 6, 11, 1988-1995. Retrieved Jan. 5, 2023 at URL: https://core.ac.uk/download/pdf/145239190.pdf.
Eduati et al. A microfluidics platform for combinatorial drug screening on cancer biopsies. Nature Communications (2018) 9:2434. 13 pages.
Extebarria et al. Highly integrated polymeric microliquid flow controller for droplet microfluidics. Microfluid Nanofluid (2017) 21:63. 10 pages.
Gielen et al. Ultrahigh-throughput-directed enzyme evolution by absorbance-activated droplet sorting (AADS). PNAS, E7383-E7389. Published online Nov. 7, 2016.
Godina. In vivo and in vitro directed evolution of enzymes using droplet-based microfluidics. Thesis. HAL Open Science. HAL ID: tel-01124086. Université de Strasbourg, 2013. English. NNT: 2013STRAF061. Retrieved Jan. 17, 2023 at URL: https://tel.archives-ouvertes.fr/tel-01124086/document. 188 pages.
Gong et al. All-Electronic Droplet Generation On-Chip with Real-Time Feedback Control for EWOD Digital Microfluids. Lab Chip. Jun. 2008 ; 8(6): 898-906.
Kim et al. Modulation of fluidic resistance and capacitance for long-term, high-speed feedback control of a microfluidic interface. Lab Chip, 2009, 9, 2603-2609.
Kintses et al. Picoliter Cell Lysate Assays in Microfluidic Droplet Compartments for Directed Enzyme Evolution. Chemistry & Biology, vol. 19, Issue 8, pp. 1001-1009 (Aug. 24, 2012).
Lou et al. A High-Throughput Photodynamic Therapy Screening Platform with On-Chip Control of Multiple Microenvironmental Factors. Lab Chip. Mar. 7, 2014; 14(5): 892-901.
Mehmood et al. Droplet movement control using fuzzy logic controller and image processing along with pin valves inside microfluidic device. Measurement and Control 2019, vol. 52(9-10) 1517-1531.
Miller et al. Microfluidic device incorporating closed loop feedback control for uniform and tunable production of micro-droplets. Lab Chip, 2010, 10, 1293-1301.
Motaghi et al. Control of Droplet Size in a Two-Phase Microchannel using PID Controller: A Novel Experimental Study (2020). Abstract only. Retrieved Jun. 3, 2020 at URL: https://www.semanticscholar.org/paper/Control-of-Droplet-Size-in-a-Two-Phase-Microchannel-Motaghi-Nazari/edd69be13bdba71aac0d0680df9bb4a988ef3b3c. 5 pages.
PCT/US2021/059275 International Search Report and Written Opinion dated Mar. 16, 2022.
Prieto et al. Real-Time Monitoring and Feedback Control of Droplet Generation. Thirteenth International Conference on Miniaturized Systems for Chemistry and Life Sciences, Nov. 1-5, 2009, Jeju, Korea, pp. 1431-1433. Retrieved Jun. 3, 2022 at URL: https://www.rsc.org/binaries/LOC/2009/Pdf/468-W18A.pdf.
Prodanovic et al. Vanadium bromoperoxidase-coupled fluorescent assay for flow cytometry sorting of glucose oxidase gene libraries in double emulsions. Anal Bioanal Chem 404, 1439-1447 (2012). Published online Jul. 19, 2012.
Shin et al. Protein design and variant prediction using autoregressive generative models. Nature Communications (2021) 12:2403. 11 pages.
Taly et al., Droplets as Microreactors for High-Throughput Biology, Chembiochem 8(3):263-272 (2007).
Torres et al. Nanowell-Based Immunoassays for Measuring Single-Cell Secretion: Characterization of Transport and Surface Binding. Anal. Chem. 2014, 86, 11562-11569.
Wu et al. Machine learning-assisted directed protein evolution with combinatorial libraries. PNAS, vol. 116, No. 18, pp. 8852-8858 (Apr. 30, 2019). Published online Apr. 12, 2019. With Correction, PNAS, vol. 117, No. 1, pp. 788-789 (Jan. 7, 2020). First published Dec. 30, 2019.
Wu et al. Protein sequence design with deep generative models. Current Opinion in Chemical Biology, vol. 65, pp. 18-27 (2021).
Xu et al. Deep Dive into Machine Learning Models for Protein Engineering. J. Chem. Inf. Model. 2020, 60, 2773-2790.
Yang et al. Ultrahigh-Throughput FACS-Based Screening for Directed Enzyme Evolution. ChemBioChem, vol. 10. Issue 17, pp. 2704-2715 (Nov. 23, 2009). First published Nov. 17, 2009.

(56) References Cited

OTHER PUBLICATIONS

Zeng et al. Closed-loop feedback control of droplet formation in a T-junction microdroplet generator. Sensors and Actuators A 233 (2015) 542-547. Available online Aug. 12, 2015.
Huang et al. Microfluidic screening and whole-genome sequencing identifies mutations associated with improved protein secretion by yeast. PNAS, pp. E4689-E4696, published online Aug. 10, 2015.
U.S. Appl. No. 18/084,975 Office Action dated Aug. 31, 2023.
U.S. Appl. No. 18/084,975 Notice of Allowance dated Jan. 11, 2024.

* cited by examiner

| Original hit strain | Mutations | Improvement in original O3297 nucB host | Improvement in O402 nucB shuffling isolates | Improvement in GFP-expr O707 host |
|---|---|---|---|---|
| 03549 | sigA T31R, M39L, L56F, R210P, P237S, D275E | 4.0 | | 2.5 |
| 03553 | sigA V102D, R207S, I242F, A287S | 2.9 | | 3.7 |
| 03565 | sigA A2S, L30S, M158I, I209F, D305Y, L318M, A351V | 4.3 | | 2.4 |
| 03606 | sigA K4I, S23Y, K25N, Q48R, I109T, A122T, A197T, R210Q, T238S, G279S, F339L | 4.2 | 1.6 | 3.7 |

FIG. 12

MULTIPARAMETRIC DISCOVERY AND OPTIMIZATION PLATFORM

CROSS REFERENCE

This application is a continuation of International Application No. PCT/US2021/059275, filed Nov. 13, 2021, which claims the benefit of U.S. Provisional Application No. 63/113,571, filed on Nov. 13, 2020, both of which are incorporated herein by reference in their entirety for all purposes.

BACKGROUND

Directed evolution is a useful tool in screening a library of species and selecting for a desired functionality in an iterative process. Such processes allow for screening of large numbers of molecules or strains (e.g., gene variants) for a functional characteristic and enables engineering of molecules (e.g., proteins) toward a functional goal.

However, current processes for molecular and/or strain discovery and optimization suffer from limited throughput and/or do not exploit multiple data inputs from a variety of sources to predict an outcome or drive the directed evolution process. Furthermore, high cost and long times associated with traditional high throughput screening technologies typically limit the diversity of conditions under which product can be optimized. Consequently, molecular and/or strain discovery and optimization can be slow, costly and non-optimal. Lack of integrated multiparametric, data-driven processes may further prevent discovery of molecules or strains or fail to uncover molecules or strains that require multiple inputs for discovery.

SUMMARY

Recognized herein is a need for modular, high-throughput platforms for molecule discovery, molecule optimization, and optimization of species or strains (e.g., using induced mutations, directed evolution, etc.). The present disclosure addresses the above-identified needs by providing systems and methods for combining and using large data inputs (including open and publicly sourced data), empirical data, and known conditions into a simultaneous machine learning platform for driving molecular discovery, optimization, and functional predictions of molecules (e.g., biomolecules such as proteins).

In an aspect, provided herein is a method for generating an improved polymer variant, the method comprising (a) obtaining a dataset comprising (i) sequence data comprising data on polymer variant sequences; and (ii) enrichment data based on an abundance of the polymer variant sequences in a sample sorted based on the polymer variant function; and (b) applying one or more machine learning algorithms to the dataset to design an improved polymer variant.

In some embodiments, the polymer variant sequences comprise sequences i) in an unsorted sample and ii) in the sample sorted based on the polymer variant function, wherein the sample sorted based on the polymer variant function and the unsorted sample are from a common sample.

In some embodiments, the enrichment data are further based on an abundance of the polymer variant sequences in the unsorted sample. In some embodiments, the abundance of the polymer variant sequences in the sample sorted based on the polymer variant function comprises a sequence count. In some embodiments, the abundance of the polymer variant sequences in the unsorted sample comprises a sequence count. In some embodiments, the enrichment data comprise an enrichment factor for a first polymer variant sequence based on i) an abundance of the first polymer variant sequence in the polymer variant sequences in the unsorted sample and ii) an abundance of the first polymer variant sequence in the polymer variant sequences in the subset of the sample sorted based on the polymer variant function. In some embodiments, the enrichment factor is a functional label for the first polymer variant sequence. In some embodiments, the method comprises performing multiple generations of (a) and (b), wherein the improved polymer variant of (b) is used to generate the dataset of (a) in a subsequent generation of the multiple generations. In some embodiments, the multiple generations are at least 3 or 4 generations.

In some embodiments, the polymer variant comprises a protein. In some embodiments, the protein comprises an enzyme. In some embodiments, the function comprises an activity of the enzyme. In some embodiments, the improved polymer variant comprises at least 1000 improved polymer variants. In some embodiments, the polymer variant sequences comprise nucleic acid sequences encoding the polymer variant.

In some embodiments, the method further comprises, before obtaining the dataset, providing a library of cells comprising the polymer variant, wherein the polymer variant comprises polymer variants. In some embodiments, the method further comprises generating the library of cells comprising the polymer variants. In some embodiments, the generating comprises providing a site saturation nucleic acid molecule library (SSL) encoding proteins with each of 20 naturally-occurring amino acids at each position. In some embodiments, the method further comprises performing gene shuffling and error-prone polymerase chain reaction (epPCR) on the SSL to generate nucleic acid molecules encoding the polymer variants. In some embodiments, the method further comprises transforming the nucleic acid molecules encoding the polymer variants into cells to generate the library of cells. In some embodiments, the cells comprise bacterial cells. In some embodiments, the method further comprises partitioning the library of cells to generate a plurality of partitions. In some embodiments, each partition of the plurality of partitions comprises on average one or fewer cells. In some embodiments, the method further comprises growing the library of cells in the plurality of partitions. In some embodiments, the method further comprises expressing the polymer variants in the library of cells in the plurality of partitions. In some embodiments, the method further comprises determining the polymer variant function using the library of cells comprising the polymer variants. In some embodiments, the polymer variants comprise proteins. In some embodiments, the proteins comprise enzymes. In some embodiments, the determining the polymer variant function comprises using an enzyme substrate and a reaction buffer. In some embodiments, the polymer variant function comprises enzyme activity. In some embodiments, the enzyme activity produces a fluorescent product.

In some embodiments, the method further comprises sorting a subset of the library of cells comprising the polymer variants based on the polymer variant function to provide the sample sorted based on the polymer variant function and an unsorted sample. In some embodiments, the function is an amount of enzyme activity. In some embodiments, the sorting comprises sorting the subset of the library of cells into a plurality of groups based on the function. In some embodiments, the plurality of groups is at least 4 groups. In some embodiments, the subset of the library of cells comprises from about 50 times to about 100 times a number of unique polymer variants expected to exist in the library of cells. In some embodiments, the method further comprises using the sample sorted based on the polymer variant function to determine the polymer variant sequences. In some embodiments, the sample sorted based on the polymer variant function comprises a fiducial sequence. In some embodiments, using the sample sorted based on the polymer variant function to determine the polymer variant sequences comprises purifying nucleic acid molecules from the sample sorted based on the polymer variant function. In some embodiments, the method further comprises purifying nucleic acid molecules from the unsorted sample. In some embodiments, the purifying nucleic acid molecules from the sample sorted based on the polymer variant function occurs separately from the purifying nucleic acid molecules from the unsorted sample. In some embodiments, the method further comprises sequencing the nucleic acid molecules from the sample sorted based on the polymer variant function and the nucleic acid molecules from the unsorted sample to provide the polymer variant sequences. In some embodiments, the sequencing comprises next generation sequencing. In some embodiments, the method further comprises using the polymer variant sequences to determine the abundance of the polymer variant sequences i) in the sample sorted based on the polymer variant function and ii) in the unsorted sample. In some embodiments, the method further comprises using the abundance of the polymer variant sequences i) in the sample sorted based on the polymer variant function and ii) in the unsorted sample to determine the enrichment data. In some embodiments, the enrichment data comprises an enrichment factor In some embodiments, the method further comprises synthesizing the improved polymer variant. In some embodiments, the synthesizing comprises synthesis on an oligonucleotide array. In some embodiments, the method further comprises assembling the improved polymer variant into a vector. In some embodiments, the vector is a plasmid. In some embodiments, the method further comprises introducing the vector into a host cell.

In some embodiments, (a) of a first generation of the multiple generations comprises performing saturation mutagenesis and epPCR to provide a library of cells; wherein (a) of a second generation of the multiple generations comprises performing epPCR; and wherein (a) of a third generation of the multiple generations comprises performing epPCR. In some embodiments, each generation of the multiple generations comprises multiple rounds of the sorting of.

In another aspect, provided herein is a non-transitory computer readable medium comprising instructions thereon which when executed by a computer processor cause the computer processor to perform the method of any embodiment described herein.

In another aspect, disclosed herein is a system comprising a computer processor and the non transitory computer readable medium.

In yet another aspect, disclosed herein is a system for processing cells comprising one or more processors and computer readable medium, the computer readable medium comprising instructions thereon that when executed by the one or more processors cause the system to: (a) partition a population of cells into a plurality of reaction volumes to yield partitioned cells; and (b) assay the partitioned cells for a phenotype to generate signals for the partitioned cells; wherein a coefficient of variation (CV) among the signals for the partitioned cells is 11% or less when the population of cells is a homogenous population of cells.

In some embodiments, the CV is 10% or less. In some embodiments, the CV is 7% or less. In some embodiments, the CV is from about 5% to about 10%.

In some embodiments, the homogenous population of cells comprises at least 1 million cells. In some embodiments, the homogenous population of cells comprises at least 10,000,000 cells.

In some embodiments, the reaction volumes comprise droplets.

In some embodiments, the assay comprises addition of a detection reagent to the partitioned cells. In some embodiments, the assay comprises control of timing of the addition of the detection reagent to the partitioned cells. In some embodiments, the detection reagent comprises an enzyme substrate.

In some embodiments, the assay comprises detection of the signals for the partitioned cells. In some embodiments, the detection comprises optical detection.

In some embodiments, the assay comprises control of timing of detection signals for the partitioned cells.

In some embodiments, the phenotype comprises an enzyme activity.

In some embodiments, (a) comprises control of a volume size of each reaction volume of the plurality of reaction volumes.

In some embodiments, the homogenous population of cells comprises a same genetic material.

In some embodiments, the homogenous population of cells comprises a same gene of interest with a same sequence.

In another aspect, provided herein is a method for generating an improved cell comprising (a) generating a library of mutagenized cells; (b) partitioning the library of mutagenized cells into a plurality of partitions to yield partitioned mutagenized cells; (c) screening the partitioned mutagenized cells for a phenotype; (d) based on the screening, selecting an improved cell from the partitioned mutagenized cells using a threshold gate; (e) using a feedback controller (i) in (b) to maintain a frequency of generation of the plurality of partitions or (ii) in (d) to regulate the threshold gate; and (f) using the improved cell to repeat steps (a)-(d).

In some embodiments, the method comprises using the feedback controller to maintain a frequency of generation of the plurality of partitions. In some embodiments, the plurality of partitions comprise a plurality of droplets.

In some embodiments, the feedback controller adjusts a flow rate to maintain a frequency of generation of the plurality of droplets. In some embodiments, the method comprises using the feedback controller to regulate the threshold gate. In some embodiments, the feedback controller raises or lowers the threshold gate. In some embodiments, the feedback controller regulates the threshold gate to select a target percentage of the partitioned mutagenized cells. In some embodiments, the feedback controller is a proportional-integral-derivative (PID) algorithm. In some embodiments, the feedback controller accounts for deviations in a mechanical instrument, liquid viscosity, or temperature.

In some embodiments, generating the library of mutagenized cells comprises contacting the cell with a mutagen. In some embodiments, generating the library of mutagenized cells comprises transposon mutagenesis, multiplex automated genomic engineering (mage), genome shuffling, random recombination, or non-homologous end joining. In some embodiments, generating the library of mutagenized cells comprises introducing heterologous genetic elements into a cell. In some embodiments, the heterologous genetic elements comprise a promoter, 5' untranslated region, ribozyme, RNA stability sequence, nucleic acid encoding a secretion peptide, nucleic acid encoding a signal peptide, nucleic acid encoding a fusion protein, nucleic acid encoding a DNA binding domain, nucleic acid encoding protein-protein binding region, nucleic acid encoding a codon optimized gene, a 3' untranslated region, or a terminator.

In some embodiments, the mutagenized cells comprise at least 1000 cells, at least 10,000 cells, or at least 1,000,000 cells.

In some embodiments, the method further comprises expanding the library of mutagenized cells before (b). In some embodiments, the expanding occurs in liquid culture.

In some embodiments, wherein the partitioning is controlled by computer readable medium. In some embodiments, each partition of the plurality of partitions of comprises a volume of liquid within a predefined range. In some embodiments, the method further comprises imaging each partition of the plurality of partitions before (c). In some embodiments, the method further comprises ensuring a partition of the plurality of partitions comprises a desired number of mutagenized cells of the mutagenized cells based on the imaging.

In some embodiments, the method further comprises subjecting the plurality of partitions to cell growth conditions between (b) and (c).

In some embodiments, the subjecting comprises controlling temperature, carbon source, pH, media components, or aeration of a subset of partitions of the plurality of partitions.

In some embodiments, the method further comprises monitoring cell growth in the plurality of partitions subjected to the cell growth conditions using imaging.

In some embodiments, the screening comprises adding a detection reagent to each partition of the plurality of partitions. In some embodiments, the detection reagent changes an environment of each partition of the plurality of partitions. In some embodiments, the detection reagent comprises a pH modifying agent, an ionic strength modifying agent, an ion, a substrate, an inhibitor, and enzyme, or a competitor.

In some embodiments, the library of mutagenized cells encodes a molecule of interest. In some embodiments, the screening comprises detecting the molecule of interest; measuring an activity of the molecule of interest, wherein the activity is optionally a catalytic activity, wherein the catalytic activity optionally produces a fluorescent product; determining an amount of the molecule of interest; or determining a function of the molecule of interest.

In some embodiments, the screening comprises performing multiple screens. In some embodiments, the multiple screens comprise applying a more stringent threshold for the phenotype of interest in a subsequent screen of the multiple screens relative to a prior screen of the multiple screens.

In some embodiments, the selecting a partition comprises performing a spectroscopic measurement.

In some embodiments, the selecting a partition comprises applying a threshold.

In some embodiments, (f) comprises removing a mutagenized cell from a selected partition to yield the improved cell. In some embodiments, the method further comprises maintaining viability of the mutagenized cell. In some embodiments, the method further comprises growing the mutagenized cell.

In some embodiments, the method further comprises screening the improved cell for the phenotype of interest.

In some embodiments, the mutagenized cells comprise bacteria.

Also provided herein, in another aspect, is a computer readable medium comprising instruction thereon that when executed by a computer processor cause the computer processor to perform steps (b)-(e).

In another aspect, disclosed herein is a system comprising a computer processor and the computer readable medium.

In another aspect, disclosed herein is an integrated system for sorting desired biological variants comprising two or more integrated units selected from the group consisting of: a strain optimization unit, a molecule optimization unit and a molecule discovery unit, wherein (a) the strain optimization unit comprises a plurality of distinct strain optimization reaction vessels, each with a different strain optimization genetic variant or a fermentation condition(s); (b) the molecule optimization unit comprises a plurality of distinct molecule optimization reaction vessels, each with a different target protein variant or application condition(s); (c) the molecule discovery unit comprises a plurality of distinct molecule discovery reaction vessels, each with a different discovery molecule or application condition(s).

In some embodiments, the two or more units are integrated via a computer readable medium that is capable of performing one or more of the following functions: (i) storage of data sets from each of the two or more integrated units in a data repository, (ii) set a threshold parameter for data to be delivered to the data repository; (iii) instruct each of the two or more units to repeat an input diversity screen.

In some embodiments, the two or more units are integrated via a computer readable medium comprising a machine learning algorithm that integrates data from each of the two or more units for the desired sorting biological variants. In some embodiments, the machine learning algorithm comprises: Elastic-Net Regularized Generalized Linear Models (GLMNET), Support Vector Machine Regression (SVM), Random Forest (RF), Extreme Gradient Boosting (XGBoost), Multilayer Perceptron (MLP), or a Convolutional Neural Network (CNN).

In some embodiments, each of the strain optimization reaction vessels, the molecule optimization reaction vessels, and/or the molecule discovery reaction vessels comprise an average of no more than 1 cell.

In some embodiments, each of the strain optimization reaction vessels, the molecule optimization reaction vessels, and/or the molecule discovery reaction vessels comprise an average of more than 1 cell. In some embodiments, the average of more than 1 cell per well is a clonal population. In some embodiments, the average of more than 1 cell per well comprises a diverse cell population.

In some embodiments, each of the strain optimization reaction vessels, the molecule optimization reaction vessels, and/or the molecule discovery reaction vessels comprise an average of 10-100 cell. In some embodiments, the strain optimization unit, the molecule optimization unit, and the molecule discovery unit are configured to perform single cell analysis. In some embodiments, the strain optimization unit, the molecule optimization unit, or the molecule discovery unit are configured to perform multi-cell analysis.

In some embodiments, the strain optimization unit, the molecule optimization unit and/or the molecule discovery unit is configured to screen at least 100 cells per minute.

In some embodiments, each of the two or more integrated units comprise a consumable unit. In some embodiments, the consumable unit comprises a microfluidic device. In some embodiments, the microfluidic device comprises one or more functional elements selected from the group comprising: a droplet generator, a droplet condenser, a buffer reservoir, a cell incubator, a fluidic injector, a droplet splitter, a droplet sorter, a delay line, and a droplet singulator.

In some embodiments, reaction vessels of the strain optimization reaction vessels, the molecule optimization reaction vessels, or the molecule discovery reaction vessels have a volume that is less than 1 microliter. In some embodiments, reaction vessels of the strain optimization reaction vessels, the molecule optimization reaction vessels, and/or the molecule discovery reaction vessels are in a nanowell array. In some embodiments, reaction vessels of the strain optimization reaction vessels, the molecule optimization reaction vessels, and/or the molecule discovery reaction vessels are droplets, plugs, or wells.

In some embodiments, the integrated system further comprises a detector couple to said one or more units, wherein the detector is selected from the group consisting of: a mass spectrometer, a Raman spectrometer, a microscope, a cell counter, a fluorescence microscope, a light microscope, a flow cytometer, a mass spectrometer, a fluorescence plate reader, a near infrared (NIR) spectrophotometer, and a piezoelectric sensor.

In some embodiments, the integrated system further comprises a reaction vessel movement actuator selected from the group consisting of: a robotic manipulator, a flow generator, an acoustic drop generator, optical tweezers, a thermal drop on demand, a piezoelectric drop on demand.

In some embodiments, each of the different strain optimization genetic variant, each of the target protein variant is in a different cell and/or each of the target discovery molecule is in a different cell.

In some embodiments, each strain optimization genetic variant is generated by random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), or a CRISPR guided DNA polymerase. In some embodiments, the random mutagenesis is saturation mutagenesis.

In some embodiments, each target protein variant is generated by random mutagenesis, Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), or a CRISPR guided DNA polymerase. In some embodiments, the random mutagenesis is saturation mutagenesis or circular permutation.

In some embodiments, each discovery molecule is a DNA encoded molecule found in a metagenomic library, a DNA-encoded library, a library of DNA from one or more microorganisms, or a Function Generator created library.

In some embodiments, the strain optimization unit comprises a strain optimization library comprising a plurality of different genetic variants of a first strain. In some embodiments, the plurality of different genetic variants are classified by metabolic pathway. In some embodiments, the strain optimization library comprises phenotypic, sequence, and metabolic pathway data. In some embodiments, the strain optimization unit comprises a machine learning algorithm. In some embodiments, the machine learning algorithm identifies genetic variants that are optimized across multiple fermentation conditions.

In some embodiments, each of the two or more units comprises a recursive cycle that comprises additional input of biological diversity or conditional diversity.

In some embodiments, the plurality of discrete reaction volumes comprise at least $10^5$ discrete reaction volumes.

In some embodiments, the application conditions comprise one or more of pH, substrate, reaction buffer, and temperature.

In some embodiments, the fermentation conditions comprise one or more of pH, oxygenation, carbon source, buffer concentration, and temperature. In some embodiments, the strain optimization library comprises at least 100 different variants of the first strain. In some embodiments, the strain optimization library is generated by random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.) of the strain. In some embodiments, the strain optimization library is selected from the group consisting of a whole-genome mutagenesis library, a genome-shuffled library, a targeted genomic library, and a transposon library. In some embodiments, the whole-genome mutagenesis library is a whole-genome random mutagenesis library. In some embodiments, the targeted genomic library is a promoter swap library. In some embodiments, the targeted genomic library comprises or encodes for one or more members selected from the group consisting of promoters, 5' untranslated regions, 3' untranslated regions, ribozymes, RNA stability sequences, secretion peptides, fusion proteins, DNA binding domains, protein-protein binding regions, codon optimized genes, codon randomized genes, terminators, and non-homologous end joining. In some embodiments, the transposon library is a promoter insertion library.

In some embodiments, the molecule optimization unit comprises a molecule optimization library comprising a plurality of different genetic variants of a first molecule. In some embodiments, the molecule optimization library is selected from the group consisting of a single gene random mutation library, a site saturation library, a small-insert metagenomic library, and a large-insert metagenomic library.

In another aspect, disclosed herein is an integrated system for sorting desired biological variants comprising: a biological diversity data stream, and a conditional diversity data stream, wherein: (a) each of the data streams is independently programmable, (b) the biological diversity data stream comprises data from a screen of different genomic variants of a target protein or a strain expressing the target protein, and (c) the conditional diversity data stream comprises data from a screen of different conditions of the strain and the target protein; and (d) the biological diversity data stream and the conditional diversity data stream are integrated into an optimization unit that is configured to receive a target parameter and (i) direct the optimization unit to introduce additional biological diversity or conditional diversity until a target protein or a target strain is identified that matches the target parameter, or ii) identify a target protein or a target strain that matches the target parameter.

In some embodiments, the optimization unit comprises a computer readable medium that is capable of performing one or more of the following functions: (i) storage of data sets from each of the biological diversity data stream and the conditional diversity data stream in a data repository; (ii) set a threshold parameter for data to be delivered to the data repository; (iii) instruct the optimization unit to repeat an input diversity screen.

In some embodiments, the optimization unit comprises a computer readable medium comprising a machine learning algorithm that integrates the biological diversity data stream and the conditional diversity data stream for the desired sorting of biological variants. In some embodiments, the machine learning algorithm performs comprises: Elastic-Net Regularized Generalized Linear Models (GLMNET), Support Vector Machine Regression (SVM), Random Forest (RF), Extreme Gradient Boosting (XGBoost), Multilayer Perceptron (MLP), or a Convolutional Neural Network (CNN).

In some embodiments, the strain optimization unit is configured to screen 100 different genomic variants of the target protein or the strain expressing the target protein per minute.

In some embodiments, the strain optimization unit is configured to screen up 100 cells per minute.

In some embodiments, each of the strain optimization unit comprise a consumable unit. In some embodiments, the consumable unit comprises a microfluidic device. In some embodiments, the microfluidic device comprises one or more functional elements selected from the group comprising: a droplet generator, a droplet condenser, a buffer reservoir, a cell incubator, a fluidic injector, a droplet splitter, a droplet sorter, a delay line, and a droplet singulator. In some embodiments, the microfluidic device comprises one or more reaction vessels. In some embodiments, the reaction vessels have a volume that is less than 1 microliter. In some embodiments, the reaction vessels are in a nanowell array. In some embodiments, the reaction vessels are drops, plugs, or wells. In some embodiments, the drops are water-in-oil drops. In some embodiments, the drops are water drops on a surface. In some embodiments, the reaction vessels comprise cells such that there is an average of about 1 cell every 2 or more reaction vessels.

In some embodiments, the integrated system further comprises a detector coupled to said optimization units, wherein the detector is selected from the group consisting of: a mass spectrometer, a Raman spectrometer, a microscope, a cell counter, a fluorescence microscope, a light microscope, a flow cytometer, a mass spectrometer, a fluorescence plate reader, a near infrared (NIR) spectrophotometer and a piezoelectric sensor.

In some embodiments, the integrated system further comprises a reaction vessel movement actuator selected from the group consisting of: a robotic manipulator, a flow generator, an acoustic drop generator, optical tweezers, a thermal drop on demand, a piezoelectric drop on demand.

In some embodiments, each of the different genomic variants of the target protein is in a different cell.

In some embodiments, each of the different genomic variants of the strain is generated by random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), Multiplex Automated Genomic Engineering (MAGE), or CRISPR-enabled trackable genome engineering (CREATE), transposon based mutagenesis, genome shuffling, random recombination, non-homologous end joining, traceable multiplex recombineering (TRMR), or a CRISPR guided DNA polymerase. In some embodiments, the random mutagenesis is saturation mutagenesis or circular permutation.

In some embodiments, each of the different genomic variants of the target protein variant is generated by random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), Multiplex Automated Genomic Engineering (MAGE), or CRISPR-enabled trackable genome engineering (CREATE). In some embodiments, the random mutagenesis is saturation mutagenesis circular permutation.

In another aspect, provided herein is a method for sorting for a final desirable genetic variant comprising: combining data from a diversity screen of biologically diverse genetic elements comprising target protein genetic elements and strain genetic elements with data from a conditional screen of diverse conditions comprising target protein expression conditions and target protein performance conditions; using the combined data set to identify the final desirable genetic variant.

In some embodiments, the conditional screen is performed on one or more genetic elements that are part of the diversity screen.

In some embodiments, generating a first library of cells, each cell comprising a different genetic element from a first library of genetic elements. In some embodiments, the method further comprises generating a second library of cells, each cell comprising a different genetic element from a second library of genetic elements, wherein the first library of genetic elements and the second library of genetic elements are screened under multiple conditions independently. In some embodiments, the first library of genetic elements and the second library of genetic elements are screened using next-generation sequencing (NGS), e.g., a sequencing system by Illumina®, Pacific Biosciences (PacBio®), Oxford Nanopore®, or Life Technologies (Ion Torrent®). to identify mutations that are enriched under the multiple conditions.

In some embodiments, the diversity screen is performed on variants associated with strain optimization. In some embodiments, the strain optimization results in an increased yield, improved fermentation conditions, increased viability, increased tolerance to ion concentrations. In some embodiments, the increased yield is an increase in protein expression and/or an increase in cell proliferation.

In some embodiments, using the combined data set to identify the final desirable genetic variant further comprises a recursive cycle of: (a) identifying one or more intermediate desirable genetic variants with desirable characteristics, (b) obtaining a recombinant library based on the genetic elements of the one or more intermediate desirable genetic variants with desirable characteristics, (c) screening the recombinant library with the conditional screen of diverse conditions, and (d) identifying the final desirable genetic variant or (a) identifying one or more intermediate desirable genetic variants with desirable characteristics.

In some embodiments, the diversity screen is performed on variants associated with target protein discovery. In some embodiments, the diversity screen is performed on variants associated with target protein optimization. In some embodiments, each of the biologically diverse genetic elements is screened in parallel. In some embodiments, each of the biologically diverse genetic elements is screened in series.

In some embodiments, the combined data set comprises data from one or more of a fluorogenic assay, a colorimetric assay, and a reporter cell-based assay. In some embodiments, the fluorogenic assay is a direct assay, an indirect assay, a binding assay, or an in-vivo reporter assay.

In some embodiments, the conditional screen comprises adjusting temperature, media, oxygenation, salinity, pH, mixing, reaction time, metal ion concentration, additive concentration, feed rate, or a combination thereof. In some embodiments, the conditional screen comprises performing two or more different conditions in tandem on a first genetic element. In some embodiments, each of the diverse conditions are run in parallel. In some embodiments, each of the diverse conditions are run in series.

In some embodiments, the method further comprises generating a library of diverse genetic elements. In some embodiments, the generating is performed by random mutagenesis, site directed mutagenesis, site saturation, or genome-shuffling. In some embodiments, the method further comprises introducing each genetic element from the library of diverse genetic elements into a cell or a cell-free system. In some embodiments, the method further comprises separating cells with genetic diversity from the library of diverse genetic elements into different reaction vessels such that each reaction vessel has no more than 1 cell. In some embodiments, the reaction vessel is a drop, plug, or well.

In some embodiments, the desired genetic variant is associated with strain optimization, target molecule optimization, or molecule discovery from an environmental DNA or RNA library.

In some embodiments, the biological diversity is that of strain optimization. In some embodiments, identifying the final desirable genetic variant comprises measuring one or more characteristics of a strain including expression level, cell viability, cell proliferation, and sensitivity to divalent cation concentration.

In some embodiments, the method further comprising generating a library of modified strains by site-directed mutagenesis, random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), or a CRISPR guided DNA polymerase. In some embodiments, the random mutagenesis is saturation mutagenesis.

In some embodiments, the biological diversity is of target protein optimization. In some embodiments, identifying the desirable genetic variant comprises measuring one or more characteristics of a target protein including substrate specificity, substrate state, sensitivity to divalent cation concentration, temperature tolerance, catalytic performance, resistance to protease degradation, pH tolerance, sensitivity to an inhibitor, cofactor preference, enzymatic rate, half-life, activity when immobilized to a support, or a sensitivity to a gas. In some embodiments, the substrate state is soluble or surface adsorbed. In some embodiments, the diversity screen further comprises enriching the genetic elements based on the one or more characteristics of the target protein.

In some embodiments, the target protein genetic elements comprise gene regions, sequence motifs, and protein structural classes. In some embodiments, a gene encoding the target protein is COL1A1 (human Type 1 collagen). In some embodiments, the target protein is a structural protein, an enzyme, a surface receptor protein, a peptide hormone, an immune system component, or a bioactive peptide. In some embodiments, the target protein is an industrial enzyme. In some embodiments, the target protein is a therapeutic protein. In some embodiments, the peptide hormone is insulin or signaling factor. In some embodiments, the structural protein is collagen or a food-based protein. In some embodiments, the enzyme is a lipase or a poly(ethylene terephthalate) hydrolase (PETase).

In some embodiments, the biological diversity is of a discovery library. In some embodiments, the discovery library is an environmental DNA (eDNA) library.

In some embodiments, the conditional diversity is of one or more fermentation conditions. In some embodiments, the one or more fermentation conditions include: temperature, media, oxygenation, salinity, pH, mixing, feeding schedule, carbon source, or a change in any one or combination thereof. In some embodiments, the method further comprises identifying industrial fermentation conditions to produce the desirable genetic variant in a volume greater than 100 milliliters.

In some embodiments, the conditional diversity is of one or more application conditions. In some embodiments, wherein the application conditions include pH, temperature, substrate, reaction buffer, and attachment to a support.

In some embodiments, the method further comprises identifying the desirable genetic variant comprises sequencing. In some embodiments, sequencing comprises performing PCR. In some embodiments, sequencing comprises performing next-generation sequencing (NGS). In some embodiments, identifying comprises identifying open reading frames that encode the desirable genetic variant. In some embodiments, the method may further comprise purifying one or more nucleic acid molecules.

In yet another aspect of the present disclosure, provided herein is a method for identifying a final optimized protein or a final optimized strain that meets a performance criteria comprising: (a) obtaining a data set comprising: (i) data of a plurality of different genetic elements selected from two or more of a) different genetic variants of a strain, b) different genetic variants of a protein, or c) different genes encoding distinct proteins, and (ii) for each of the plurality of different genetic elements, data of a plurality of different conditions, (b) integrating the data set to identify or predict a final optimized protein or a final optimized strain that meets the performance criteria or identify additional data to introduce to (a).

In some embodiments, the performance criteria include target protein expression level, target protein stability, target protein substrate specificity, target protein activity, strain proliferation, strain tolerance to fermentation conditions, target protein folding, target protein-to-byproduct ratio, or a target protein modification.

In some embodiments, the data of the plurality of conditions comprise target protein stability, strain tolerance to divalent cation concentrations, target protein substrate specificity, temperature tolerance, pH tolerance, expression level, or strain viability.

In some embodiments, the data set is applied to a machine learning algorithm, wherein the additional data in (b) is identified by the machine learning algorithm. In some embodiments, the additional data is a library of genetic elements or additional conditions.

In some embodiments, the data set comprises data from one or more of a fluorogenic assay or a colorimetric assay. In some embodiments, the fluorogenic assay is a direct assay, an indirect assay, a binding assay, or an in-vivo reporter assay.

In some embodiments, integrating the data set to identify additional data in (b) further comprises: (i) identifying an intermediate protein of interest or intermediate strain of interest that meets a subset of performance criteria, (ii) identifying an additional plurality of variants with at least 70%, 80%, or 90% homology to the intermediate protein of interest or the intermediate strain of interest as additional data to introduce to (a), and (iii) for each of the additional plurality of variants, obtaining additional data of the plurality of different conditions to introduce to (a). In some embodiments, the method further comprises obtaining additional data of the plurality of different conditions either a) individually when additional plurality of variants comprises less than 100 members orb) at a population level when the additional plurality of variants comprises more than 100 members.

In some embodiments, the genetic variants of the strain is from a library of strain genetic variants. In some embodiments, the library of strain genetic variants is selected from the group consisting of a whole-genome mutagenesis library, a genome-shuffled library, a targeted genomic library, and a transposon library. In some embodiments, the whole-genome mutagenesis library is a whole-genome random mutagenesis library. In some embodiments, the targeted genomic library comprises or encodes for one or more members selected from the group consisting of promoters, 5' untranslated regions, 3' untranslated regions, ribozymes, RNA stability sequences, secretion peptides, fusion proteins, DNA binding domains, protein-protein binding regions, codon optimized genes, codon randomized genes, terminators, and non-homologous end joining. In some embodiments, the targeted genomic library is a promoter swap library. In some embodiments, the transposon library is a promoter swap library. In some embodiments, the library of strain genetic variants is generated by random mutagenesis, Multiplex Automated Genomic Engineering (MAGE), or CRISPR-enabled trackable genome engineering (CREATE).

In some embodiments, the different genetic variants of the protein is a library of target protein-encoding genetic variants. In some embodiments, the data set comprises different protein-encoding genetic variants and the additional data comprises a subsequence library of residue-encoding variants. In some embodiments, the subsequence library is generated by gene shuffling. In some embodiments, the library of target protein-encoding genetic variants is generated by random mutagenesis, Multiplex Automated Genomic Engineering (MAGE) or CRISPR-enabled trackable genome engineering (CREATE). In some embodiments, the library of target protein-encoding genetic variants is selected from the group consisting of a single gene random mutation library, a site saturation library, a small-insert metagenomic library, and a large-insert metagenomic library.

In some embodiments, the different genes encoding distinct proteins is an environmental DNA (eDNA) library.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 6A shows the evolution of a library of cells over rounds of enrichment in a first generation. FIG. 6B shows the evolution of a library of cells over rounds of enrichment in a second generation. FIG. 6C shows the evolution of a library of cells over rounds of enrichment in a third generation.

FIG. 12 shows example data of mutations discovered from molecule discovery.

DETAILED DESCRIPTION

Figure 1:
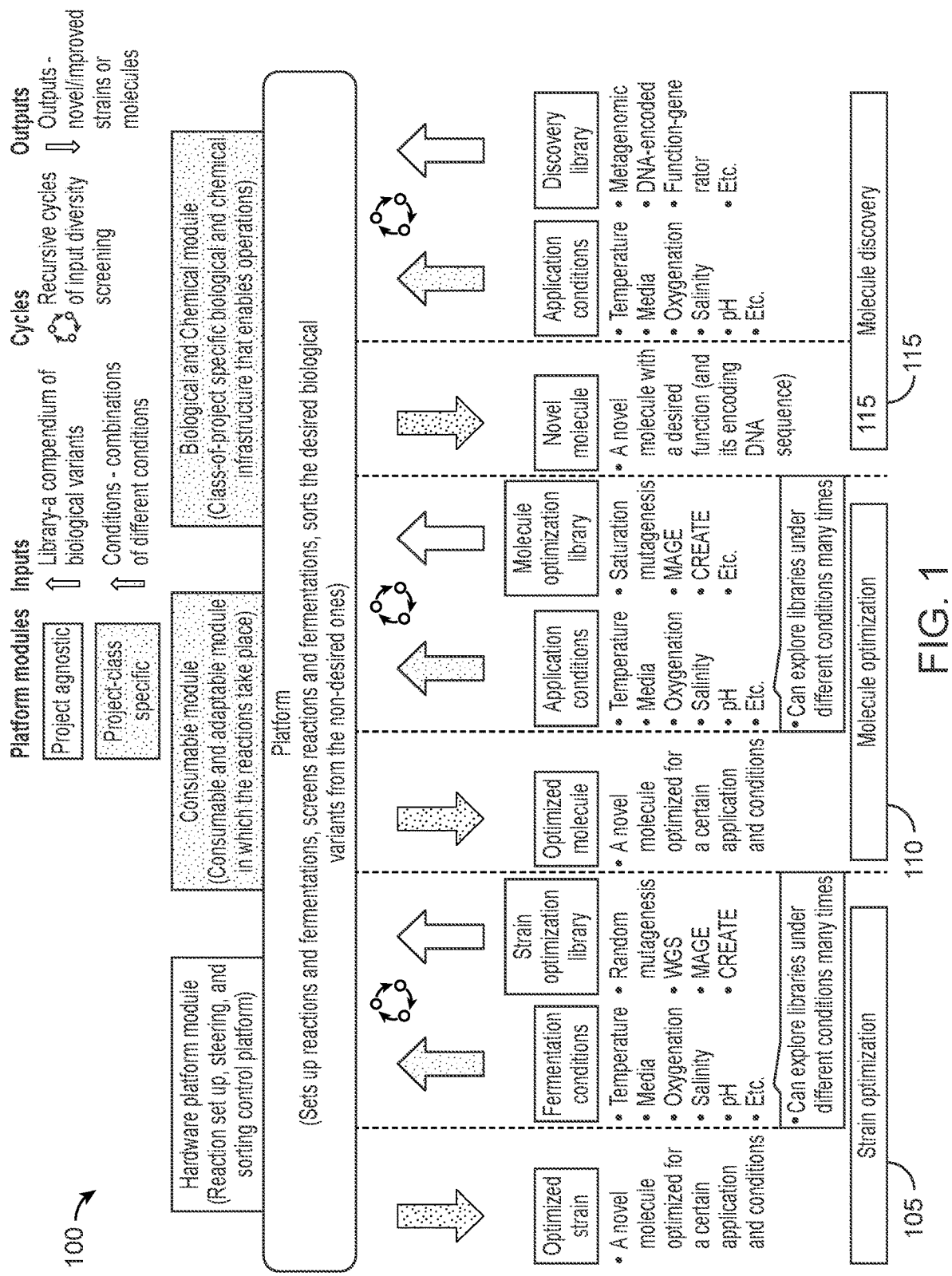
FIG. 1 schematically illustrates an example integrated system comprising a strain optimization unit, a molecule optimization unit, and a molecule discovery unit for sorting desirable biological variants.

Disclosed herein are methods and systems for sorting and identifying desired biological variants in a high-throughput platform. Generally, the systems and methods described herein involve using one or more integrated units selected from the group consisting of a strain optimization unit, a molecular optimization unit, and a molecule discovery unit. The methods and systems employed herein may utilize large data sets that are input into or output from one or more of the integrated units (e.g., the strain optimization unit, the molecular optimization unit, and/or the molecule discovery unit) to generate predictions or outputs on novel molecules having a desired characteristic, optimized molecules (e.g., having enhancement of a desired characteristic), or strains (e.g., naturally occurring or engineered prokaryotic or eukaryotic organisms) displaying such a desired characteristic. In some aspects of the present invention, the platforms, systems and methods described herein may be applied to directed evolution, molecule discovery, and molecular engineering for optimization of the desired characteristic.

The below terms are discussed to illustrate meanings of the terms as used in this specification, in addition to the understanding of these terms by those of skill in the art. Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the term "biological diversity" generally refers to a variation or difference among one or more biological molecules. Biological molecules may be, for example, molecules that exist or can be synthesized in biology, including, but not limited to: ions, small molecules, macromolecules (e.g., peptides, proteins, lipids, carbohydrates, nucleic acid molecules), metabolites, a cell, a tissue, and/or combinations thereof. The variation or difference among the one or more biological molecules may be functional, structural, or both. The variation or difference among the one or more biological molecules may include a difference or variation in the biological, chemical, physical, mechanical, optical, thermal, or other activity, function, structure, or property. Biological diversity may refer to differences in biological molecules that are naturally occurring, found in pathological conditions, or are non-naturally occurring, e.g., synthesized or engineered. Biological diversity may refer to genotypic differences or phenotypic differences.

As used herein, the term "biological variant" generally refers to a form or version of a biological molecule that exhibits variety or diversity. The biological variant may be a member of a group (e.g., a library) comprising different biological molecules, such as cells, organelles, nucleic acid molecules, peptides or proteins, lipids, carbohydrates, metabolites, or a combination thereof. The different biological molecules may be the same type or different types of molecules. For example, two biological variants can comprise two DNA molecules that encode for the same protein or peptide. Alternatively, the two biological variants can comprise two DNA molecules that encode for different proteins or peptides. In some instances, two or more biological variants may exhibit sequence homology. For example, the two or more biological variants may exhibit at least 10%, at least 20%, at least 30%, at least 40%, at least 50%, at least 60%, at least 70%, at least 80%, at least 90%, at least 95% or greater sequence or structural homology. In some instances, two or more biological variants may exhibit minor differences in composition, structure, or function. For example, the two or more biological variants may differ in composition, structure, function by less than 1%, less than 0.1%, less than 0.01%, less than 0.001%, less than 0.0001%, or lower. In some instances, a biological variant may be a genetic variant or a molecular variant.

As used herein, a "genetic variant" generally refers to a member of a group (e.g., library) comprising different genetic elements, such as a sequence of RNA, DNA, or other nucleic acid molecule, which may encode for the same or different protein, peptide, motif, amino acid, or other protein structural element. The genetic variants may have different nucleic acid sequences, structures, modifications (e.g., methylation), base substitutions or other differences in genetic elements. The genetic variants may comprise mutagenized cells. The genetic variants may encode proteins or peptides, or they may be non-coding nucleic acid molecules (e.g., introns, transfer RNA, ribosomal RNA, regulatory RNA, etc.). In some instances, two or more genetic variants may exhibit sequence homology. For example, the two or more genetic variants may exhibit at least 10%, at least 20%, at least 30%, at least 40%, at least 50%, at least 60%, at least 70%, at least 80%, at least 90%, at least 95% or greater sequence homology.

As used herein, the terms "molecular variant" generally refers to a member of a group (e.g., library) comprising different molecules, such as small molecules, therapeutic molecules, polymers or polymeric molecules, biological molecules such as RNA, DNA, or other nucleic acid molecule, protein, peptide, motif, amino acid, or other protein structural element, lipids, carbohydrates, glycoproteins, lipoproteins, or a combination thereof. The molecular variants (e.g., polymer variant) may have different chemical compositions, structures, modifications, charge, mass, or other physical or chemical property. For example, a polymer variant can be a nucleic acid molecule or a peptide or a protein. The nucleic acid molecule can be RNA or DNA. The RNA may be coding or noncoding and may comprise messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. In some instances, two or more molecular variants may exhibit sequence or compositional homology. For example, the two or more molecular variants may exhibit at least 10%, at least 20%, at least 30%, at least 40%, at least 50%, at least 60%, at least 70%, at least 80%, at least 90%, at least 95% or greater compositional homology. In some instances, a biological variant or genetic variant is or comprises a molecular variant. A molecular variant may be a biological or genetic variant, or conversely, a biological variant may be a genetic variant or a molecular variant.

Strain Optimization, Molecule Optimization and Molecule Discovery

Disclosed herein are systems and methods for sorting and identifying desired biological variants. The systems and methods disclosed herein may generally involve inputting data into an integrated system and outputting data and/or predictions on structural-functional relationships of molecules, novel molecules having a desired characteristic, optimized (e.g., engineered or evolved) molecules having a desired characteristic, strain information (e.g., nucleic acid or protein information of an organism producing a molecule having a desired characteristic) and/or an optimized strain (e.g., a cell, nucleic acid sequence, or protein sequence) having a desired performance. A system can be an integrated system that comprises one or more integrated units selected from the group consisting of: a strain optimization unit, a molecule optimization unit, and a molecule discovery unit. The integrated units may individually or collectively be configured to obtain experimental data or use experimental data as an input along with other inputs, as is described herein. Alternatively or in addition to, the integrated units may individually or collectively be configured to obtain or use large data sets (e.g., from databases, publicly available sources, etc.) as an input. Overall, the systems and methods described herein are useful in high-throughput screening of biological variants in a platform technology, using both empirical data as well as large data sets (e.g., from publicly available databases) for molecular and strain optimization and discovery.

In some instances, each of the one or more integrated units utilize data sets (e.g., from databases, empirical data, data generated from the other integrated units, etc.) as inputs and output data and/or one or more predictions regarding (i) an optimal strain (e.g., using the strain optimization unit, which may output information on at least one organism with an encoding molecule (e.g., nucleic acid molecule such as DNA or RNA) for a desired functional characteristic (e.g., protein or enzymatic activity, molecular binding or affinity, or other metabolic or phenotypic trait)), (ii) an optimal molecule (e.g., using the molecule optimization unit, which may output a small molecule, peptide, or protein), or (iii) a novel molecule (e.g., using the molecule discovery unit, which may output a small molecule, peptide, or protein) with a desired functional characteristic. In some cases, at least one of the integrated units are configured to obtain experimental data, which in some instances is used as an input into the same or different integrated unit for generating a prediction on an optimal strain, an optimal molecule, or a novel molecule.

(i) Strain Optimization Unit

In some instances, the systems and methods disclosed herein utilize a strain optimization unit, which may be useful in screening and optimizing a strain (e.g., a cell type, cells with genetic variants, etc.) for a functional characteristic, in a highly predictable, high-throughput format. Such a strain optimization unit may comprise the use of one or more feedback loops or controllers, which may aid in increasing predictability and consistency of strain optimization (e.g., a predictable functional characteristic such as the amount of product produced, activity level of the product, or the consistency of the generation of increasingly improved cells, etc.).

The strain optimization unit may be useful in iteratively screening a strain (e.g., eukaryotic or prokaryotic organism with genetic variation) for a desired functional characteristic. For example, a method for strain optimization may comprise: (a) introducing a library of genetic variants into a plurality of cells, (b) subjecting the plurality of cells with the genetic variants to conditions sufficient for screening of the plurality of cells for a desired functional characteristic (e.g., phenotypic trait (e.g., increased production or secretion of a protein) or metabolic trait), (c) isolating the cells that have the desired characteristic, (d) generating an additional library of genetic variants, in which the additional library of genetic variants comprise variants that encode for the desired characteristic, and (e) repeating (a)-(d) until a performance requirement is met. In another example, strain optimization may be performed for generating a cell with an improved characteristic. In such an example, the method for generating the improved cell or the cell with an improved characteristic may comprise: (a) generating a library of mutagenized cells, (b) partitioning the library of mutagenized cells into a plurality of partitions (e.g., reaction vessels) to yield partitioned mutagenized cells, (c) screening the partitioned mutagenized cells for a phenotype, and (d) based on the screening, selecting an improved cell from the partitioned mutagenized cells (e.g., using a threshold gate), (e) and using a feedback controller (i) in (b) to maintain a frequency of generation of the plurality of partitions or (ii) in (d) to regulate the threshold gate (f) using the improved cell to repeat (a)-(d). In general, the strain optimization unit may be useful in generating libraries of genetic variants, introducing the genetic variants into cells, optionally culturing the cells under varying growth, culture, or fermentation conditions, screening the cells for a desired trait, combining portions of desired genetic variants or enriching the traits (e.g., via generating recombinant genes or transgenes comprising the desired trait) to generate a new library of genetic variants, and repeating the process until a performance criterion or requirement is met (see, e.g., Examples 1, 4 and 5).

The strain optimization unit may comprise an experimental module, which may comprise a plurality of distinct strain optimization reaction vessels, each with a different strain optimization genetic variant or a fermentation condition. By way of example, the strain optimization unit may be used for directed evolution approaches and engineering of a cell or population of cells to have a desired functional characteristic. In such an example, biological variants, such as a plurality of cells having genetic variations (which may be naturally occurring or induced, e.g., via mutagenesis or transformation, transduction, of a transgene or recombinant gene, etc.) or a library of mutagenized cells, may be screened in the reaction vessels of the strain optimization unit, optionally under a plurality of fermentation conditions, and the cells that have a desired functional characteristic may be enriched (e.g., isolated, collected), and analyzed (e.g., via sequencing) to identify the genetic variant (e.g., using the nucleic acid or gene sequence). The genetic variants that have the desired characteristic (e.g., a gene of interest, expression of a protein under a specified fermentation condition, or other phenotypic or metabolic trait) may be isolated and recombined into a plurality of recombinant genes and re-screened, e.g., via transformation, transfection, or transduction of the recombinant genes into cells, optionally culturing the cells, and enriching or isolating the cells with the desired functional characteristic, optionally with a more stringent performance requirement. The processes may be iterated in a recursive cycle such that each cycle (also referred to herein as "diversity screen") has a more stringent performance requirement (e.g., a higher or lower metabolic activity, enzymatic activity, or higher or lower expression of a phenotypic trait, increased yield, robustness under a set of fermentation conditions, e.g., tolerance to differences in ion concentration, temperature, pH, etc., increased viability, increased cell proliferation or growth). Alternatively or in addition to, multiple processes may be run in parallel and/or in series. The recursive cycle and operations contained therein may be performed for as many cycles as necessary for a desired performance requirement to be met. In some instances, additional input of biological diversity (e.g., via recombination of genes and introduction of recombined genes in cells or via mutagenesis, e.g., exposure to mutagens such as ultraviolet radiation, ethyl methyl sulfonate, etc.) may be introduced during the recursive cycle. Alternatively or in addition to, the condition diversity (e.g., change in fermentation or culture conditions) may be introduced during the recursive cycle.

In some embodiments, the strain optimization may be achieved by performing multiple rounds of screening and enriching, adding in biological diversity (e.g., via mutagenesis) to generate a new strain generation, and conducting additional rounds of screening and enriching. In an example, a library of mutagenized cells may be generated and optionally cultured under conditions sufficient to grow the cells. The library of mutagenized cells may then be partitioned into reaction vessels and optionally cultured under conditions sufficient to grow or expand the cells (e.g., under a defined set or sets of fermentation conditions, in liquid culture, etc.). In some instances, individual cells may be partitioned into the individual reaction vessels. Such partitioning may be assisted by a computer readable medium and feedback control, as is described elsewhere herein. Subsequently, the partitioned cells may be subjected to screening, and based on the screening, the cells that have a desired functional characteristic (e.g., a desired phenotype) may be enriched (e.g., isolated, collected, or selected). These enriched cells may be subjected to additional rounds of enrichment (e.g., re-partitioned, cultured, screened, and enriched). After a defined (e.g., user-determined or computer-guided decision) number of rounds of enrichment, the enriched cells may be further analyzed (e.g., via sequencing) to identify the genetic variants. The most favorable genetic variants (e.g., those that result in the highest functional performance) may be isolated and recombined into a plurality of recombinant genes to provide a new generation of biological variants (e.g., genetic variants, mutagenized cells, etc.). The new generation of biological variants may then be re-screened, e.g., via transformation, transfection, or transduction of the recombinant genes into cells, optionally culturing the cells, and enriching or isolating the cells with the desired functional characteristic, optionally with a more stringent performance requirement. See, e.g., FIGS. 4-5.

Any number of rounds or generations may be iterated to achieve a desired functional performance. For example, within a generation, at least 1, at least 2, at least 3, at least 4, at least 5, at least 6, at least 7, at least 8, at least 9, at least 10, at least 50, at least 100, at least 500, at least 1,000 or more rounds of enrichment or sorting may be performed. Alternatively, within a generation, at most about 1,000, at most about 500, at most about 100, at most about 50, at most about 10, at most about 9, at most about 8, at most about 7, at most about 6, at most about 5 or fewer rounds of enrichment or sorting may be performed. Likewise, any number of generations (e.g., mutagenesis or addition of biological diversity) may be performed, e.g., 1, 2, 3, 4, 5, 6, 7, 8, 9, 10, 50, 100, or more generations may be generated for optimization. Alternatively, at most about 100, at most about 50, at most about 10, at most about 9, at most about 8, at most about 7, at most about 6, at most about 5, at most about 4, at most about 3, at most about 2 or fewer generations (e.g., rounds of mutagenesis) may be performed.

In some instances, it may be useful to screen a variety of fermentation conditions using the strain optimization unit. In such cases, a plurality of cells, optionally comprising genetic variations (which may be naturally occurring or induced, as described herein) may be cultured in different fermentation conditions. Non-limiting examples of different operable parameters of fermentation conditions include: temperature, feed rate, growth or nutrition medium composition, oxygenation, salinity, pH, carbon source, carbon dioxide concentration, buffer concentration, ion concentration, duration of culture, perfusion or mixing, aeration, reaction time, metal ion concentration, additive concentration, feeding schedule, a combination thereof, or a change in any one or combination thereof. One or more operable parameters of fermentation conditions may be tuned for a given set of genetic variants. The plurality of cells can be cultured under the defined fermentation conditions prior to partitioning the cells in reaction vessels, or the cells may be cultured with the defined fermentation condition in the reaction vessel. The fermentation conditions may be the same or different across a subset or all of the reaction vessels and may be screened independently, in series or in parallel. Screening of such variants under the varying fermentation conditions may be useful in identifying genetic variants that result in a functional characteristic under a defined fermentation condition, e.g., increased yield, proliferation, or protein expression level in an environment that is hypoxic, low or high temperature, non-normal pH, low glucose, etc. In some instances, screening of the variants under the varying fermentation conditions may be useful in identifying industrial (e.g., in volumes greater than 100 milliliters (mL), 1 liter (L), 2 L, 5 L, or more) fermentation conditions that can produce the desired functional characteristic.

The cultured cells may then be screened in the reaction vessels of the strain optimization unit, and the cells that have a desired functional characteristic under the defined fermentation conditions may be isolated, collected, and analyzed (e.g., via sequencing) to identify the genetic variant (e.g., using the nucleic acid or gene sequence). In some instances, the sequencing may be used to identify mutations that are enriched under the defined fermentation or culture conditions. The genetic variants that have the desired characteristic (e.g., a gene of interest, expression of a protein under a specified fermentation condition, or other phenotypic or metabolic trait) may be isolated, optionally further cultured (e.g., under conditions sufficient to maximize organism viability or proliferation) and recombined into a plurality of recombinant genes and re-screened, e.g., via transformation, transfection, or transduction of the recombinant genes into cells, culturing the cells under the fermentation conditions, and isolating the cells with the desired functional characteristic, optionally with a more stringent performance requirement (e.g., growth under a more stringent or specified fermentation condition). The processes may be iterated in a recursive cycle such that each cycle has a more stringent performance requirement (e.g., a more stringent fermentation condition, e.g., hypoxic conditions, high or low temperature, low glucose, etc.). The recursive cycle and operations contained therein may be performed for as many cycles as necessary for a desired performance requirement to be met. In some instances, multiple processes may be run in parallel. In some instances, additional input of biological diversity (e.g., via recombination of genes and introduction of recombined genes in cells or via mutagenesis, e.g., exposure to mutagens such as ultraviolet radiation, ethyl methyl sulfonate, etc.) may be introduced during the recursive cycle, thereby generating a new generation of strains or mutagenized cells. Alternatively or in addition to, the condition diversity (e.g., change in fermentation or culture conditions) may be introduced during the recursive cycle.

The cells may be cultured at any useful or convenient step. For example, following introduction of biological diversity (e.g., via targeted or non-targeted mutagenesis), the cells may be cultured. The cells may be cultured following partitioning, screening, enrichment, or after additional cycles of adding biological diversity. It will be appreciated that the cells may be cultured under different conditions at different stages, depending on the process. For example, the cells may be cultured in a sub-optimal (e.g., low oxygen, low nutrient, etc.) condition prior to screening, but subsequent to enrichment, the cells may be cultured in a more optimal fermentation condition to promote growth.

Multiple experimental conditions may be screened simultaneously using the systems and methods described herein. For instance, the strain optimization unit may be configured to simultaneously screen or analyze millions of reaction volumes or biological variants (e.g., cells with hundreds to millions or more genetic variants) grown under the same or different fermentation conditions. Screening may be performed by performing one or more assays described herein, e.g., via imaging of the reaction vessels and sorting of cells and/or reaction vessels based on the results of the imaging. Beneficially, the strain optimization unit may provide multiplexed, multiparametric information on genetic variants and environmental (or fermentation) conditions of the biological variants. Additionally, the strain optimization unit may be beneficial in selecting a strain based on a desired performance criterion (e.g., having the desired characteristic such as a threshold enzymatic activity level or other metabolic or phenotypic trait) or fermentation condition.

Reaction vessels: The reaction vessels of the strain optimization unit may be, for instance, droplets or plugs, wells (e.g., microwells, nanowells, picowells, etc.), vials, tubes, flasks, or other container. In some instances, the reaction vessels are comprised in a microfluidic device. In some instances, the reaction vessels are a member of an array, e.g., a microwell array or plate (or other substrate), a nanowell array or plate (or other substrate), etc. Multiple types of reaction vessels may be used (e.g., droplets and wells) for any of the processes described herein, either simultaneously or sequentially. The reaction vessels may be physically distinct or discrete, or the reaction vessels may be capable of being merged or coalesced. The reaction vessels may comprise a substrate onto which one or more reagents may adsorb, or the reagents may be in solution.

Each reaction vessel can comprise a different strain optimization genetic variant for screening. For example, it may be useful to screen a library of genetic variants for a desired functional characteristic (e.g., biomolecular (e.g., enzymatic) activity, biomolecule interaction, phenotypic or metabolic trait); accordingly, each reaction vessel may be configured to contain a different genetic variant for screening. In some cases, each reaction vessel comprises one or more cells having the genetic variant. For example, each reaction vessel may comprise a single cell or more than one cell having a single genetic variant that is different than the genetic variants of other cells in other reaction vessels. Alternatively or in addition to, each reaction vessel may comprise a clonal population of cells with a single genetic variant. In other examples, it may be useful to screen different genetic variants within a single reaction vessel; accordingly a reaction vessel may comprise a mixture of cells with different genetic variants. In such an example, each reaction vessel may comprise a combination of cells and genetic variants. In some instances, such as in the case of droplets, one or more droplets may be coalesced or merged to combine the cells or genetic variants.

A reaction vessel may comprise a single cell or multiple cells. For example, a single reaction vessel may comprise 0 cells, 1 cell, 2 cells, 3 cells, 4 cells, 5 cells, 6 cells, 7 cells, 8 cells, 9 cells, 10 cells, 20 cells, 50 cells, 100 cells, 200 cells, 500 cells, 1,000 cells or more. One or more reaction vessels may comprise different numbers of cells; for example, the reaction vessels may comprise on average 10 to 100 cells. The cell or cells may have the same origin or have different origins. The cell or cells may be of the same type or may be different types. The cell or cells may be from any useful species or origin, e.g., bacterial, yeast, mammalian (e.g., human, primate, rat, mice, rabbit, goat, porcine, bovine, ovine, equine), reptilian, avian, etc. The cell or cells may be prokaryotic, eukaryotic or a combination thereof. The cells may be from a unicellular organism or a multicellular organism. The cells may be from a cell sample obtained from a subject. The subject may be mammalian (e.g., human, primate, rat, mice, rabbit, goat, porcine, bovine, ovine, equine), reptilian, avian, etc. The cell sample may be obtained by biopsy, swab, irrigation, brushing, collection, etc. Each reaction vessel may be configured to perform single-cell or multi-cell analysis.

In some instances, a reaction vessel may not comprise a cell and may comprise reaction conditions sufficient to perform cellular processes (e.g., transcription, translation, enzyme reactions, etc.). In such instances, the reaction vessels may comprise a cell-free system that comprises any useful reagents for performing such cellular processes, including, but not limited to: enzymes (e.g., DNA polymerases, RNA polymerases, reverse transcriptases, helicases, ligases), nucleic acid molecules (e.g., nucleotides, transfer RNAs), proteins (e.g., ribosomes), lipids, carbohydrates, metabolites, or any combination thereof.

The reaction vessels may be configured to be assessed or analyzed in a high-throughput manner. For instance, the strain optimization unit (e.g., experimental module) may be configured to screen at least 100 cells/min, at least 500 cells/min, at least 1,000 cells/min, at least 5,000 cells/min, at least 10,000 cells/min, at least 50,000 cells/min, at least 100,000 cells/min or more. Alternatively or in addition to, the reaction vessels may be screened in a high-throughput manner. For instance, the strain optimization unit may be configured to screen at least 10 reaction vessels/min, at least 100 reaction vessels/min, at least 500 reaction vessels/min, at least 1,000 reaction vessels/min, at least 5,000 reaction vessels/min, at least 10,000 reaction vessels/min, at least 50,000 reaction vessels/min, at least 100,000 reaction vessels/min. In some instances, the strain optimization unit may be configured to screen at least 10 reaction volumes/min, at least 100 reaction volumes/min, at least 500 reaction volumes/min, at least 1,000 reaction volumes/min, at least 5,000 reaction volumes/min, at least 10,000 reaction volumes/min, at least 50,000 reaction volumes/min, at least 100,000 reaction volumes/min.

Any number of reaction vessels may be generated or used within a given duration. In some instances, it may be beneficial to screen different numbers of reaction vessels (or volumes). Accordingly, the number of reaction vessels (or volumes) used or generated may be adjusted according to the suitable application or experimental purpose. For instance, when large numbers of discrete reaction volumes are useful e.g., for screening purposes (e.g., for strain optimization), at least 10,000 reaction volumes, at least 100,000 reaction volumes, at least 1,000,000 reaction volumes, at least 10,000,000 reaction volumes, at least 100,000,000 reaction volumes or more reaction volumes may be used. In other instances, smaller numbers of discrete reaction volumes may be useful or required (e.g., for a targeted screen or for rational design of experiments with a limited number of species for screening). In such instances, at most 100,000,000 reaction volumes, at most 10,000,000 reaction volumes, at most 1,000,000 reaction volumes, at most 100,000 reaction volumes, at most 10,000 reaction volumes, at most 1,000 reaction volumes or fewer may be used or generated.

In some instances, the reaction vessels are comprised within a microfluidic device. The microfluidic device may be a portion of a consumable or disposable unit of the strain optimization unit. In some cases, the reaction vessels may comprise nanowells or droplets (or plugs). In such cases, the microfluidic device may comprise one or more functional elements such as a droplet generator, a droplet condenser, a droplet merger, a buffer reservoir, a cell incubator, a fluidic injector, a droplet splitter, a droplet sorter, a delay line, a droplet singulator, etc.

The reaction vessels may accommodate any useful volume. The reaction vessels may have a volume that is less than 100 microliters (µL), less than 10 µL, less than 1 µL, less than 500 nanoliters (nL), less than 200 nL, less than 100 nL, less than 50 nL, less than 20 nL, less than 10 nL, less than 5 nL, less than 2 nL, less than 1 nL, less than 500 picoliters (pL), less than 200 pL, less than 100 pL, less than 50 pL, less than 20 pL, less than 10 pL, less than 5 pL, less than 2 pL, less than 1 pL, less than 500 femtoliters (fL), or less. In some embodiments, the reaction vessels may have a volume that is greater than 500 fL, greater than 1 pL, greater than 2 pL, greater than 5 pL, greater than 10 pL, greater than 20 pL, greater than 50 pL, greater than 100 pL, greater than 200 pL, greater than 500 pL, greater than 1 nL, greater than 2 nL, greater than 5 nL, greater than 10 nL, greater than 20 nL, greater than 50 nL, greater than 100 nL, greater than 200 nL, greater than 500 nL, greater than 1 µL, greater than 2 µL, greater than 5 µL, greater than 10 µL, greater than 100 µL, or more. It will be appreciated that the reaction volume may fall within a range of volumes, e.g., between about 1 pL to about 20 pL, between about 10 pL to 100 nL, etc. A plurality of reaction vessels may be used, and the plurality of reaction vessels may comprise the same or different volumes. The volumes of the plurality of reaction vessels may be controlled using a computer implemented method, as is described further elsewhere herein.

In the case of droplets, the droplets may comprise any useful composition. For instance, the droplets may comprise water-in-oil droplets, oil-in-water droplets, water-oil-water droplets, oil-water-oil droplets, and the like. In some instances, the droplets comprise droplets (e.g., oil, water) in air on or adjacent to a surface and may be encompassed in a reaction vessel (e.g., well). The droplets may comprise multiple emulsions, e.g., double emulsions, triple emulsions, etc.

Assays: In some instances, the sorting of the biological variants may comprise the use of one or more screening operations. The screening operation may include an assay, e.g., a direct assay, an indirect assay, a binding assay, a reporter assay, a fluorogenic assay, a reporter cell-based assay, a chromogenic or colorimetric assay, etc. One or more immunological assays may be used, including, but not limited to: enzyme-linked immunosorbent assay (ELISA), sandwich ELISA, proximity ligation assay, etc. In some instances, a reporter molecule or selection molecule is used for screening. The assay or reporter or selection molecules may be useful in the detection of the presence of a genetic variant or a functional characteristic (e.g., phenotypic or metabolic trait) of the biological variant. For example, in cases where the desired biological variant is a cell that comprises enzymatic activity, the cells in the reaction vessels may be screened in the presence of a chromogenic or fluorogenic substrate that changes color or fluoresces upon conversion of the substrate to a product by the desired enzymatic activity. In such an example, the reaction vessels that exhibit a change in color or fluorescence may indicate that the cell comprises the desired enzymatic activity; subsequently that cell may be isolated and further analyzed (e.g., via sequencing such as next-generation sequencing (NGS) or PCR-based sequencing, open-reading frame identification or analysis, protein analysis, etc.) to determine information on the biological variant (e.g., DNA or RNA sequence, protein sequence or composition, etc.). In other examples, the desired biological variants may comprise a selection or reporter molecule; for example, in the case of selection molecules, only cells with the desired trait may survive in a given culture condition (e.g., only cells with transgenes or recombinant genes that encompass antibiotic resistance will survive in a growth medium comprising antibiotics). The surviving cells may be screened for the desired functional characteristic and those that have the desired functional characteristic may be subjected to further analysis. In yet another example, only cells with the desired trait may express a reporter molecule (e.g., fluorescent or detectable protein) indicating that a transgene or recombinant gene is present. In such examples, cells exhibiting a desirable trait or functional characteristic may be isolated from the reaction vessel and subjected to further analysis, as described herein. In other examples, the assay (e.g., immunoassay, binding assay, etc.) may be used to determine the presence of or measure the molecule of interest (e.g., a protein, a nucleic acid molecule, a lipid, a carbohydrate, a metabolite, or a combination thereof) in each of the genetic variants and the genetic variants comprising the molecule of interest may be isolated and further analyzed.

Further analysis may be performed on selected biological variants (e.g., selected cells demonstrating the desired characteristic). Such analyses may include, without limitation, protein analysis (e.g., mass spectrometry, protein assays), nucleic acid analysis (e.g., sequencing such as next-generation sequencing (NGS)), lipid analysis (e.g., Raman scattering or spectroscopy), imaging (and image analysis), spectroscopy, or other analysis methods or screens, as described herein. Such analysis methods may be useful in determining the identity of the genetic variant, e.g., by yielding information on the DNA sequences or genes, amino acid sequence, protein properties (e.g., post-translational modifications). Such information may then be collected and stored in a database or reintegrated with the strain optimization library, optionally with any functional characteristics such as desired biological activity, phenotypic or metabolic trait, etc. Such further analysis may occur at any useful or convenient step. For example, in some instances, it may be beneficial to identify or characterize a set of biological variants (e.g., via sequencing, or other protein analysis) prior to determining the functional performance of the biological variants. In such instances, such characterization, e.g., sequencing (e.g., of a portion of a clonal population of cells) and optional indexing may be performed prior to screening the biological variants for the functional performance. Following screening of the functional performance, the sequences may be indexed or paired (e.g., using a computer readable medium) to the functional performance, thereby providing information on a correlation between structural (e.g., sequence) information and functional performance.

In some instances, the strain optimization unit may comprise or be coupled to a detector. The detector may be used to determine the presence or absence of a molecule of interest or a functional characteristic in a cell or reaction vessel, which may enable screening and/or selection of the desired biological variants. The detector may include one or more analytical instruments, e.g., a mass spectrometer, Raman spectrometer, near infrared (NIR) spectrophotometer, Fourier Transform Infrared (FTIR) spectrometer, a spectrophotometer (e.g., a fluorescence or absorbance plate or cuvette reader), a piezoelectric sensor, etc. The detector may be configured to count cells (e.g., a cell counter, a flow cytometer). The detector may comprise one or more optical components and may comprise, in some instances, a microscope (e.g., a stereoscope, a compound microscope, a fluorescent microscope, a polarizing microscope, a confocal microscope, a differential interference contrast microscope, a super-resolution microscope etc.), or components or combinations thereof. The detector may be used to detect a physical property of a cell or reaction vessel, including but not limited to: magnetism, impedance, topography or geometry, scattering, morphology, absorbance, fluorescence, color, clustering of cells, cell or colony size, etc. The detector may be a point detector or an array or image detector.

Movement actuators: In some instances, the reaction vessels are moved (e.g., toward the detector) using a reaction vessel movement actuator. The vessel movement actuator may be a fluid handling unit such as a robotic manipulator, a flow generator, an acoustic droplet generator, optical tweezers, a thermal drop-on-demand, a piezoelectric drop-on-demand, a lithography unit, a digital microfluidic device, dielectrophoresis, or a combination thereof. The movement actuator may comprise a stage and any necessary moving parts, e.g., screws, gears, threads, motors, pumps, compressors, resistors, transistors, springs, pulleys, etc. In some instances, the reaction vessels are placed on or adjacent to a substrate that is connected to a movement actuator.

Libraries: The strain optimization unit may comprise a strain optimization library, which may be used in the processes described herein. The strain optimization library can comprise a library of biological diversity; for instance, the strain optimization library may comprise a plurality of different biological variants, such as genetic variants. The plurality of genetic variants may be from a first strain. For instance, a first strain of cells (e.g., bacterial, yeast, animal, plant, etc.) cells may be subjected to conditions sufficient to generate the plurality of different genetic variants, such that each of the genetic variants is different. Each genetic variant of the plurality of genetic variants may comprise, for example, DNA or RNA that has a different sequence than other genetic variants of the plurality of genetic variants. The plurality of different genetic variants may encode for variations of the same biomolecule (e.g., DNA, RNA, peptides, proteins, etc.). For instance, the plurality of different genetic variants may include different DNA sequences that encode for variations in RNA sequences that are subsequently translated into proteins. Variations in the different DNA sequences in the library can result in different RNA sequences, which may encode for the same or different proteins. In some instances, the proteins encoded by the genetic variants (which may have variations in DNA and/or RNA) are enzymes. In such instances, the enzymes may form or be a part of a metabolic pathway. The enzymes or metabolic activity may be used as a screening parameter or performance requirement during the strain optimization process.

In some cases, the strain optimization unit is configured to screen the genetic variants and select for and/or classify the desired biological variants (e.g., genetic variants) based on a phenotypic or metabolic measurement. The phenotypic or metabolic measurement can include, in non-limiting examples: protein or enzymatic activity, protein expression levels, quantity of byproducts or metabolites, etc. For example, a desired biological variant may be one that has a defined or minimum-threshold enzymatic activity. In such cases, the genetic variants of the strain optimization library may be screened in the strain optimization unit, and only the genetic variants having the defined or minimum-threshold enzymatic activity are selected for further analysis. The genetic variants may be subjected to further analysis (e.g., sequencing, protein analysis) to determine the nucleic acid or protein sequence of the enzyme of interest. The determined sequence information (e.g., nucleic acid or protein sequence) and corresponding functional performance may be input into one or more computer readable medium (e.g., a simulator or model), which may subsequently be used for correlating structural elements (e.g., nucleic acid or protein sequences) with functional performance, as is described elsewhere herein. In some cases, the nucleic acid sequence may be recombined with other nucleic acid sequences exhibiting a desirable characteristic (e.g., the same or different enzyme activity), thereby generating a new library of genetic variants. The process can be repeated until the desired threshold of enzymatic activity is reached.

In some cases, the strain optimization library comprises genetic variants that are generated or synthesized. The plurality of genetic variants may be generated by one or more techniques. For example, the genetic variants may be generated by mutagenesis (e.g., random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), saturation mutagenesis, circular permutation), Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), a CRISPR guided DNA polymerase, contacting with a mutagen, conducting error-prone polymerase chain reaction (epPCR), or other genomic engineering approaches. In some instances, the strain optimization library is or comprises a whole-genome mutagenesis library, a genome-shuffled library, a targeted genomic library such as a promoter swap library, and a transposon library (e.g., promoter insertion library). In some embodiments, the targeted genomic library comprises one or more heterologous genetic elements. The heterologous genetic elements may comprise or encode for one or more members selected from the group consisting of promoters, 5' untranslated regions, 3' untranslated regions, ribozymes, RNA stability sequences, secretion peptides, fusion proteins, DNA binding domains, protein-protein binding regions, codon optimized genes, codon randomized genes, terminators, and non-homologous end joining. The strain optimization library may comprise genetic variants that are generated using targeted mutagenesis or non-targeted (e.g., random) mutagenesis. In some instances, the strain optimization library comprises a library of mutagenized cells.

The strain optimization library may comprise as many genetic variants as is useful for screening or optimizing a strain for the desired biological variant. The strain optimization library may comprise at least 100 genetic variants, at least 1,000 genetic variants, at least 10,000 genetic variants, at least 100,000 genetic variants, at least 1,000,000 genetic variants, at least 10,000,000 genetic variants, at least 100,000,000 genetic variants or more. As described herein, the strain optimization processes may be recursive or iterative. In such cases, the number of genetic variants screened per iteration may vary; for instance, the first cycle may screen 10,000,000 genetic variants while the second cycle screens 100,000 genetic variants. Conversely, the number of genetic variants may increase in between cycles, e.g., via introduction of new biological diversity or variants (e.g., new strains, new genetic variants, etc.) and/or conditional diversity (e.g., varying fermentation conditions for some or all of the newly introduced or screened biological variants).

Additional examples of systems and methods for strain optimization may be found, for example, in J. Agresti, et al. 2009. *"Ultrahigh-throughput screening in drop-based microfluidics for directed evolution."PNAS*, which is incorporated by reference herein in its entirety. See also, Examples 1, 4 and 5 below.

(ii) Molecule Discovery Unit

In some instances, the systems and methods disclosed herein utilize a molecule discovery unit, which may be useful in the discovery of novel molecules (e.g., biomolecules such as proteins, nucleic acids, etc.) that have a functional characteristic. The systems and methods described herein may involve high-throughput screening of libraries of variants, obtaining information or characterization of the variants, and then using the obtained information or characterization to design new molecules predicted to have a functional characteristic, in a high-throughput and consistent approach.

The molecule discovery unit can be useful in discovering novel molecules that have a desired functional characteristic. For instance, the molecule discovery unit may be configured to obtain or collect discovery molecules (e.g., DNA from a sample or library, or DNA information from a library) and screen the collected discovery molecules for a desired functional characteristic, such as a phenotypic or metabolic trait (e.g., enzymatic activity). The molecules displaying a desired functional characteristic may be isolated and characterized (e.g., using sequencing), thereby generating data on the discovery molecule and the functional characteristic (e.g., enzymatic activity level, expression of a target protein, etc.). The data may then be input into a computer-readable medium (e.g., a simulator or model) which may comprise a database and may be configured to predict structural-functional relationships of the discovery molecule, the expected performance of a given structure or sequence for a given set of application conditions, or other prediction based on the model inputs. In some embodiments, the computer-readable medium comprises a machine-learning algorithm.

The molecule discovery unit may comprise an experimental module, which may comprise a plurality of distinct molecule discovery reaction vessels, each with a different discovery molecule or application condition. In an example, a method for molecule discovery may comprise: (a) collecting or harvesting DNA sequences, (b) introducing the collected or harvested DNA sequences into a plurality of cells, (c) subjecting the plurality of cells with the collected or harvested DNA sequences to conditions sufficient for screening of the plurality of cells for a desired functional characteristic (e.g., phenotypic trait or metabolic trait), (d) isolating the cells that have the desired characteristic, and (e) determining the sequence of the isolated cells. The resulting data (e.g., sequencing reads or data) may be input into a computer readable medium (e.g., a simulator or model), which may be used to predict which sequences, regions, or motifs will have the desired functional characteristic. Optionally, the computer readable medium may be configured to compare the resulting data (e.g., sequencing reads or data) with a database of the same type of data (e.g., known sequences of a protein having the desired characteristic). One or more processes in the molecule discovery unit may be recursive or iterative. Alternatively or in addition to, multiple processes may be run in parallel and/or in series.

In another example, a method for molecule discovery may involve generating an improved cell by discovery of biological variants (e.g., genetic mutants) that lead to an improved functional performance of phenotype. Like strain optimization, such a method may comprise, for example, (a) generating a library of mutagenized cells, (b) partitioning the library of mutagenized cells into a plurality of partitions to yield partitioned mutagenized cells, (c) screening the partitioned mutagenized cells for a phenotype, and (d) based on the screening, selecting an improved cell from the partitioned mutagenized cells, and (e) using the improved cell to repeat (a)-(d). The molecule discovery process may be useful in screening molecular variants (e.g., a library of mutagenized cells) for a desired functional characteristic of phenotype, analyzing the molecular variants, and determining structural-functional relationships based on the observed phenotype and resulting analysis.

In an example, the molecule discovery unit may provide a structural functional relationship of genetic sequences to a phenotypic trait, e.g., production of a protein or catalytic activity of an enzyme. Such discovery may be achieved by performing multiple rounds of screening and enriching, optional addition of biological diversity (e.g., via mutagenesis) to generate new generations of biological variants, and conducting additional rounds of screening and enriching. For example, a library of mutagenized cells may be generated and optionally cultured under conditions sufficient to grow the cells. The library of mutagenized cells may then be partitioned into reaction vessels and optionally cultured under conditions sufficient to grow or expand the cells (e.g., under a defined set or sets of fermentation conditions, in liquid culture, etc.). In some instances, individual cells may be partitioned into the individual reaction vessels. Such partitioning may be assisted by a computer readable medium and feedback control, as is described elsewhere herein. Subsequently, the partitioned cells may be subjected to screening, and based on the screening, the cells that have a desired functional characteristic (e.g., a desired phenotype) may be enriched (e.g., isolated, collected, or selected). These enriched cells may be subjected to additional rounds of enrichment (e.g., re-partitioned, cultured, screened, and enriched). After a defined (e.g., user-determined or computer-guided decision) number of rounds of enrichment, the enriched cells may be further analyzed (e.g., via sequencing) to identify the genetic variants (e.g., using the nucleic acid or gene sequence).

In some instances, a structural-functional relationship may be determined by calculating, e.g., using a computer readable medium, an enrichment factor. The enrichment factor may be or comprise, for example, a comparison, such as a difference or ratio, of the amount of product produced from a sorted, enriched cell as compared to another cell, e.g., an unsorted or un-enriched cell, a wild-type cell, a parent cell, etc. In some instances, the enrichment factor may comprise a ratio of the occurrence of a variant (e.g., genetic variant) in a population of sorted cells as compared to the un-sorted population. The enrichment factor may act as a proxy for a functional performance (e.g., a functional performance). In parallel, sequence information may be obtained from the enriched cells (e.g., those that result in the highest functional performance) to determine the gene sequence and/or genomic mutations. The identified gene sequences (or genomic mutations) may then be assigned or paired to the enrichment factor, thereby generating a structural-functional relationship of the gene sequence to a functional characteristic.

In some instances, the enrichment factor may be or comprise a comparison of the number of appearances of a variant (e.g., a genetic variant) in an unsorted sample as compared to a sorted sample. For example, the abundance of each genetic variant (e.g., as identified using sequencing) may be determined in an unsorted population of cells as well as the sorted enriched cells, and the enrichment factor may be calculated by taking the ratio or difference of the abundance of the genetic variant in the enriched cells over the abundance of the genetic variant in the unsorted or un-enriched cells. In such an example, the unsorted sample, or portion thereof, may be subjected to sequencing to identify the genetic variants within the unsorted sample, and an abundance of a particular genetic variant may be computed, e.g., by determining the number of occurrences of the particular genetic variant out of all the genetic variants in the unsorted sample. Similarly, the sorted sample, or portion thereof, may be subjected to sequencing to identify the genetic variants within the sorted sample, and an abundance of the particular genetic variant may be computed, e.g., by determining the number of occurrences of the particular genetic variant out of all the genetic variants in the sorted sample. The abundance of the particular genetic variant in the unsorted sample as compared to the sorted sample may indicate the enrichment of that particular genetic variant from the enrichment process. For example, for a particular genetic variant X, which appears 10 times out of 100,000 sequences (or at a frequency of 1:10,000) in the unsorted sample and which appears 1 out of 100 sequences in the sorted sample, the enrichment factor is (1/100)/(1/10,000), or 100-fold. The enrichment factor may be useful as a proxy or estimate of the change in functional performance (e.g., amount of product produced or an activity level of a protein or enzyme). Alternatively, the enrichment factor may be calculated by the number of occurrences of the genetic variant in the sorted sample as compared to the unsorted example. It will be appreciated that the enrichment factor may compare the number of appearances of a variant in a sorted or enriched sample as compared to (i) an unsorted sample or (ii) a sample obtained from a previous round of enrichment.

The enrichment factor may be, in some instances, about 1, about 2, about 3, about 4, about 5, about 6, about 7, about 8, about 9, about 10, about 20, about 30, about 40, about 50, about 100, about 500, about 1000, about 10,000, about 100,000, about 1,000,000, about 10,000,000 fold or greater. The enrichment factor may fall in a range, e.g., from about 10-fold to about 100-fold, from about 100-fold to about 1,000-fold, etc.

In some instances, the molecule discovery processes may not involve cells and may involve collecting or harvesting different discovery molecules, subjecting them to one or more application conditions, and isolating the molecule variants that have the desired characteristic. Further characterization (e.g., chemical or biochemical analysis) of the different discovery molecules may be performed. For example, the discovery molecules having the desired characteristic (e.g., metabolic activity, exhibiting a desired physical or chemical property) may be subjected to chemical or elemental analysis such as imaging (and image analysis), spectroscopy, mass spectrometry, gravimetry, atomic spectroscopy, nuclear magnetic resonance (NMR), chromatography, plasma mass spectrometry, X-ray photoelectron spectroscopy (XPS), Auger electron spectroscopy, etc. The resulting data (e.g., chemical composition, physical properties, etc.) may be used to predict which structural elements (e.g., elements, chemical compositions, etc.) will have the desired functional characteristic.

The molecule discovery unit may be used to discover new molecules (e.g., biomolecules such as proteins or peptides) by way of introducing a library of molecules (e.g., genetic library comprising a plurality of genetic variants or DNA sequences that encode for different target proteins or a molecule library comprising a plurality of molecular variants that encode for different proteins or effect a functional characteristic) into a cell or population of cells, optionally culturing the cells under one or more application conditions, and screening the cells for the desired functional characteristic. The cell or population of cells that exhibit the desired functional characteristic (e.g., expression of a particular target protein under a specified application condition, or other phenotypic or metabolic trait) may be isolated and further processed or analyzed (e.g., using sequencing). Iterative or recursive cycles of such processes may be useful in generating large volumes of data pertaining to a molecule's chemical or structural composition (e.g., protein motifs, DNA or amino acid sequences) and function or performance (e.g., having the desired characteristic, phenotype, metabolic trait, etc.) for a given set of application conditions. In some instances, additional input of biological diversity (e.g., via recombination of genes and introduction of recombined genes in cells or via mutagenesis) may be introduced during the recursive cycle. Alternatively or in addition to, the condition diversity (e.g., change in application or culture conditions) may be introduced during the recursive cycle.

In some instances, it may be useful to screen a variety of application conditions using the molecule discovery unit. In such cases, the reaction vessels, optionally comprising molecular variations (which may be naturally occurring or induced, as described herein) may be subjected to different application conditions. Non-limiting examples of different application conditions include: temperature, growth or nutrition medium composition, reaction buffer composition, substrate concentration, oxygenation, salinity, pH, carbon source, buffer concentration, duration of culture, matrix composition, protein concentration, attachment or immobilization of a molecule or variant to a support (e.g., bead or other solid support), and aeration. For example, in the case of molecule discovery in or using a plurality of cells, the plurality of cells can be cultured under a defined set of fermentation conditions prior to partitioning the cells in reaction vessels, or the cells may be cultured with the defined fermentation condition in the reaction vessel. The fermentation conditions may be the same or different across a subset or all of the reaction vessels. In another example, the plurality of cells may be subjected to an application condition comprising a treatment (e.g., drug or small molecule treatment, presence of a substrate, varying reaction conditions, etc.) which may affect the performance or desired characteristic (e.g., expression level of the protein target, enzymatic activity level) of the plurality of cells. Varying the application conditions and observing the effect on performance of the plurality of cells can be useful in understanding how environmental perturbations affect structure or function and/or may be used in the discovery of new or optimized molecules having a desired characteristic under the given application conditions.

In the case of biomolecule discovery in or using cells, the cultured cells may be screened in the reaction vessels of the molecule discovery unit, and the cells that have a desired functional characteristic (e.g., expression of a target protein variant, enzymatic activity, metabolic or phenotypic trait) under the defined application conditions may be isolated, collected, and analyzed (e.g., via sequencing) to identify the genetic or protein variant (e.g., using the nucleic acid or amino acid sequence). The genetic or protein variants that have the desired characteristic (e.g., expression of a target protein under a specified application condition, or other phenotypic or metabolic trait) may be isolated. Information on the genetic or protein variant (e.g., the nucleic acid or amino acid sequences) and the corresponding performance (e.g., target protein expression levels) may be generated. The processes may be iterated in a recursive cycle such that each cycle generates data on a structural or sequence element and the corresponding performance. In some instances, additional input of biological diversity (e.g., via recombination of genes and introduction of recombined genes in cells or via mutagenesis) may be introduced during the recursive cycle, thereby generating additional data on structural or sequence element and the effects of such structural or sequence elements on the performance. Alternatively or in addition to, the condition diversity (e.g., change in application conditions) may be introduced during the recursive cycle.

The different discovery molecules may be comprised in a library (e.g., a protein library, a peptide library, a biomolecule library) or the different discovery molecules may be encoded for in a genomic variant library, which may comprise genetic variants from that are naturally occurring or that are generated or synthesized. For example, naturally occurring genetic libraries may comprise DNA sequences gathered from a sample (e.g., a biological sample, a soil sample, etc.) and may constitute or comprise an environmental DNA (eDNA) library. In other instances, the library may comprise genetic variants that are synthesized. For example, the genetic variants may be generated by mutagenesis (e.g., random mutagenesis (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), saturation mutagenesis, circular permutation), Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), a CRISPR guided DNA polymerase, error prone polymerase chain reaction (epPCR) or other genomic engineering approaches. In some instances, the genomic variant library is or comprises a whole-genome mutagenesis library, a genome-shuffled library, a targeted genomic library such as a promoter swap library, and a transposon library (e.g., promoter insertion library). In some instances, the targeted genomic library comprises or encodes for one or more members selected from the group consisting of promoters, 5' untranslated regions, 3' untranslated regions, ribozymes, RNA stability sequences, secretion peptides, fusion proteins, DNA binding domains, protein-protein binding regions, codon optimized genes, codon randomized genes, terminators, and non-homologous end joining. In some instances, the genomic variant library may be a single gene random mutation library, a site saturation library (e.g., a protein or peptide library in which every amino acid is mutated, at each site, to each of the 20 amino acids), a small-insert metagenomic library, a large-insert metagenomic library, or a combination of approaches. In some instances, the different discovery molecules are DNA-encoded molecules. The DNA-encoded molecules may be comprised in a library, such as a metagenomic library, a DNA-encoded library, a library from one or more organisms, or a Function Generator-created library. The DNA-encoded molecule library may comprise randomly-generated DNA-encoded molecules, naturally-occurring DNA-encoded molecules, or a combination thereof.

As with the strain optimization unit, multiple experimental conditions may be screened simultaneously using the systems and methods described herein. For instance, the molecule discovery unit may be configured to simultaneously screen or analyze millions of reaction volumes comprising different discovery molecules or molecular variants that have been subjected to the same or different application conditions. Beneficially, the molecule discovery unit may provide multiplexed, multiparametric information on molecular variants and environmental (or application) conditions of the molecular variants (also referred to herein as "discovery molecules"). Additionally, the molecular discovery unit may be beneficial in discovering new molecules (e.g., proteins encoded by DNA) having a desired performance criterion, e.g., a molecule having the desired characteristic such as a threshold enzymatic activity level or other metabolic or phenotypic trait or production of a target protein under a particular application condition.

Reaction vessels: The reaction vessels of the molecule discovery unit may be, for instance, droplets or plugs, wells (e.g., microwells, nanowells, picowells, etc.), vials, tubes, flasks, or other container. In some instances, the reaction vessels are comprised in a microfluidic device, which may comprise or be a portion of a consumable unit. In some instances, the reaction vessels are a member of an array, e.g., a microwell array or plate, a nanowell array or plate, etc. Multiple types of reaction vessels may be used (e.g., droplets and wells) for any of the processes described herein, either simultaneously or sequentially. The reaction vessels may be physically distinct or discrete, or the reaction vessels may be capable of being merged or coalesced.

Each reaction vessel can comprise a different discovery molecule for screening. For example, as with the strain optimization unit, it may be useful to screen a library of genetic variants encoding for different proteins for a desired functional characteristic (e.g., biomolecular (e.g., enzymatic) activity, biomolecule interaction, phenotypic or metabolic trait); accordingly, each reaction vessel may be configured to contain a different genetic variant for screening. In some cases, each reaction vessel comprises one or more cells having the genetic variant. For example, each reaction vessel may comprise a single cell or more than one cell having a single genetic variant that is different than the genetic variants of other cells in other reaction vessels. Alternatively or in addition to, each reaction vessel may comprise a clonal population of cells with a single genetic variant. In other examples, it may be useful to screen different genetic variants within a single reaction vessel; accordingly a reaction vessel may comprise a mixture of cells with different genetic variants. In such an example, each reaction vessel may comprise a combination of cells and genetic variants.

As described above, the reaction vessels may comprise a single cell or multiple cells and may be configured to be assessed in a high-throughput manner. For instance, the molecule discovery unit may be configured to screen at least 100 cells/min, at least 500 cells/min, at least 1,000 cells/min, at least 5,000 cells/min, at least 10,000 cells/min, at least 50,000 cells/min, at least 100,000 cells/min. Alternatively or in addition to, the reaction vessels may be screened in a high-throughput manner. For instance, the molecule discovery unit may be configured to screen at least 10 reaction vessels/min, at least 100 reaction vessels/min, at least 500 reaction vessels/min, at least 1,000 reaction vessels/min, at least 5,000 reaction vessels/min, at least 10,000 reaction vessels/min, at least 50,000 reaction vessels/min, at least 100,000 reaction vessels/min. In some instances, the molecule discovery unit may be configured to screen at least 10 reaction volumes/min, at least 100 reaction volumes/min, at least 500 reaction volumes/min, at least 1,000 reaction volumes/min, at least 5,000 reaction volumes/min, at least 10,000 reaction volumes/min, at least 50,000 reaction volumes/min, at least 100,000 reaction volumes/min.

Any number of reaction vessels may be generated or used within a given duration. In some instances, it may be beneficial to screen different numbers of reaction vessels (or volumes). Accordingly, the number of reaction vessels (or volumes) used or generated may be adjusted according to the suitable application or experimental purpose. For instance, when large numbers of discrete reaction volumes are useful e.g., for screening purposes (e.g., for molecule discovery), at least 10,000 reaction volumes, at least 100,000 reaction volumes, at least 1,000,000 reaction volumes, at least 10,000,000 reaction volumes, at least 100,000,000 reaction volumes or more reaction volumes may be used. In other instances, smaller numbers of discrete reaction volumes may be useful or required (e.g., for a targeted screen or for rational design of experiments with a limited number of species for screening). In such instances, at most 100,000,000 reaction volumes, at most 10,000,000 reaction volumes, at most 1,000,000 reaction volumes, at most 100,000 reaction volumes, at most 10,000 reaction volumes, at most 1,000 reaction volumes or fewer may be used or generated.

Similar to the strain optimization unit, the reaction vessels of the molecule discovery unit may be comprised within a microfluidic device and may accommodate any useful volume. In the case of droplets, the droplets may comprise any useful composition, as described above.

Assays: In some instances, the sorting of the biological variants may comprise the use of one or more screening operations. The screening operation may include an assay, e.g., a direct assay, an indirect assay, a binding assay, a reporter assay (e.g., reporter cell-based assay), a fluorogenic assay, a chromogenic or colorimetric assay, etc. One or more immunological assays may be used, including, but not limited to: enzyme-linked immunosorbent assay (ELISA), sandwich ELISA, proximity ligation assay, etc. In some instances, a reporter molecule or selection molecule is used for screening. The assay or reporter or selection molecules may be useful in the detection of the presence of a genetic variant or a functional characteristic (e.g., phenotypic or metabolic trait) of the biological variant. For example, in cases where the desired biological variant is a cell that comprises enzymatic activity, the cells in the reaction vessels may be screened in the presence of a detection reagent, e.g., a chromogenic or fluorogenic substrate that changes color, fluoresces, or otherwise changes the surrounding environment upon conversion of the substrate to a product by the desired enzymatic activity. In such an example, the reaction vessels that exhibit a change in color or fluorescence may indicate that the cell comprises the desired enzymatic activity; subsequently that cell may be isolated and further analyzed (e.g., via sequencing, protein analysis, etc.) to determine information on the biological variant (e.g., DNA or RNA sequence, protein sequence or composition, etc.). In other examples, the desired biological variants may comprise a selection or reporter molecule; for example, in the case of selection molecules, only cells with the desired trait may survive in a given culture condition (e.g., only cells with transgenes or recombinant genes that encompass antibiotic resistance will survive in a growth medium comprising antibiotics). The surviving cells may be screened for the desired functional characteristic and those that have the desired functional characteristic may be subjected to further analysis. In yet another example, only cells with the desired trait may express a reporter molecule (e.g., fluorescent or detectable protein) indicating that a transgene or recombinant gene is present. In such examples, cells exhibiting a desirable trait or functional characteristic may be isolated from the reaction vessel and subjected to further analysis, as described herein. In other examples, the assay (e.g., immunoassay, binding assay, etc.) may be used to determine the presence of the molecule of interest (e.g., a protein, a nucleic acid molecule, a lipid, a carbohydrate, a metabolite, or a combination thereof) in each of the genetic variants and the genetic variants comprising the molecule of interest may be isolated and further analyzed. For example, the assay may include the addition of one or more detection reagents, e.g., a pH-modifying agent, an ionic strength or ion concentration-modifying agent, an ion, a substrate, an inhibitor, an enzyme, or a competitor.

The one or more screening operations may comprise imaging or detection of a signal in the reaction vessels. For example, in cases where the desired biological variant is a cell that comprises enzymatic activity, the cells in the reaction vessels may be imaged in the presence of a detection reagent, e.g., a chromogenic or fluorogenic substrate that changes color, fluoresces, or otherwise changes the surrounding environment upon conversion of the substrate to a product by the desired enzymatic activity. The obtained images may be analyzed by a computer readable medium, e.g., to obtain a signal intensity value. Based on the result of the imaging, the components of the strain optimization unit may be configured to automatically sort a cell or a reaction vessel, e.g., by moving the cell or reaction vessel to a different location. Imaging may be performed at any useful or convenient step, e.g., before, during, or following partitioning, culturing (if applicable), screening, sorting, etc.

Further analysis may be performed on selected biological variants (e.g., selected cells demonstrating the desired characteristic). Such analyses may include, without limitation, protein analysis (e.g., mass spectrometry, protein assays), nucleic acid analysis (e.g., sequencing), lipid analysis (e.g., Raman scattering or spectroscopy), imaging (and image analysis), spectroscopy, chemical composition analysis (e.g., NMR, XPS, chromatography, etc.) or other analysis methods or screens, as described herein. Such analysis methods may be useful in determining the identity of the genetic variant, e.g., by yielding information on the DNA sequences or genes, amino acid sequence, protein properties (e.g., post-translational modifications). Such information may then be collected and stored in a database or reintegrated with the molecule discovery library, optionally with any functional characteristics such as desired biological activity, phenotypic or metabolic trait, etc.

In some instances, the molecule discovery unit may comprise or be coupled to a detector. The detector may be used to determine the presence or absence of a molecule of interest or a functional characteristic in a cell or reaction vessel, which may enable screening and/or selection of the desired biological variants. The detector may include one or more analytical instruments, e.g., a mass spectrometer, Raman spectrometer, near infrared (NIR) spectrophotometer, Fourier Transform Infrared (FTIR) spectrometer, a spectrophotometer (e.g., a fluorescence or absorbance plate or cuvette reader), a piezoelectric sensor, etc. The detector may be configured to count cells (e.g., a cell counter, a flow cytometer). The detector may comprise one or more optical components and may comprise, in some instances, a microscope (e.g., a stereoscope, a compound microscope, a fluorescent microscope, a polarizing microscope, a confocal microscope, a differential interference contrast microscope, a super-resolution microscope etc.), or components or combinations thereof. The detector may be used to detect a physical property of a cell or reaction vessel, including but not limited to: magnetism, impedance, topography or geometry, scattering, morphology, absorbance, fluorescence, color, clustering of cells, cell or colony size, etc. The detector may be a point detector or an array or image detector. The detector may be configured to collect a signal of a point, an array, and generate a point measurement or image.

Movement Actuator: In some instances, the reaction vessels are moved (e.g., toward the detector) using a reaction vessel movement actuator. The vessel movement actuator may be a robotic manipulator, a flow generator, an acoustic droplet generator, optical tweezers, a thermal drop-on-demand, a piezoelectric drop-on-demand, a lithography unit, a digital microfluidic device, or a combination thereof. The movement actuator may comprise a stage and any necessary moving parts, e.g., screws, gears, threads, motors, pumps, compressors, resistors, transistors, springs, pulleys, etc. In some instances, the reaction vessels are placed on or adjacent to a substrate that is connected to a movement actuator.

Molecule libraries: The molecule discovery unit may comprise a discovery molecule library, which may be used in the processes described herein. The molecule discovery library can comprise a plurality of different genetic variants, as described herein. The plurality of genetic variants may be from a first strain. For instance, a first strain of cells (e.g., bacterial, yeast, animal, plant, etc.) cells may be subjected to conditions sufficient to generate the plurality of different genetic variants (e.g., via targeted or non-targeted mutagenesis), such that each of the genetic variants is different. Each genetic variant of the plurality of genetic variants may comprise, for example, DNA or RNA that has a different sequence than other genetic variants of the plurality of genetic variants. The plurality of different genetic variants may encode for variations of the same biomolecule (e.g., DNA, RNA, peptides, proteins, etc.). For instance, the plurality of different genetic variants may include different DNA sequences that encode for variations in RNA sequences that are subsequently translated into proteins. Variations in the different DNA sequences in the library can result in different RNA sequences and thus translated proteins or peptides. In some instances, the proteins or peptides encoded by the genetic variants (which may have variations in DNA and/or RNA) are enzymes. In such instances, the enzymes may form or be a part of a metabolic pathway. The enzymes or metabolic activity may be used as a screening parameter or performance requirement during the molecule discovery process.

In some cases, the molecule discovery unit is configured to screen the molecular variants and select for and/or classify the desired biological variants (e.g., molecular variants) based on a functional characteristic (e.g., phenotypic or metabolic trait or activity) or measurement. For example, a phenotypic or metabolic measurement can include, in non-limiting examples: protein or enzymatic activity, protein expression levels, quantity or amount of byproducts or metabolites, etc. For instance, a desired biological variant may be one that has a defined or minimum-threshold enzymatic activity. In such cases, the molecular variants of the molecule discovery library may be screened in the molecule discovery unit, and only the molecular variants having the defined or minimum-threshold enzymatic activity are selected for further analysis. The molecular variants may be subjected to further analysis (e.g., sequencing, protein analysis, chemical analysis) to determine the nucleic acid or protein sequence or chemical composition of the enzyme of interest. In some instances, the sequence or composition of the molecular variant is added to a database and/or reintegrated in the molecule discovery library with the functional properties or performance. As such, the molecule discovery unit may be useful in correlating sequence or structural information with functional properties or performance, or for uncovering noncanonical structural-functional relationships, e.g., discovering sequences with higher diversity or less homology that have similar functional performance under a given set of conditions.

The molecule discovery library may comprise as many molecular variants as is useful for screening or discovering molecules having or effecting a desired functional characteristic. The molecule discovery library may comprise at least 100 different discovery molecules, at least 1,000 different discovery molecules, at least 10,000 different discovery molecules, at least 100,000 different discovery molecules, at least 1,000,000 different discovery molecules, at least 10,000,000 different discovery molecules, at least 100,000,000 different discovery molecules or more. As described herein, the molecule discovery processes or the integrated system may be recursive or iterative. In such cases, the number of different discovery molecules screened per iteration may vary; for instance, the first cycle may screen 10,000,000 different discovery molecules while the second cycle screens 100,000 different discovery molecules. Conversely, the number of different discovery molecules may increase in between cycles, e.g., via introduction of new biological diversity or variants (e.g., new strains, new different discovery molecules, etc.) and/or conditional diversity (e.g., varying fermentation conditions for some or all of the newly introduced or screened biological variants).

(iii) Molecule Optimization Unit

In some instances, the systems and methods disclosed herein utilize a molecule optimization unit, which may be useful in screening and optimizing a molecule (e.g., protein, peptide, or other biomolecule) for a functional characteristic. The systems and methods described herein may employ the use of one or more machine learning algorithms that inputs information or data on a library of variant and outputs designed variants configured to perform a function in an improved manner.

The molecule optimization unit can be useful in screening molecular variants for a desired functional characteristic and predicting structural-functional relationships of molecules (e.g., biomolecules or polymers, e.g., biopolymers such as proteins, peptides, nucleic acid sequences, etc.) as well as for optimizing a desired functional characteristic by manipulating the structure of a molecule. In an example, a method for molecule optimization may comprise: (a) obtaining structural (e.g., sequence information) and functional performance data for a molecule (e.g., protein, enzyme), and (b) using a computer readable medium to generate a prediction on a structure of an optimized molecule having a functional performance at or above a threshold performance criterion. In some instances, the method may further comprise (c) introducing the predicted structure into a library of variants (e.g., genetic variants, which may comprise recombinant genes or transgenes comprising gene sequences pertaining to the desired functional characteristic or that encode for a target protein) and (d) screening the library of variants, which may, in some instances, be iterative. In some instances, the method includes using a computer-readable medium (e.g., a model, simulator) to predict a structure (e.g., gene sequence or amino acid sequence, chemical composition, etc.) for an optimized molecule having a desired functional characteristic above a performance criterion threshold. In some instances, the computer-readable medium comprises a machine learning algorithm.

In another example, a method for molecule optimization may comprise: (a) providing a library of molecule or strain variants (e.g., DNA-encoded library that encodes for one or more peptides or proteins, nucleic acid molecules that have functional performances (e.g., aptamers), a library of cells comprising molecule (e.g., polymer or peptide) variants) and (b) screening the library of variants, which may, in some instances, be iterative. The screening may involve selecting the variants that have a desired functional characteristic or meet a functional performance criterion. For instance, in the case of proteins or peptides, an enzymatic activity or binding property may be monitored and those with the desired enzymatic activity or binding property may be selected and optionally further optimized.

In some instances, the molecule optimization unit comprises a computational component (e.g., a computer readable medium) that inputs one or more data sets and outputs a prediction of structural-functional relationship of a molecule or a structure (e.g., sequence, motif, chemical composition, etc.) that is predicted to yield a desired functional characteristic. The data sets may include outputs from the other integrated units (e.g., molecule discovery unit, strain optimization unit). For example, data from the strain optimization unit, such as which fermentation conditions and genetic variants yield a desired functional characteristic, may be used in the molecule optimization unit to generate the prediction. Similarly, data from the molecule discovery unit, such as the sequences or structural information of molecules with a desired functional characteristic, the material or biological origin, the application conditions, etc., may be used in the molecule optimization unit. Conversely, data from the molecule optimization unit may be used in the strain optimization unit or molecule discovery unit for the strain optimization processes and molecule discovery processes, respectively.

In some instances, the data sets which are input into the molecule optimization unit include data from databases, such as publicly available databases. For example, in the case of protein or peptide optimization, protein information from databases such as DDBJ, GeneCards, InterPro, NCBI, POWL, PIR, PRF, SYSTERs, 3Dee, ArchDB, ASTRAL, BioMagResBank, CDDB, EMDataBank, Enzyme Structures, fPOP, Jena Lib, PMP, Proteopedia, MolMovDB, PDB, PISA, PMP, SBKB, TOPSAN, COG, Pfam, PRINTS, iProClass, ProDom, PROSITE, SMART, AutoPSI, CATH, CDD, CE, CL, FSSP, HOMSTRAD, MODBASE, PartsList, PDBe, SCOP, VAST, AARSDB, ASD, ASPD, BRENDA, DAVID, Catalytic Site Atlas, EF-hand CaBP, EcoCyc, ENZYME, Gene Ontology, GPRCD, Homeobox, KEGG, MatrixDB, MEROPS, MetaCyc, P2CS, PREX, Protein Kinase Resource, Protein Ontology, RNase P, SuperCYP, Transport DB, CPLA, P3DB, Phospho3D, PHOSIDA, LOCATE, eSLDB, LOCATE, NPD, NURSA, ORGe, PSORTdb, SUBA, 3dID, UniProt, GenBank, RefSeq, SwissProt, Protein, MEDLINE, BioSystems, Entrez, SRS, SCOPPI, ReLiBase, Protein3dHome, MIPS, IBIS, DOMMINO, DOMINE, DIP, DIMA, BioGRID, and the like may be used.

In some instances, both empirical data and data from databases are used in the molecule optimization unit. The data from the databases (e.g., sequence information, structural-functional relationships, protein-protein interactions) may be used in conjunction with the empirical data (e.g., from the other integrated units or from the molecule optimization unit) to predict a molecular variant that is expected to have the desired functional characteristic or a certain threshold level of functional performance. The predicted molecular variants may then be screened in the molecule optimization unit or other integrated units (e.g., strain optimization unit or molecule discovery unit).

In one non-limiting example, data from the molecule discovery unit or the strain optimization unit comprising structural or sequence data, e.g., the DNA sequence encoding for an enzyme of interest or the amino acid sequence of the enzyme in a desired biological variant, as well as the performance of the enzyme (from one or more recursive cycles), and/or the fermentation or application conditions may be input into the molecule optimization unit (e.g., a computational component or computer readable medium of the molecule discovery unit). Data from one or more protein or enzyme databases (e.g., UniProt, DDBJ, etc.) may be also be added to the molecule optimization unit (e.g., the computational component or computer readable medium). The computer readable medium of the molecule optimization unit may comprise one or more algorithms which may use the inputs and output a model or prediction on which parameters (e.g., structure, sequence, application conditions, fermentation conditions, etc.) affect performance (e.g., enzymatic activity). The computer readable medium may also output a prediction on which parameters (e.g., gene sequences or variants, fermentation conditions) are likely to result in a performance at or greater than the threshold performance criterion (e.g., baseline activity level).

In some instances, the predicted gene variants may be built into gene libraries such as plasmid libraries, e.g., via recombination strategies such as restriction digestion, sequencing-by-synthesis, etc. or by mutagenesis, (e.g., exposure to mutagens such as ultraviolet radiation, ethyl methyl sulfonate, etc.) as described elsewhere herein. The gene libraries may then be introduced into one or more cells, e.g., via transfection, transformation, or transduction, thereby generating a plurality of cells comprising genetic variants. The plurality of cells may optionally be cultured under one or more application or fermentation conditions. The plurality of cells may be screened for a desired functional characteristic or performance (e.g., enzymatic activity) in a high-throughput format, as described elsewhere herein. The strains exhibiting the desired functional characteristic or performance may be isolated and subjected to further analysis (e.g., sequencing) to identify the genetic variant. This information or data (e.g., functional performance and gene sequence) may then be re-input into the computer readable medium (e.g., simulation or model) to further refine the prediction quality. Such processes, similar to those presented in strain optimization, may be performed iteratively or recursively until a desired performance criterion is met.

The molecule optimization unit may comprise an experimental module, which may comprise a plurality of distinct molecule optimization reaction vessels, each with a different target protein (or molecular variant) or application condition. As described herein, a method for molecule optimization may comprise obtaining structural (e.g., sequence information) and functional performance data for a molecule (e.g., protein, enzyme), generating a prediction on a structure of an optimized molecule having a functional performance at or above a threshold performance criterion, introducing the predicted structure into a library of variants (e.g., genetic variants, which may comprise recombinant genes or transgenes comprising gene sequences pertaining to the desired functional characteristic) and screening the library of variants, which may, in some instances, be iterative. In some instances, a method for molecule optimization may comprise obtaining a library of variants (e.g., gene variants generated from randomly mutating genes or operons) and screening the library of variants for a desired functional performance or characteristic. In some instances, one or more operations may be iterative. As such, the molecule optimization unit may comprise systems for processing large numbers of reaction vessels.

By way of example, the molecule optimization unit may be used, similarly to the strain optimization unit, for directed evolution approaches and engineering of a cell or population of cells to have a desired functional characteristic. In such an example, biological variants, such as a library of cells comprising one or more polymer variants or a plurality of cells having genetic variations (which may be naturally occurring or induced, e.g., via mutagenesis or transformation, transduction, of a transgene or recombinant gene, etc.), may be screened in the reaction vessels of the molecule optimization unit, optionally under a plurality of application conditions, and the cells that have a desired functional characteristic may be sorted, isolated, collected, and/or analyzed (e.g., via sequencing). The functional characteristic (e.g., production of a molecule of interest, activity level of the molecule of interest) may be measured using imaging or an assay, as described herein, and may be performed prior to, during, or following the screening. In some instances, a portion of the library of biological variants may not be sorted or may be sorted to a different location than that of the biological variants demonstrating the preferred functional characteristic. For example, a sample may comprise the library of biological variants, and a portion of the sample may be sorted, while a portion remains unsorted. The unsorted (or differently sorted) biological variants may serve as a control population or as a control group to compare or measure the increase or enhancement of the functional characteristic from the molecule optimization process. In some instances, the sorted cells may be directed to another number of bins, such that a plurality of cell groups is obtained. For example, gating may be performed and the cells exhibiting the highest functional performance may be directed to a first group, the cells exhibiting the second highest performance may be directed to a second group, etc.

The sorted cells may be subjected to further characterization or analysis. The analysis of the biological variants may comprise identification of the genetic variants (e.g., optionally purifying and sequencing to determine the nucleic acid or gene sequence). Similarly, the unsorted or differently sorted cells may also be subjected to further characterization, e.g., to obtain sequence information or data. In some instances, the sequence information may be paired or correlated with the functional characteristic. In one example, the sequence information may be paired, e.g. using a computer readable medium, with the functional characteristic based on an abundance of the sequence (e.g., a sequence count) in the sorted and unsorted cells. Alternatively or in addition to, the abundance of each polymer variant may be obtained in both the sorted and unsorted cells. From the sequence and abundance data, enrichment data (e.g., an enrichment factor) may be obtained, e.g., by comparing the abundance of each polymer variant in the sorted cells to the abundance of each polymer variant in the unsorted cells. The function data, sequence data, and enrichment data may individually or collectively be input into a computer readable medium (e.g., a machine learning algorithm) to then design and output a predicted variant expected to have an improved functional characteristic.

In some instances, a library of variants may comprise one or more fiducial markers or sequences which may be used for sorting. For example, the sample or library of variants may be sorted based on a function of the polymer variants, and at least one of the polymer variants comprises a fiducial sequence. The fiducial sequence may be used to calibrate the measurements; for example, the fiducial sequence may comprise a known sequence and a known functional activity, which can be used to calibrate or normalize the screening process to the known functional activity. The fiducial sequences may comprise one or more biological variants that may encode for the same or a different polymer. For example, two fiducial sequences may comprise different DNA sequences that encode for the same polymer (e.g., peptide or protein).

In some instances, the biological variants that have the desired characteristic (e.g., a gene of interest, expression of a protein under a specified fermentation condition, or other phenotypic or metabolic trait) may be isolated and recombined into a plurality of recombinant genes and re-screened, e.g., via transformation, transfection, or transduction of the recombinant genes into cells, optionally culturing the cells, and isolating the cells with the desired functional characteristic, optionally with a more stringent performance requirement. The processes may be iterated in a recursive cycle such that each cycle has a more stringent performance requirement (e.g., a higher or lower metabolic activity, enzymatic activity, or higher or lower expression of a phenotypic trait). The recursive cycle and operations contained therein may be performed for as many cycles as necessary for a desired performance requirement to be met. In some instances, additional input of biological diversity (e.g., via recombination of genes and introduction of recombined genes in cells or via mutagenesis) may be introduced during the recursive cycle. Alternatively or in addition to, the condition diversity (e.g., change in application conditions) may be introduced during the recursive cycle.

In some instances, it may be useful to perform a conditional diversity screen, e.g., screening a variety of application conditions, using the molecule optimization unit. In such cases, the reaction vessels or molecular variants may be subjected to different application conditions, optionally comprising molecular variations (which may be naturally occurring or induced, as described herein) may be subjected to different application conditions. Non-limiting examples of different application conditions include: temperature, growth or nutrition medium composition, reaction buffer composition, substrate concentration, oxygenation, salinity, pH, carbon source, buffer concentration, duration of culture, feeding schedule, and aeration. For example, in the case of molecule optimization in or using a plurality of cells, the plurality of cells can be cultured under a defined set of fermentation conditions prior to partitioning the cells in reaction vessels, or the cells may be cultured with the defined fermentation condition in the reaction vessel. The fermentation conditions may be the same or different across a subset or all of the reaction vessels. In another example, the plurality of reaction vessels (optionally comprising cells) may be subjected to an application condition comprising a treatment (e.g., drug or small molecule treatment, presence of a substrate, varying reaction conditions, etc.) which may affect the performance or desired characteristic (e.g., expression level of the protein target, enzymatic activity level) of the plurality of reaction vessels. Varying the application conditions and observing the effect on performance of the molecules can be useful in understanding how environmental perturbations affect structure or function and/or may additionally be used in the discovery of new or optimized molecules (e.g., target proteins or other biomolecules) having a desired characteristic under the given application conditions.

In some instances, the molecule optimization processes does not involve cells and may involve screening different molecules, subjecting them to one or more application conditions, and isolating the molecule variants that have the desired characteristic. For example, the desired molecular variant may be one that exhibits a certain protein-protein interaction or metabolic activity. Large numbers of molecules may be screened using the processes described herein, and desired molecular variants displaying the functional characteristic may be isolated and subjected to further characterization. Further characterization (e.g., chemical or biochemical analysis) of the different discovery molecules may include, in non-limiting examples, chemical or elemental analysis such as mass spectrometry, gravimetry, atomic spectroscopy, nuclear magnetic resonance (NMR), chromatography, plasma mass spectrometry, X-ray photoelectron spectroscopy (XPS), Auger electron spectroscopy, etc. The resulting data (e.g., chemical composition, physical properties, etc.) may be used to predict (e.g., using a computer readable medium) which structural elements (e.g., elements, chemical compositions, etc.) have the desired functional characteristic or may have an improved functional performance (e.g., protein-protein interaction or metabolic activity).

The different molecular variants (e.g., target protein variants) of the molecule optimization unit may be comprised in a library (e.g., a protein library, a peptide library, a biomolecule library) or the different discovery molecules may be encoded for in a genomic variant library, which in some instances comprises genetic variants that are generated or synthesized. For example, in the case of generated or synthetic genetic variants, the genetic variants may be generated by mutagenesis (e.g., random mutagenesis, (e.g., exposure to mutagens such as ultraviolet radiation, X-ray radiation, gamma-ray radiation, chemical mutagens, e.g., ethyl methyl sulfonate, reactive oxygen species, deaminating agents, polycyclic aromatic hydrocarbons, alkylating agents (e.g., ethylnitrosourea, nitrosamines) aromatic amines, alkaloids, bromine, sodium azide, psoralen, benzene, metals (e.g., arsenic, cadmium, chromium, nickel) or biological agents (e.g., transposons, viruses, bacteria), etc.), saturation mutagenesis, circular permutation), Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), a CRISPR guided DNA polymerase, error prone polymerase chain reaction (epPCR) or other genomic engineering approaches. In some instances, the genomic variant library is or comprises a whole-genome mutagenesis library, a genome-shuffled library, a targeted genomic library such as a promoter swap library, and a transposon library (e.g., promoter insertion library). In some instances, the targeted genomic library comprises or encodes for one or more members selected from the group consisting of promoters, 5' untranslated regions, 3' untranslated regions, ribozymes, RNA stability sequences, secretion peptides, fusion proteins, DNA binding domains, protein-protein binding regions, codon optimized genes, codon randomized genes, terminators, and non-homologous end joining. In some instances, the genomic variant library may be a single gene random mutation library, a site saturation library, a small-insert metagenomic library, a large-insert metagenomic library. In some instances, the different discovery molecules are DNA-encoded molecules. The DNA-encoded molecules may be comprised in a library, such as a metagenomic library, a DNA-encoded library, a library from one or more organisms, or a Function Generator-created library. The DNA-encoded molecule library may comprise randomly-generated DNA-encoded molecules, naturally-occurring DNA-encoded molecules, or a combination thereof.

As with the strain optimization unit, multiple experimental conditions may be screened simultaneously using the systems and methods described herein. For instance, the molecule optimization unit may be configured to simultaneously screen or analyze millions of reaction volumes comprising different molecular variants (e.g., target protein variants) that have been subjected to the same or different application conditions. Beneficially, the molecule optimization unit may provide multiplexed, multiparametric information on molecular variants and environmental (or application) conditions of the molecular variants. Additionally, the molecular optimization unit may be beneficial in screening molecules (e.g., protein targets encoded by DNA) having a desired performance criterion, e.g., a molecule having the desired characteristic such as a threshold enzymatic activity level or other metabolic or phenotypic trait or production of a target protein under a particular application condition.

Reaction vessels: The reaction vessels of the molecular optimization unit may be the same or different as the reaction vessels of the strain optimization unit and the molecule discovery unit. The reaction vessels of the molecule discovery unit may be, for instance, droplets or plugs, wells (e.g., microwells, nanowells, picowells, etc.), vials, tubes, flasks, or other container. In some instances, the reaction vessels are comprised in a microfluidic device which comprises or is a part of a consumable unit. In some instances, the reaction vessels are a member of an array, e.g., a microwell array or plate, a nanowell array or plate, etc. Multiple types of reaction vessels may be used (e.g., droplets and wells) for any of the processes described herein, either simultaneously or sequentially. The reaction vessels may be physically distinct or discrete, or the reaction vessels may be capable of being merged or coalesced.

Each reaction vessel can comprise a different molecule (e.g., target protein variant) for screening. For example, as with the strain optimization unit, it may be useful to screen a library of genetic variants encoding for different proteins for a desired functional characteristic (e.g., biomolecular (e.g., enzymatic) activity, biomolecule interaction, phenotypic or metabolic trait); accordingly, each reaction vessel may be configured to contain a different genetic variant for screening. In some cases, each reaction vessel comprises one or more cells having the genetic variant. For example, each reaction vessel may comprise a single cell or more than one cell having a single genetic variant that is different than the genetic variants of other cells in other reaction vessels. Alternatively or in addition to, each reaction vessel may comprise a clonal population of cells with a single genetic variant. In other examples, it may be useful to screen different genetic variants within a single reaction vessel; accordingly a reaction vessel may comprise a mixture of cells with different genetic variants. In such an example, each reaction vessel may comprise a combination of cells and genetic variants.

As described herein, the reaction vessels may comprise a single cell or multiple cells and may be configured to be assessed in a high-throughput manner. Any number of reaction vessels may be generated or used within a given duration. In some instances, it may be beneficial to screen different numbers of reaction vessels (or volumes). Accordingly, the number of reaction vessels (or volumes) used or generated may be adjusted according to the suitable application or experimental purpose. For instance, when large numbers of discrete reaction volumes are useful e.g., for screening purposes (e.g., for molecule discovery), at least 10,000 reaction volumes, at least 100,000 reaction volumes, at least 1,000,000 reaction volumes, at least 10,000,000 reaction volumes, at least 100,000,000 reaction volumes or more reaction volumes may be used. In other instances, smaller numbers of discrete reaction volumes may be useful or required (e.g., for a targeted screen or for rational design of experiments with a limited number of species for screening). In such instances, at most 100,000,000 reaction volumes, at most 10,000,000 reaction volumes, at most 1,000,000 reaction volumes, at most 100,000 reaction volumes, at most 10,000 reaction volumes, at most 1,000 reaction volumes or fewer may be used or generated.

Similar to the strain optimization unit, the reaction vessels of the molecule discovery unit may be comprised within a microfluidic device and may accommodate any useful volume. In the case of droplets, the droplets may comprise any useful composition, as described above.

Assays: In some instances, the sorting of the biological variants may comprise the use of one or more screening operations. The screening operation may include an assay, e.g., a direct assay, an indirect assay, a binding assay, a reporter assay (which may be in vitro or in vivo), a fluorogenic assay, a chromogenic or colorimetric assay, etc. One or more immunological assays may be used, including, but not limited to: enzyme-linked immunosorbent assay (ELISA), sandwich ELISA, proximity ligation assay, etc. In some instances, a reporter molecule or selection molecule is used for screening. The assay or reporter or selection molecules may be useful in the detection of the presence of a genetic variant or a functional characteristic (e.g., phenotypic or metabolic trait) of the biological variant. For example, in cases where the desired biological variant is a cell that comprises enzymatic activity, the cells in the reaction vessels may be screened in the presence of a chromogenic or fluorogenic substrate that changes color or fluoresces upon conversion of the substrate to a product by the desired enzymatic activity. In such an example, the reaction vessels that exhibit a change in color or fluorescence may indicate that the cell comprises the desired enzymatic activity; subsequently that cell may be isolated and further analyzed (e.g., via sequencing, protein analysis, etc.) to determine information on the biological variant (e.g., DNA or RNA sequence, protein sequence or composition, etc.). In other examples, the desired biological variants may comprise a selection or reporter molecule; for example, in the case of selection molecules, only cells with the desired trait may survive in a given culture condition (e.g., only cells with transgenes or recombinant genes that encompass antibiotic resistance will survive in a growth medium comprising antibiotics). The surviving cells may be screened for the desired functional characteristic and those that have the desired functional characteristic may be subjected to further analysis. In yet another example, only cells with the desired trait may express a reporter molecule (e.g., fluorescent or detectable protein) indicating that a transgene or recombinant gene is present. In such examples, cells exhibiting a desirable trait or functional characteristic may be isolated from the reaction vessel and subjected to further analysis, as described herein. In other examples, the assay (e.g., immunoassay, binding assay, etc.) may be used to determine the presence of the molecule of interest (e.g., a protein, a nucleic acid molecule, a lipid, a carbohydrate, a metabolite, or a combination thereof) in each of the genetic variants and the genetic variants comprising the molecule of interest may be isolated and further analyzed.

Further analysis may be performed on selected biological variants (e.g., selected cells demonstrating the desired characteristic). Such analyses may include, without limitation, protein analysis (e.g., mass spectrometry, protein assays), nucleic acid analysis (e.g., sequencing), lipid analysis (e.g., Raman scattering or spectroscopy), chemical composition analysis (e.g., NMR, XPS, chromatography, etc.), imaging (and image analysis), spectroscopy, or other analysis methods or screens, as described herein. Such analysis methods may be useful in determining the identity of the genetic variant, e.g., by yielding information on the DNA sequences or genes, amino acid sequence, protein properties (e.g., post-translational modifications). Such information may then be collected and stored in a database or reintegrated with the molecule discovery library, optionally with any functional characteristics such as desired biological activity, phenotypic or metabolic trait, etc.

In some instances, the molecule optimization unit may comprise or be coupled to a detector. The detector may be used to determine the presence or absence of a molecule of interest or a functional characteristic in a cell or reaction vessel, which may enable screening and/or selection of the desired biological variants. The detector may include one or more analytical instruments, e.g., a mass spectrometer, Raman spectrometer, near infrared (NIR) spectrophotometer, Fourier Transform Infrared (FTIR) spectrometer, a spectrophotometer (e.g., a fluorescence or absorbance plate or cuvette reader), a piezoelectric sensor, etc. The detector may be configured to count cells (e.g., a cell counter, a flow cytometer). The detector may comprise one or more optical components and may comprise, in some instances, a microscope (e.g., a stereoscope, a compound microscope, a fluorescent microscope, a polarizing microscope, a confocal microscope, a differential interference contrast microscope, a super-resolution microscope etc.), or components or combinations thereof. The detector may be used to detect a physical property of a cell or reaction vessel, including but not limited to: magnetism, impedance, topography or geometry, scattering, morphology, absorbance, fluorescence, color, clustering of cells, cell or colony size, etc. The detector may be a point detector or an array or image detector.

Movement actuators: In some instances, the reaction vessels are moved (e.g., toward the detector) using a reaction vessel movement actuator. The vessel movement actuator may be a robotic manipulator, a flow generator, an acoustic droplet generator, optical tweezers, a thermal drop-on-demand, a piezoelectric drop-on-demand, a lithography unit, a digital microfluidic device, or a combination thereof. The movement actuator may comprise a stage and any necessary moving parts, e.g., screws, gears, threads, motors, pumps, compressors, resistors, transistors, springs, pulleys, etc. In some instances, the reaction vessels are placed on or adjacent to a substrate that is connected to a movement actuator.

Libraries: The molecule optimization unit may comprise a molecular variant (e.g., target protein variant) library, which may be used in the processes described herein. The molecule optimization library can comprise a plurality of different genetic or protein variants, as described herein. For example, the library may comprise a plurality of target protein variants which are encoded by different genetic variants. The plurality of genetic variants may be from a first strain. For instance, a first strain of cells (e.g., bacterial, yeast, animal, plant, etc.) cells may be subjected to conditions sufficient to generate the plurality of different genetic variants, such that each of the genetic variants is different. Each genetic variant of the plurality of genetic variants may comprise, for example, DNA or RNA that has a different sequence than other genetic variants of the plurality of genetic variants. The plurality of different genetic variants may encode for variations of the same biomolecule (e.g., DNA, RNA, peptides, proteins, etc.). For instance, the plurality of different genetic variants may include different DNA sequences that encode for variations in RNA sequences that are subsequently translated into proteins. Variations in the different DNA sequences in the library can result in different RNA sequences and thus proteins. In some instances, the proteins encoded by the genetic variants (which may have variations in DNA and/or RNA) are enzymes. In such instances, the enzymes may form or be a part of a metabolic pathway. The enzymes or metabolic activity may be used as a screening parameter or performance requirement during the molecule optimization process.

In some cases, the molecule optimization unit is configured to screen the molecular variants and select for and/or classify the desired biological variants (e.g., molecular variants) based on a functional characteristic (e.g., phenotypic or metabolic trait or activity) or measurement. For example, a phenotypic or metabolic measurement can include, in non-limiting examples: protein or enzymatic activity, protein expression levels, quantity of byproducts or metabolites, etc. For instance, a desired biological variant may be one that has a defined or minimum-threshold enzymatic activity. In such cases, the molecular variants of the molecule library (e.g., target protein variant library) may be screened in the molecule discovery unit, and only the molecular variants having the defined or minimum-threshold enzymatic activity are selected for further analysis. The molecular variants may be subjected to further analysis (e.g., sequencing, protein analysis, chemical analysis) to determine the nucleic acid or protein sequence or chemical composition of the enzyme of interest. In some instances, the sequence or composition of the molecular variant is added to a database and/or reintegrated in the molecule optimization library with the functional properties or performance. In some instances, the sequence or composition of the molecular variant is used in the computer readable medium to generate a prediction on the performance of a molecule (e.g., a target protein variant) based on a given set of conditions (e.g., application conditions) and structure (e.g., sequence, chemical composition, etc.).

The molecule optimization library may comprise any number of molecular variants as is useful for screening molecules, such as target proteins, that have or effect (e.g., via a protein-protein interaction or signal transduction pathway) a desired functional characteristic. The molecule optimization library may comprise at least 100 different molecules, at least 1,000 different molecules, at least 10,000 different molecules, at least 100,000 discovery molecules, at least 1,000,000 different molecules, at least 10,000,000 different molecules, at least 100,000,000 different molecules or more. As described herein, the molecule optimization processes may be recursive or iterative. In such cases, the number of different discovery molecules screened per iteration may vary; for instance, the first cycle may screen 10,000,000 different molecules while the second cycle screens 100,000 different molecules. Conversely, the number of different discovery molecules may increase in between cycles, e.g., via introduction of new biological diversity or variants (e.g., new strains, new different discovery molecules, etc.) and/or conditional diversity (e.g., varying fermentation or application conditions for some or all of the newly introduced or screened biological variants).

Target proteins: The molecular variants may comprise genetic variants encoding for target proteins. Target proteins may be any useful protein or peptide, such as a structural protein, enzyme, surface receptor protein, peptide hormone, therapeutic peptide, an immune system component (e.g., antibody, antibody fragment, antibody conjugate), a bioactive peptide (e.g., lantipeptide, lassopeptide, a non-ribosomal synthesized peptide), or other useful protein or peptide. The target protein may be an industrial enzyme, such as a polymer-degrading enzyme (e.g., poly(ethylene terephthalate hydrolase), lipozyme, palatase, cellulase, amylase, resinase, amidase, isomerase, etc. The target protein may be a therapeutic enzyme such as a lipase, DNAse, 1-asparaginase, 1-glutaminase, urokinase, uricase, collagenase, glucosidase, galactosidase, tyrosinase, etc. The target protein may be a therapeutic protein such as an antibody, antibody fragment, or other binding protein. The target protein may be a peptide hormone such as amylin, adiponectin, adrenocorticotropic hormone, angiotensin, antidiuretic hormone, natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, releasing hormone, hepcidin, human chorionic gonadotropin, human placental lactogen, growth hormone, inhibin, insulin, leptin, lipotropin, luteinizing hormone, stimulating hormone, motilin, orexin, osteocalcin, oxytocin, pancreatic polypeptide, parathyroid hormone, pituitary adenylate cyclase-activating peptide, prolactin, relaxin, renin, secretin, somatostatin, thrombopoietin, thyroid-stimulating hormone, thyrotropin-releasing hormone, vasoactive intestinal peptide, guanylin, urogyuanylin, or other peptide hormone. The target protein may be a structural protein such as actin, actinin, aggrecan, biglycan, cadherin, clathrin, collagen, decorin, elastic, fibrin, fibrinogen, fibronectin, heparin, keratin, laminin, mucin, myelin, myosin, spectrin, tropomyosin, troponin, tubulin, vimentin, vitronectin, etc. The target protein may be a protein or enzyme that participates in DNA replication, transcription or translation, such as a polymerase (e.g., RNA polymerase), ligase, helicase, ribozyme, ribosome, spliceosome protein, chaperone protein, etc. The target protein may be a signaling factor or cytokine (e.g., interleukin, interferon, tumor necrosis factor, transforming growth factor, immune-modulating factor, etc.). The target protein may be a food-based or nutritional protein, e.g., ovalbumin, hemoglobin.

Data sets: One or more components of the molecule optimization unit may comprise a computer readable medium, as is described in further detail below. In some instances, the computer readable medium is a computer model that inputs data and that is configured to generate a prediction on a functional performance of a structural aspect (e.g., sequence, peptide or protein motif, chemical composition, etc.). The computer readable medium may be configured to input a plurality of data sets, which may be from a database or from an experimental module, e.g., from the integrated units. For example, the computer readable medium may comprise a machine learning algorithm that inputs function data, sequence data, and/or enrichment data (e.g., of a polymer variant) and outputs a designed molecule expected to have an improved function. The computer readable medium may also be configured to perform a variety of other functions, such as storing the data sets, setting a threshold for the data sets to be stored, communicating with one or more integrated units for automated processing, etc.

In some instances, where a machine learning algorithm is used, the machine algorithm may comprise a supervised learning algorithm, an unsupervised learning algorithm, or a reinforcement learning algorithm. The algorithm may comprise a linear regression, a logistic regression, a decision tree, a supporting vector machine (SVM), a Naïve Bayes, a k-Nearest Neighbors, a k-Means, a random forest, a dimensionality reduction algorithm, a gradient boosting algorithms, XGBoost, light gradient boosting algorithm, Catboost, etc., or a combination thereof. The machine learning algorithm may comprise a natural language model, and one or more neural networks. The natural language model may apply one or more techniques for computer implementation, such as syntactic analysis or semantic analysis. For example, the syntactic analysis may be employed and may include sub-tasks such as tokenization, part of speech tagging, lemmatization and stemming, stop-word removal, etc. The semantic analysis may include word sense disambiguation, relationship extraction, etc.

In some instances the experimental systems of the molecule optimization unit may be integrated with the other integrated units. For example, the molecule optimization unit may comprise the computer readable medium that generates the prediction on an optimal molecule or genetic variant, and the optimal molecule or genetic variant may be introduced into a strain optimization library in the strain optimization unit. Accordingly, different functions may be performed by the integrated units that interact with one another, as described below.

(iv) Integrated Systems

Computer readable medium: In some instances, one or more integrated units are integrated via or coupled to a computer readable medium. The computer readable medium may be capable of performing one or more functions, including, in non-limiting examples: storing data sets from any of the integrated units in a data repository, setting a threshold parameter for data to be delivered to the data repository, and instructing any of the units to repeat an input diversity screen. For example, data, such as sequence information and functional performance from the strain optimization unit may be integrated in the computer readable medium, which may be used to generate predictions for molecule optimization (e.g., provide genetic variants that are predicted to perform above a threshold criterion). In another example, data from the molecule discovery unit may be integrated in the computer readable medium, which may be used to generate a prediction on a molecular variant that is predicted to enhance functional performance under a given fermentation or application condition.

In some instances, the computer readable medium comprises a quality-control function. For example, the computer readable medium may be configured to store data (e.g., in a database or data repository) that is above a quality threshold. The computer readable medium may thus set a threshold parameter for data, and subject input data to the threshold. Data that abides by the threshold (e.g., is above the threshold) is delivered to the data repository. Non-limiting examples of threshold parameters include: signal-to-noise ratio, statistical significance, target performance criteria, e.g., enzymatic activity level, protein or molecular interactions, presence of a phenotypic or metabolic trait, etc.

System Automation: In some instances, the computer readable medium is configured to automate one or more processes in one or more of the integrated units. In such instances, the one or more integrated units may comprise a communication interface (e.g., wireless or wired communication interface) that communicates with a communication interface of the computer readable medium. The computer readable medium may direct commands or instructions (e.g., via the communication interface) to the integrated units (or a component thereof). For example, the computer readable medium may be configured to control the reaction movement actuator (e.g., fluid handling units, flow generator, etc.) of one or all of the integrated units by relaying one or more commands or directions, thereby controlling the movement of the reaction vessels. Similarly, the computer readable medium may be configured to control the provision of reagents (e.g., culture media, reaction or detection reagents) to the reaction vessels, e.g., using fluid handling units, flow generators, movement actuator, etc. The reaction movement actuator, the computer readable medium, and the detector may all be integrated, and in some instances, may be connected via a feedback loop.

In one example, the feedback loop may be used to control the volume (e.g., reagent volume) within each reaction vessel, which may be beneficial in ensuring consistent growth between cells in each reaction vessel. The feedback loop may be used to monitor the conditions of each reaction vessel and automatically adjust (e.g., via a feedback controller) the conditions based on a set of predefined conditions, e.g., temperature, pH, media components, etc. Similarly, the feedback loop may comprise detection or image recognition software, which may be used to designate whether a given reaction vessel comprises the desired number of cells, the correct volume, flow rates, etc. In the cases where droplets are used, the feedback loop may comprise a flow rate adjuster to maintain a frequency of droplet generation. Reaction vessels that do not have the desired number of cells may be excluded from further screening or analysis. As such, the computer readable medium may make decisions on whether a cell or reaction vessel will be further screened or analyzed based on such feedback.

In some instances, a feedback loop may be used in the screening processes described herein. The reaction vessel movement actuator may be configured to sort desired biological variants and isolate them (e.g., sorting droplets in a microfluidic device using fluorescence or colorimetric activated cell sorting, magnetic sorting, dielectrophoresis, etc.). In such an example, the detector may collect a signal or an image from each reaction vessel, the signal or image may be processed (e.g., via the computer readable medium), and the reaction vessel exhibiting a functional performance (e.g., fluorescence or colorimetric signal above a threshold) may be automatically gated and/or sorted (e.g., to another chamber, vessel, or portion of a device). Accordingly, the reaction movement actuator (or sorter), the detector (which detects the signal) and the computer readable medium may be integrated. In some instances, the amount or a proportion of reaction vessels and/or cells may be sorted, e.g., a fixed percentage (e.g., a top user-defined percentage). In some instances, only the top percentage (e.g., the highest functional performance) of cells or reaction vessels may be sorted for collection and further analysis. For example, only the top 50%, 40%, 30%, 30%, 25%, 15%, 10%, 5%, 1%, 0.5%, 0.1%, 0.05%, 0.025%, 0.01%, etc. of cells or reactors may be sorted for collection. In some instances, the reaction movement actuator may be configured to pause, delay, or otherwise change the movement of the reaction vessels based on an output of the computer readable medium using a feedback loop. For instance, if an error is detected by the detector (e.g., undetectable signal, suspected blockage, etc.), the computer readable medium may automatically detect the error and direct the movement actuator to pause, delay, or otherwise change the movement of the reaction vessels.

Similarly, the computer readable medium may instruct one or more system components (e.g., a fluid handling unit, a flow generator, etc.) to automatically introduce additional reagents (e.g., detection reagents, or other reaction reagents, e.g., pH-modifying agents, ionic strength modifying agents, ions, substrates, inhibitors, enzymes, competitors, oxygen, carbon dioxide, etc.) into the reaction vessels. Such integration of multiple system components may allow for precise, defined reaction times, along with detection, analysis, sorting, etc. within a designated time frame. For example, the addition of detection reagents (e.g., a substrate for an enzymatic assay for measuring enzymatic activity level) may be instructed by the computer readable medium, such that each reaction vessel is incubated with an amount of the detection reagent for the same duration of time prior to detection. As the incubation time may affect the readout (e.g., longer incubation times will increase the signal intensity as more substrate is converted to product), having precise control of the amount of detection reagent added and/or the incubation time may prevent spurious readouts, e.g., from reaction vessels that were incubated for a longer duration and that do not necessarily represent a higher functional performance.

As such, the methods and systems described herein may allow for precise system controls that result in low variation across reaction vessels. For example, the computer readable medium may comprise instructions that when executed by one or more processors, cause the system to partition a population of cells into a plurality of reaction vessels or reaction volumes to yield partitioned cells and assay the partitioned cell for a phenotype or functional performance to generate signals for the partitioned cells. The generated signals may have a low coefficient of variation across the reaction vessels. For example, for a given biological variant (e.g., a strain comprising the same DNA sequence, a homogeneous population of cells, etc.), the coefficient of variation (e.g., as measured by the signal output, which can be representative of a product quantity or an activity level) may be less than about 500%, less than about 400%, less than about 300%, less than about 200%, less than about 100%, less than about 90%, less than about 80%, less than about 70%, less than about 60%, less than about 50%, less than about 40%, less than about 30%, less than about 20%, less than about 10%, less than about 9%, less than about 8%, less than about 7%, less than about 6%, less than about 5%, less than about 4%, less than about 3%, less than about 2%, or less than about 1%. In some instances, the coefficient of variation may fall in a range of values, e.g., from 1% to about 10%, or from about 2% to about 8%, or from about 10% to about 100%. Such a coefficient of variation may account for different noise characteristics within the system, e.g., biological variation (e.g., performance differences that are naturally occurring in biology across identical strains), reagent addition and incubation times, optical/detection noise, etc. In some examples, the strain optimization, molecule optimization, or molecule discovery units described herein may comprise a coefficient of variation of less than about 10%, indicating that the systems and methods used herein may be advantageous in accurately characterizing libraries of variants with low technical noise or variation.

In some instances, the computer readable medium may comprise a proportional-integral-derivative (PID) algorithm that can correct for drift within the system. For example, the PID algorithm may correct for drift due to deviations in mechanical instruments, liquid viscosities, or temperature. Correction of drift may be advantageous in preventing erroneous sorting decisions by the system caused by drift. Such a correction may comprise, for example, changing of the threshold gates used for sorting the reaction vessels or cells, or regulating the target percentage of the sorted cells (e.g., a top percentage of the highest functioning cells). In some instances, the computer readable medium may comprise a proportional controller or a proportional integral controller.

In some instances, the computer readable medium may be configured to execute one or more commands related to running the strain optimization processes, the molecule discovery processes, or the molecule optimization processes. The computer readable medium may instruct each of the units, individually or collectively, to run one or more of the operations described herein. For example, the computer readable unit may instruct the strain optimization unit to perform a screen for biological conditions under a given experimental condition (e.g., using a set of biological or genetic variants, application or fermentation conditions, etc.), to re-run an experimental condition, or to repeat a diversity screen (e.g., re-running experiments with added genetic variants, application or fermentation conditions, or a combination thereof).

In some instances, the computer readable medium may be configured to input one or more target parameters. The target parameters can include, for example, a performance threshold or desired functional performance such as enzymatic activity, molecular or protein interactions, binding affinity, etc. In such an example, the computer readable medium may be configured to execute one or more commands related to running the strain optimization processes, the molecule discovery processes, or the molecule optimization processes until the target parameter is reached. In one non-limiting example, a target parameter of a desired level of enzymatic activity may be input in the strain optimization unit. The computer readable medium may then be configured to iteratively and/or automatically run the strain optimization processes, optionally inputting additional biological or conditional diversity (e.g., via introducing new specific or nonspecific genetic variants or fermentation conditions) and screening for the enzymatic activity (e.g., using a fluorescence assay) until the target threshold of enzymatic activity is met. For example, the computer readable medium may be configured to automatically introduce one or more point-based or specific mutations in a cell at a known gene locus or loci, using, for example, a correlation between a known or empirically derived structural (e.g., sequence)-functional relationship. In another example, the computer readable medium may be configured to automatically introduce random mutations in a cell, either at a defined or undefined gene locus. Further screening may be performed, and the strains meeting the target threshold may be isolated and the strains or proteins therein may be analyzed.

Target performance parameters: One or more target performance parameters may be input into the system (e.g., one or more of the integrated units) to screen the biological or molecular variants. A target performance parameter may pertain to the desired functional characteristic of the biological or molecular variants. For instance, the desired functional characteristic may be a yield of the desired molecule (e.g., protein or peptide), growth or proliferation rate of cells, sensitivity of a cell to a condition (e.g., application or fermentation condition such as pH, temperature, ion concentration e.g., divalent cations such as calcium, magnesium, etc.), cell viability, titer, molecular interactions (e.g., protein-protein interactions), stability (e.g., thermal stability, resistant to protease degradation, etc.), binding characteristics (e.g., affinity or avidity to another molecule, substrate specificity), metabolic or phenotypic traits (e.g., enzymatic activity, catalytic performance), expression levels of a protein, quantity of byproducts or metabolites, presence or level of target protein folding, target-protein-to-byproduct ratio, target protein modification (e.g., glycosylation, phosphorylation, sumoylation, acylation, ubiquitination, acetylation, lipidation, methylation, hydroxylation, or other post-translational modification), or other functional characteristic. In some instances, the target performance parameter may be selected contingent on a conditional parameter. For example, a desired biological variant may be a cell that has increased yield of a target protein under a specified fermentation condition (e.g., low oxygen, low temperature, change in ion concentration, etc.). In another example, the desired biological variant may be a cell that proliferates under a specified fermentation condition.

Integration of data from the integrated units: In some instances, the data from each of the integrated units may be added to the computer readable medium (e.g., in a data repository). For example, as described herein, one or more of the integrated units may comprise or interact with the computer readable medium. The computer readable medium may be configured to input one or more data sets and output a prediction of a structural-functional relationship of a molecule, optimal operation conditions (e.g., application or fermentation conditions) for a desired functional characteristic, etc. The data sets that are input in the computer readable medium may be from any one of the integrated units. For example, the data sets may be generated from one of the screens of the biological or molecular variants from any one of the integrated units (e.g., strain optimization unit) and may comprise information on the desired biological variants and properties thereof (e.g., structure, sequence, composition, etc.) as well as conditional information (e.g., culture, fermentation, application, or reaction conditions). In some instances, data sets that are not generated from the integrated units may be comprised in or added to the computer readable medium. For example, the data sets from databases may be input into the computer readable medium.

Biological diversity and conditional diversity screen: In some aspects, the integrated system may input data bases, data sets, or data streams comprising information on a biological diversity screen and/or a conditional diversity screen. The biological diversity data can comprise information on the input biological variants (e.g., genetic variants having different genetic elements, molecular variants, etc.) of a biological diversity screen (e.g., a screen to identify desirable biological variants), which inputs can include, in non-limiting examples: strain information, DNA sequence, RNA sequence, amino acid sequence, protein modifications (e.g., post-translational modifications), functional performance (e.g., enzymatic activity, yield, titer, growth rate, protein-protein interactions, binding characteristics), or a combination thereof. For example, the biological diversity data stream may comprise data generated from a screen from the strain optimization unit, which may generate data on the different genetic (or genomic) variants that produce a desired target protein or have a desired functional characteristic. Such data may include (i) the identity of the genetic (or genomic) variants for each strain, e.g., the DNA or plasmid sequence and/or the peptide or proteins that are produced from each of the genetic (or genomic) variants, and (ii) the performance (e.g., enzymatic activity, growth rate) characteristics of each of the genetic variants or proteins or peptides derived therefrom. Other biological diversity data (e.g., protein structure and sequences, protein performances) from public sources or databases may also be comprised within the biological diversity data sets.

The conditional diversity data may comprise data on one or more conditions used to generate a desired biological variant. For example, during strain optimization, one or more fermentation conditions (e.g., pH, nutrient level, carbon dioxide level, temperature, etc.) may be altered to achieve a desired functional performance in a set of genetic variants. These fermentation conditions, and in some instances, the functional performance, may constitute one or more conditional diversity data sets. Similarly, the application conditions used in molecule optimization (e.g., for a target protein generation or optimization) or molecule discovery may be comprised in the conditional diversity data. Other conditional diversity data (e.g., application or fermentation conditions) from public sources or databases may also be comprised within the conditional diversity data sets.

In some instances, the biological diversity data and the conditional diversity data are independently programmable data sets. For instance, the biological diversity data and the conditional diversity data may be generated from a single experiment (e.g., a strain optimization screen), but the generated data may be discretized into the input parameters or variables of the experiment. For example, the input parameters or variables of the experiment (e.g., the genetic variants and the fermentation conditions) may result in a set of data comprising the functional performance of each combination of genetic variant and fermentation condition. However, the programmable data sets may be configured such that each parameter or variable is independently manipulatable. In one example, the computer readable medium may generate a parameterized (e.g., multiparametric) model, which can analyze the relevant weight of each of the variables (e.g., the fermentation conditions and the genetic variants) on the strain performance. In some instances, the biological diversity data or the conditional diversity data comprise both experimental data and data from databases (e.g., publicly available data sets).

Altogether, the data from the biological diversity screen and the conditional diversity screen may be used to identify a desirable biological variant (e.g., a genetic variant), based on the target parameters (e.g., target performance parameters) that are input into the system.

Machine learning algorithm: In some instances, the computer readable medium comprises a machine learning algorithm. The machine learning algorithm may comprise one or more neural networks that may be used to iteratively or continuously integrate and analyze the data generated from the integrated units or from external sources (e.g., publicly available databases) and discover new features (e.g., protein-encoding genetic variants) or molecules that are predicted to have a functional characteristic or target performance. The machine learning algorithm may be trained using, for instance, data sets from large libraries, such as publicly available or public-contributed databases of known structural-functional relationships of molecules, e.g., DNA or amino acid sequences shown to exhibit a functional characteristic. Alternatively or in addition to, the machine learning algorithm may be trained using data sets generated from one or more of the integrated units.

The machine learning algorithm may comprise any number or type of useful algorithms. For instance, the machine learning algorithm may comprise an Elastic-Net Regularized Generalized Linear Models (GLMNET), Support Vector Machine Regression (SVM), Random Forest (RF), Extreme Gradient Boosting (XGBoost), Multilayer Perceptron (MLP), a Convolutional Neural Network (CNN), a deep neural network (DNN), or a combination thereof. The machine learning algorithm may comprise supervised learning, unsupervised learning, support vector machines, or other algorithms. The machine learning algorithm may be used to predict or generate biological variants that may achieve a desired functional characteristic. For example, the machine learning algorithm may be configured to output at least 1, at least 10, at least 100, at least 1,000, at least 10,000, at least 100,000, at least 1,000,000 or more biological variants that may have a predicted or threshold amount of a functional characteristic.

In one example, the machine learning algorithm may be used to predict a biological variant (e.g., genetic variant) or a structural component thereof (e.g., a molecular variant such as a gene sequence, an amino acid sequence, a motif, etc.) that has a desired or improved functional performance (e.g., enzymatic activity) that has not yet been empirically tested or determined. The predicted biological variant or molecular variant may be a novel molecule or sequence, a known molecule or sequence, or a combination thereof. The machine learning algorithm may input data from each of the integrated units as well as publicly available data sets to generate such a prediction. In some instances, the input data may be processed, e.g., cleaned, converted, normalized, standardized, etc. Subsequently, the predicted variant may be empirically tested for performance in one of the integrated units. The functional performance may be recorded and reintegrated into the machine learning algorithm, further refining the prediction algorithm. For instance, data that support that the prediction is correct and/or data that refute that the prediction is correct may be used to iteratively adjust or train the prediction algorithm. The process may be repeated as many times, e.g., across any number of generations, as is useful until a machine learning performance is obtained, e.g., until the machine learning algorithm outputs a predicted molecule with a specified accuracy or performance criterion.

In an example, training data may comprise data from a strain or molecule optimization unit. For example, a library of mutants, e.g., cells comprising genetic variants encoding for a polymer (e.g., protein) may be generated, e.g., using site saturation mutagenesis, in which each position of a polymer, such as a peptide or protein, may be mutated to all 20 amino acids. Optionally, additional random mutagenesis and recombination may be performed. The library of mutants may be screened, using the methods provided herein, and the data (e.g., sequence data, enrichment data, functional performance data (e.g., a quantity or amount of a product produced, an enzyme activity, etc. for a given nucleic acid sequence encoding a polymer, e.g., a protein or peptide or for a protein or peptide sequence), screening or assay conditions, etc.) may be input to train the machine learning algorithm to predict new variants expected to have an improved functional characteristic.

In some instances, the machine learning algorithm integrates data from each of the integrated units. For example, the molecule discovery unit may input one or more molecules and application conditions, screen the molecules for a desired functional activity, and output the molecule identity (e.g., DNA or amino acid sequence), and functional performance of each of the molecules. These outputs may be provided as inputs in the molecule optimization unit. Subsequently, the molecule optimization unit, optionally using biological diversity and/or conditional data from databases (e.g., DNA or protein databases such as UniProt), may produce a prediction on which biological variants (e.g., strain genetic variants encoding for a target protein) or molecular variants (e.g., proteins, motifs, structures, compositions) are expected to have a threshold level of performance.

In some instances, the output prediction may include additional variants with sequence homology to the variants expected to have the threshold level of performance. For instance, the prediction may include variants with at least 70% sequence homology, at least 80% sequence homology, 90% sequence homology or greater to the main predicted variant. Homology may be determined, for instance, by aligning sequences of two or more nucleic acid molecules or proteins and determining the percentage of overlap. The additional variants may also be screened (e.g., using the strain optimization unit) to obtain additional data on the performance of such variants. The additional data may be used to generate an additional library of sequences or partial sequences (such as subsequences) comprising information on the key residues that are suspected of being important to the functional performance of the molecule (e.g., target protein). In some embodiments, the subsequence library may be generated by manipulating pre-existing libraries of genes or sequences encoding for key residues (e.g., via gene shuffling or other recombination strategies).

The biological variants or molecular variants may be built into a library (e.g., in the case of biological genetic variants, building a gene library). In some instances, the library is introduced into a plurality of cells. The library may then be further screened. The variants that have high performance may be isolated and further analyzed (e.g., sequenced or chemically analyzed) to identify the variant. The data from the different variants may be input into the machine learning algorithm to further refine the predictive capability. The machine learning algorithm may also produce novel combinations of variants and/or application conditions that are expected to have a high performance. These variants and conditions may then be input and used in the strain optimization unit for further screening.

FIG. 1 schematically depicts an integrated system as described herein. The integrated system 100 may be a platform that comprises a hardware unit, a consumable unit, and a biological or chemical unit, each of which units may be a part of comprise the one or more integrated units described herein. The integrated system 100 may comprise integrated units, such as a strain optimization unit 105, a molecule optimization unit 110, and a molecule discovery unit 115. Each of the integrated units may be configured to input a library (e.g., of genetic or molecular variants) and a set of conditions (e.g., fermentation conditions, application conditions) and output a prediction (e.g., of an optimized strain, an optimized molecule, or a novel molecule). As described herein, the processes performed within each of the integrated units may be recursive.

The strain optimization unit 105 may be configured to input a strain optimization library, which may comprise a plurality of genetic variants, which may be generated, for example, using random mutagenesis, MAGE, CREATE, transposon based mutagenesis, genome shuffling, random recombination, non-homologous end joining, traceable multiplex recombineering (TRMR), a CRISPR guided DNA polymerase, error prone polymerase chain reaction (epPCR), or may comprise a library from a database, such as a whole-genome sequencing (WGS) library. The strain optimization unit 105 may also input a set of fermentation conditions in which cells comprising the genetic variants are grown. As an output, the strain optimization unit 105 may produce an optimized strain (or information thereof) that has a threshold performance for a particular application (e.g., enzyme activity) under a set of conditions.

The molecule optimization unit 110 may be configured to input a molecule optimization library, which may comprise a plurality of genetic variants encoding for one or more target proteins (or have sequence homology to gene encoding for a target protein). The genetic variants may be generated using techniques such as saturation mutagenesis, circular permutation, MAGE, CREATE, transposon based mutagenesis, genome shuffling, random recombination, non-homologous end joining, traceable multiplex recombineering (TRMR), a CRISPR guided DNA polymerase, error prone polymerase chain reaction (epPCR) etc. In some instances (not shown), the molecule optimization library may comprise a plurality of molecular variants that are screened during the molecule optimization process, for a functional characteristic. The molecule optimization unit 110 may also input a set of application conditions including, but not limited to: temperature, media composition, oxygenation, salinity, pH, etc. As an output, the molecule optimization unit 110 may produce an optimized molecule (or information thereof, e.g., a DNA or protein sequence) that has a threshold performance for a particular application (e.g., catalytic activity, molecular interaction, etc.) under a set of conditions.

The molecule discovery unit 115 may be configured to input a molecule discovery library, which may comprise a plurality of molecular variants. In some instances, the molecular variants include a plurality of genetic variants which may have known and unknown sequences. The molecular variants may arise from a library collected from a sample (e.g., a biological sample, a soil sample, etc.), or the library may be generated, e.g., from a metagenomic library, a DNA-encoded library, a Function-Generator library, etc. The genetic variants may encode for one or more proteins and/or have a desirable functional characteristic. The molecule discovery unit 115 may also input a set of application conditions including, but not limited to: temperature, media composition, oxygenation, salinity, pH, etc. As an output, the molecule discovery unit 115 may produce a novel molecule (or information thereof) that has a threshold performance for a particular application (e.g., catalytic activity, molecular interaction, etc.) under a set of conditions.

Figure 2:
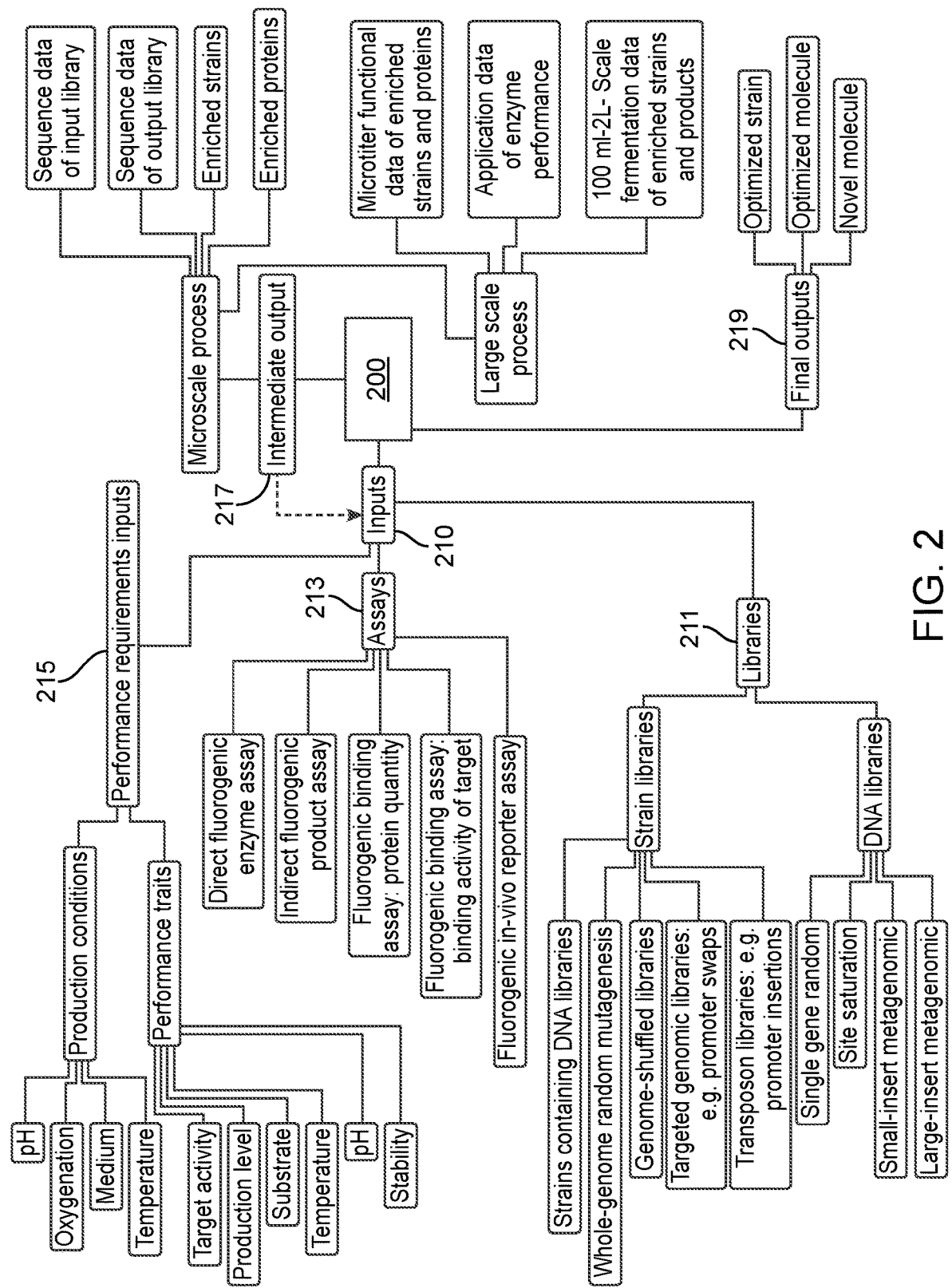
FIG. 2 schematically illustrates an example integrated system that is configured to input a plurality of parameters and output a prediction on an optimized strain, optimized molecule, or new molecule having a desired functional characteristic.

FIG. 2 schematically illustrates an integrated system for sorting desirable biological variants. The integrated system 200 may be configured to accept a plurality of inputs 210, including library inputs 211 (for example, strain libraries or DNA libraries), assay inputs 213 (e.g., experimental data about the functional characteristics of members of the library), and performance requirement inputs 215, including, for example, production conditions and performance traits (e.g., production or expression level, substrate conversion, production under a set of environmental conditions, stability, etc.). The integrated system 200 may output one or more intermediate outputs 217 (e.g., during one or more of the recursive cycles), which outputs may include data from the integrated units (e.g., the experimental modules) such as sequence data, enriched strains, or enriched proteins. The intermediate outputs 217 may also include predictions on how a set of parameters may perform on a larger scale, outputting data that include the functional performance of the inputs under certain conditions, and possible scaleup predictions of performance. The intermediate outputs 217 may be reintegrated into the integrated system 200 as an input. The final outputs 219 of the integrated system may include a predicted optimized strain, optimized molecule, or new molecule that is expected to have enhanced functional performance.

Computer Systems

Figure 3:
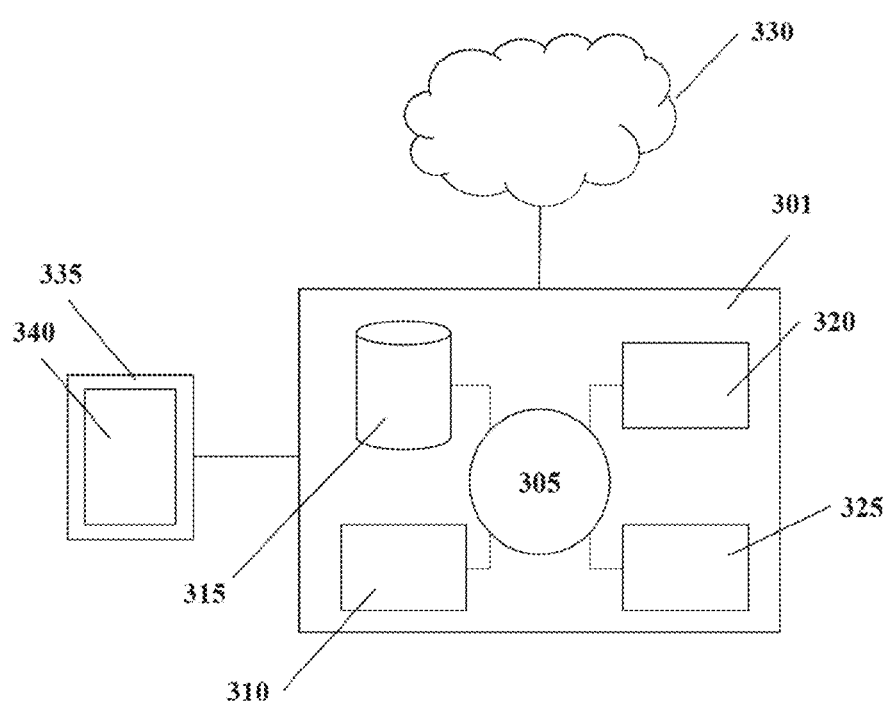
FIG. 3 shows a computer system that is programmed or otherwise configured to implement methods provided herein.

The present disclosure provides computer systems that are programmed to implement methods of the disclosure. FIG. 3 shows a computer system 301 that is programmed or otherwise configured to input one or more data streams, store the one or more data sets in a data repository, set a threshold parameter for the data, and/or instruct one or more of the integrated units to perform or repeat a diversity screen. The computer system 301 can regulate various aspects of strain or molecule optimization or discovery of the present disclosure, such as, for example, controlling one or more components of the strain optimization unit, the molecule optimization unit, the molecule discovery unit, inputting data, outputting one or more predictions on structural-functional relationships of molecules, etc. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, input threshold parameters for sorting the desired biological variants. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, a machine learning algorithm that iteratively inputs data streams on biological or conditional diversity and outputs a prediction on structural-functional relationships of molecules, an optimized strain, an optimized molecule, or a discovery molecule.

EXAMPLES

Example 1: Strain Optimization

It can be difficult to exactly match micro-scale screening conditions to those experienced at larger scales. In addition, the physical limitation of mixing large-scale vessels can result in strains in a highly heterogenous environment, with cells experiencing gradients in such conditions as oxygen levels, pH, carbon source concentration and temperature. In traditional screening programs, the screening of mutants can be often a time and cost bottleneck, and therefore a particular screening condition can be chosen that best approximates large-scale production conditions. It can be difficult to match these conditions, and the heterogeneity in conditions at scale can make it unlikely that a strain selected to be improved out of a particular small-scale screening assay will actually perform at larger scales.

The miniaturization of assays can reduce the time and cost of screening to the point where there is no longer a large impediment to screening large populations under a variety of conditions. In this example, libraries are screened under multiple conditions independently, and use next-gen sequencing (NGS) to identify mutations that are enriched under these different conditions. Mutations are classified into the metabolic pathways they affect. This phenotypic, sequence and metabolic pathway network data then feeds into a machine learning algorithm that enables prediction of which mutations or pathways or combinations are most important for performance under different environmental conditions, but also which mutations provide robust improvements across multiple conditions and are therefore generally useful.

Strain Construction

Starting with *Pichia pastoris* strain SMD1168, a protease-deficient commercially available strain from Thermo-Fisher, PCR amplification and cloning of the human Type I collagen gene, COL1A1, into a pPIC9K plasmid is performed, followed by transformation of the *Pichia pastoris* strain SMD1168 with the resulting plasmid. The pPIC9K plasmid allows generation of multi-copy plasmids under His4 selection and contains a secretion tag to allow extracellular production of protein.

Strain Optimization Library Construction

Libraries are created by performing whole-genome mutagenesis of the modified strain. Log-phase cells are then exposed to N-methyl-N'-nitro-N-nitrosoguanidine (NTG), quenching with sodium thiosulfate, at the appropriate concentration and time to give between 0.5-1% survival.

Microscale Assay for Collagen Production

PDMS nanowell arrays are created (Tones A J, Hill A S, Love J C. Nanowell-based immunoassays for measuring single-cell secretion: characterization of transport and surface binding. Anal. Chem. 2014; 86(23):1152-11569. doi: 10.1021/ac4030297) to detect production of collagen from the pichia cells. Cells are suspended from the library in growth media containing 0.5% methanol to induce protein expression. The cells are distributed into PDMS nanowells such that there is ~1 cell in 10 wells to ensure single cell measurements. The wells are covered with a glass slide coated with anti-COL1A1 antibody clone 5D8-G9 (Millipore-Sigma). Collagen secreted by cells is captured by the antibodies on the glass surface. The glass slide is then removed and the surface is stained with FITC-conjugated, goat anti-mouse antibody, and image with fluorescence microscopy. The FITC intensity is proportional to the amount of collagen secreted by the cell. Nanowells containing high-expressing clones are identified, picked out of the nanowell array with a robotic micromanipulator, and then grown under non-inducing conditions for further study.

Strain Improvement

Multiple screening experiments are set up in parallel, that cover the range of conditions the cells are likely to experience in production. For each condition, the highest producing cells are selected and re-grown to confirm improved production at 1 ml-scale in 96-well plates. After confirmation of performance, DNA is then extracted and next-generation sequencing (NGS) is performed, such as by using Illumina's MiSeq, either on pooled DNA from each condition or on individual clones. Mutations are identified that are associated with production under different conditions.

The strains that are found from the library are unlikely to be fully optimized. To purge non-beneficial mutations and discover beneficial combinations, protoplast fusion and "genome shuffling" is used, which enables recombination between genomes of high-producing strains. Recombination libraries are screened under the same initial conditions that are used for picking the highest producers.

The recursive cycle of library creation, screening and analysis is repeated until a strain is identified that meets performance requirements.

Example 2: Molecule Discovery

Discovery of a Novel Lipase Enzyme from a Metagenomic Library.

Environmental DNA (eDNA) is collected and purified from soil or other sources. The eDNA is sheared and is size selected to a range of 2-5 kb to encompass typical gene and promoter sizes. Fragments are cloned this into plasmids and are then transformed into high-transformation-efficiency *E. Coli*.

Lipase Assay

*E. Coli* cells are combined with a commercially available fluorogenic substrate, EnzCheck Lipase Substrate™ (ThermoFischer), and a cell lysis reagent, B-PER™ (ThermoFisher). The mixture is emulsified by shaking in a tissue lyser homogenizer (TissueLyser II, Qiagen) with a surfactant and oil mixture HFE-7500 (3M) with 2% "008" fluorosurfactant (RAN Biotechnologies). The emulsion is transferred to a shallow flow cell with a pierceable light-permeable membrane. In a 10×50×0.25 mm flow cell ~125 uL of emulsion can be stored, representing ~108 picoliter-volume emulsion compartments. As enzymes are released from lysed cells, droplets containing cells expressing active lipase become fluorescent. The flow-cell with fluorescent microscopy is imaged and regions of fluorescence are picked by piercing the covering membrane and aspirating with a micromanipulator needle.

Plasmids enriched for genes encoding active lipase enzymes are picked and retransformed into *E. Coli*. The cycle of transformation, assay, and recovery is repeated until the population is substantially enriched for active lipase genes.

Individual clones are then isolated from the selection and grown separately. Lipase activity is confirmed and sequencing of the insert is performed to identify open reading frames that encode lipases. The sequences are checked for homology to known lipase gene families, and new classes are identified. Depending on the number of unique clones remaining in the library after enrichment, there are two paths. If the number is between 1 and ~100, the enzymes are evaluated for activity individually. By contrast, if the number of unique clones is >100 further characterization is performed at the population level Characterization To characterize the sequences at a population level, the output from activity enrichment above which contains hundreds to thousands of unique active enzymes is used. This same pool is subjected to the high-throughput emulsion-base enrichment as described above multiple times in parallel under several different conditions. In this multi-condition characterization, performance is assessed across several important parameters, such as: substrate state (soluble v. surface adsorbed), low and high temperature stability and catalytic performance, resistance to protease degradation, sensitivity to divalent cation concentration. The enrichment at low and high conditions for each of these parameters is performed, enriching the population for the best performance under each condition. Long-read NGS (LoopSeq™, LOOP Genomics) is then used to measure differential enrichment of sequences across these parameters. These differences in enrichment correlate to the performance of these variants in assay.

The sequence data, structural inference, and performance data are used to build a machine learning training set that can be used to predict which regions, motifs and structural classes will perform well under different conditions. This model is used as an input to drive molecule optimization.

Example 3: Molecule Optimization-Optimization of Lipase Enzyme for Activity at Low Temperature The output of the molecule discovery and characterization unit contains information about sequence identity and performance. Data on which families of enzymes, regions within the enzyme, and specific amino acid residues are associated with higher low-temperature performance is acquired. Existing sequence databases are searched for natural variants that are predicted to have good performance based on the algorithm. This information is used to build lipase gene libraries that target these regions. The libraries are transformed into an appropriate host and screen for those with the highest performance at the goal temperature of 15° C. If the library diversity is <1,000, screening is performed in traditional microtiter format, and if the diversity is large, screening is performed in microfluidic plugs or drops.

In either case, protein variants are expressed in bacteria, and then a lysate of these bacteria is exposed to a fluorogenic substrate. The population is enriched for variants with the highest activity at low temperatures. The enriched population is then sequenced and compared to the starting population. Both the positively and negatively-enriched sequences feed into a model that allows prediction of the best-performing enzyme in our system. This data is used to design subsequence libraries where key residues affecting performance are saturated. The highest-performing sequences are also recombined either by gene shuffling or by synthesizing promising combinations. The cycle of enrichment and library refinement is repeated until the performance target is reached.

Example 4: Strain Optimization Via Random Mutagenesis

The methods, compositions, and systems herein may enable strain optimization in a high-throughput format with high predictability. In one example, a strain expressing a molecule of interest may be subject to non-targeted mutagenesis, e.g., random mutagenesis. The random mutagenesis may comprise subjecting the strain expressing the molecule of interest to mutagens and/or random genetic changes (e.g., transposon mutagenesis, MAGE, genome shuffling, random recombination, non-homologous end joining, etc), thereby generating a library of mutagenized cells. Such a library may comprise, for example, >10,000 variants or >1,000,000 variants. The library of mutagenized cells (considered a generation) may be expanded via growth in liquid culture and cells may be treated to ensure the population is comprised of single cells.

Figure 4:
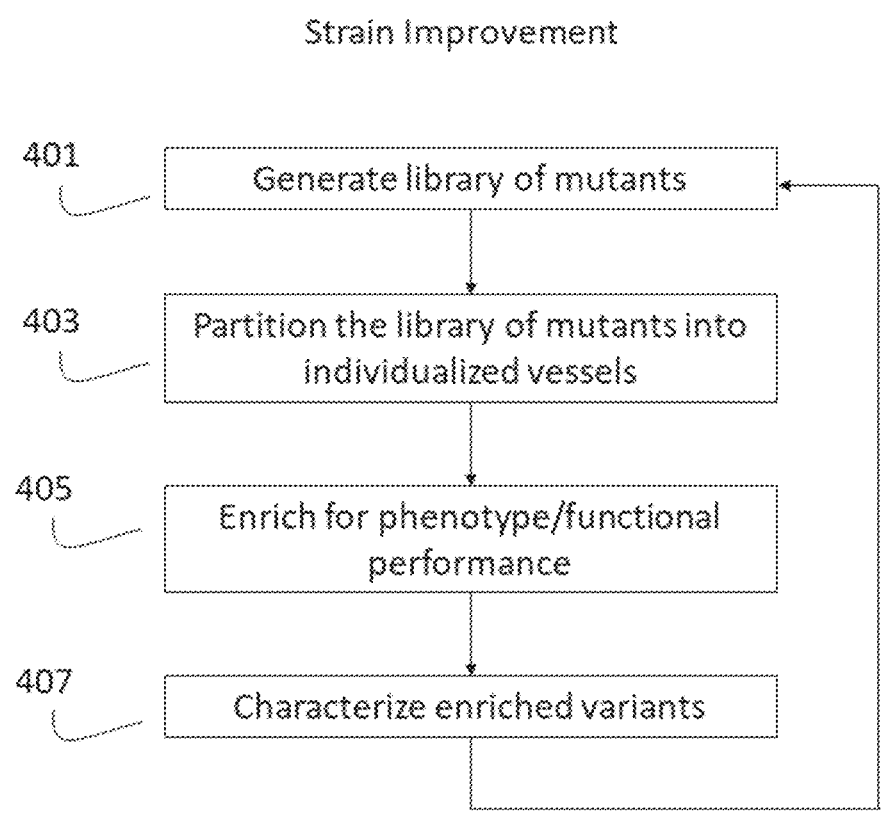
FIG. 4 shows an example workflow for strain optimization.

FIG. 4 schematically shows an example workflow for performing strain optimization. In process 401 a library of mutants (or mutagenized cells, also referred to herein as genetic variants) may be generated, as described above. In process 403, the library of mutants may be partitioned into individual reaction vessels (e.g., microreactors). In some instances, individual or single cells are partitioned into the individual vessels. The partitioning may be assisted by a computer implemented method having a feedback loop that ensures all the individual vessels contain a predefined volume (within a range), which may be useful in ensuring consistent growth between the individual cells in the individual vessels. In some instances, image recognition may be used to ensure the desired number of cells is loaded into the individual vessels.

The individual vessels comprising the individual cells may be subjected to conditions that mimic fermentation conditions (e.g., temperature, carbon source, pH, media components, aeration, etc). The individual vessels may comprise the same set of fermentation conditions, or they may comprise different fermentation conditions, or a subset of the individual vessels may comprise the same set of fermentation conditions and another subset of the individual vessels may comprise a different set of fermentation conditions. The cells in the individual vessels may be incubated in the individual vessels for a time frame that enables cell growth and/or production of the molecule of interest. Growth within microbioreactors may be monitored through imaging and computer image recognition.

In process 405, the individual vessels may be screened, and based on the screening, one or more cells (of the set of partitioned mutagenized cells) may be enriched (e.g., an improved cell or a cell expressing a desired phenotype may be selected). In one example, the individual vessels or contents therein may be placed into a device that allows for addition of reagents and control of a reaction time. Detection of the molecule(s) of interest may be performed, and based on the detection, one or more cells may be selected. The detection and/or selection may be performed in an automated fashion. For example, the systems described herein may comprise computer-implemented methods that can make decisions on which individual vessels contain cells that display a phenotype of interest by interrogating for molecule production and molecule activity through the addition of detection reagents. The addition of detection reagents can also be used to change the environment of the molecule of interest (e.g., pH, ionic strength, ion types, substrates, inhibitors, enzymes, competitors). Such a change of the environment may be useful in generating conditions that reflect on the amount of molecule produced and/or the function of the molecule produced. At a defined and controllable time after addition of reagents, the individual vessels may be assessed for the molecule(s) of interest via a spectroscopic signal. Instrument design and computer controlled feedback of the instrument may control the timing, reagent additions, assessment of molecule production and decision making on which microbioreactors meet the criteria for selection. In some instances, a PID algorithm may be used to prevent erroneous sorting decisions due to instrument drift (e.g., due to slight deviations in mechanical instruments, liquid viscosities, temperature, etc.) during the course of the strain optimization.

Optionally, following sorting, e.g., upon instrument decision to keep a particular library member (e.g., mutagenized cell), the selected cell may be removed from its vessel by the system and retained in an environment that maximizes organism viability (e.g., under sufficient nutrients conditions, salt conditions, temperature, aeration, etc.). The cells can be expanded via cell growth, and optionally, another round (e.g., processes 403, and 405, and in some instances, 407) of screening and enrichment may be performed. Optionally, for each round of screening and enrichment that is performed, more stringent conditions may be applied (e.g., lower oxygen, lower nutrient, change in pH, etc.). Alternatively or in addition to, more stringent performance criteria (e.g., increased expression, catalytic activity, etc.) may be applied during enrichment. Subsequently, the enriched cells may be characterized in process 407. The enriched cells may be analyzed, e.g., via sequencing or via phenotypic screening. For example, the enriched cells may be analyzed to confirm for the desired phenotypes under additional testing conditions. Cells that retain the desired phenotypes may then be entered into another iteration ("generation") of genetic changes and screenings (e.g., processes 401, 403, and 405) and the processes iterated in a recursive cycle until a performance criterion is met.

Figure 5:
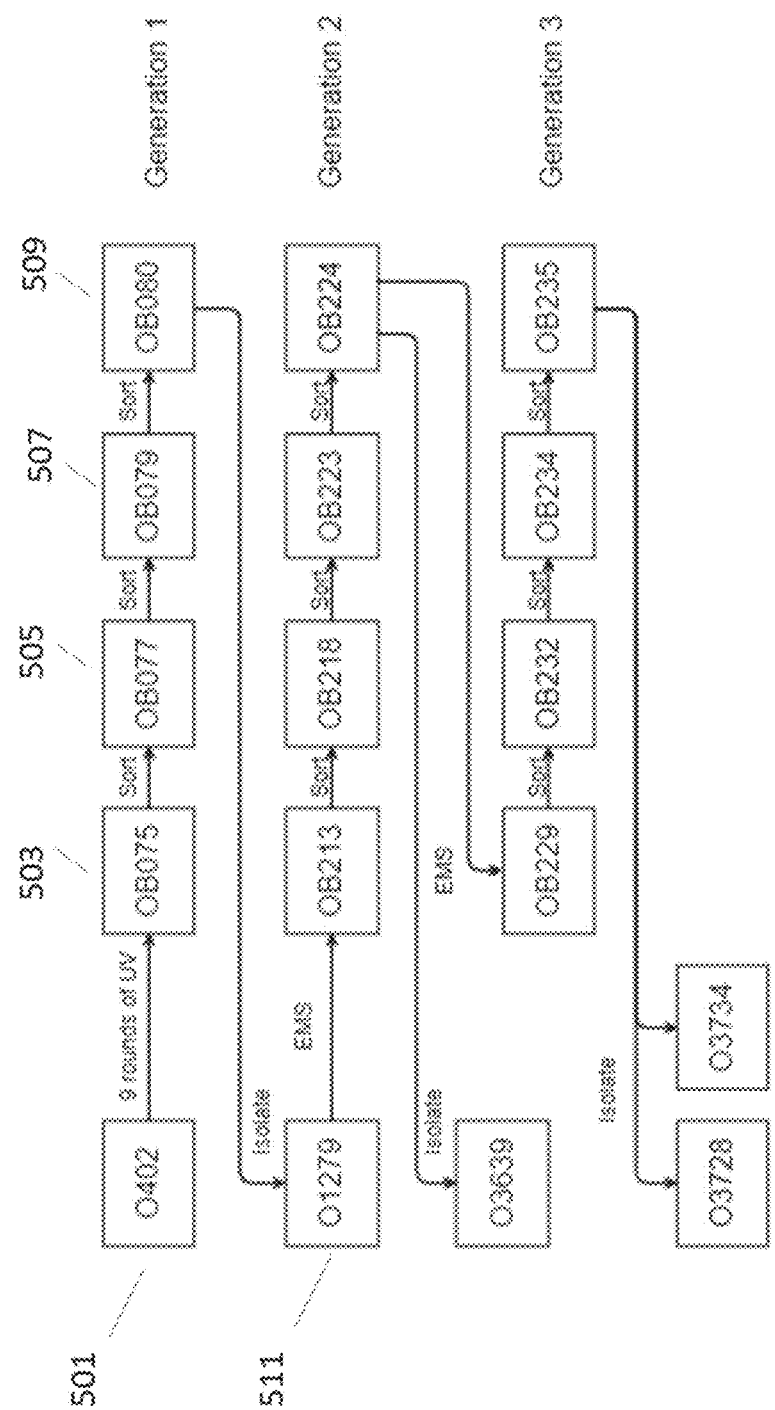
FIG. 5 shows an example workflow for strain optimization comprising multiple rounds of enrichment.

FIG. 5 shows an example workflow of a strain optimization process described herein. A parent strain or cell line 501 is subjected to random mutagenesis (9 rounds of ultraviolet radiation exposure) to provide a first library of mutants, e.g., mutagenized cells 503. The first library of mutagenized cells 503 is subjected to a first round of enrichment, which first round may comprise partitioning, optional growth, and sorting. The mutants with a functional performance above a threshold may be collected and then subject to another round of enrichment to generate a second library of mutagenized cells 505. The process of enrichment may be performed for any number of useful rounds to obtain subsequent library of mutagenized cells (e.g., 507 and 509). The final library of mutagenized cells may then be collected and characterized (e.g., via sequencing) and additional mutagenesis may be performed, e.g., as described herein, thus starting a new generation. The new generation parent strain or cell line 511 may additionally be subjected to mutagenesis (exposure to ethyl methyl sulfonate (EMS)), enriched for one or more rounds, and the process repeated until an optimal or desired performance criteria is met.

Figure 6A:
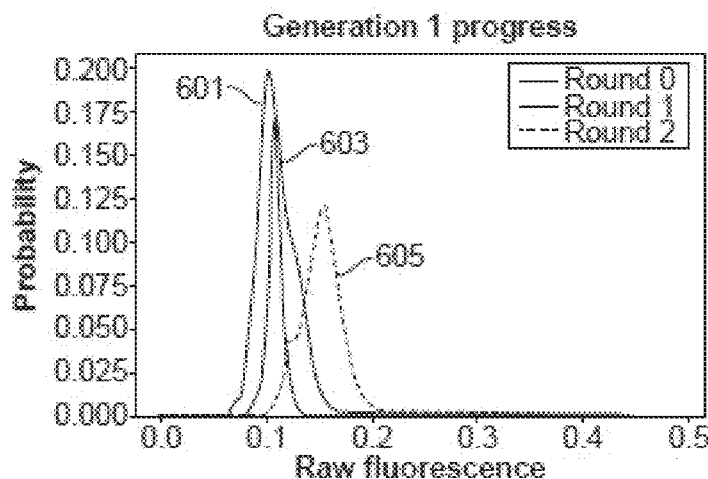
FIGS. 6A-6C show example data obtained from strain optimization.
Figure 6B:
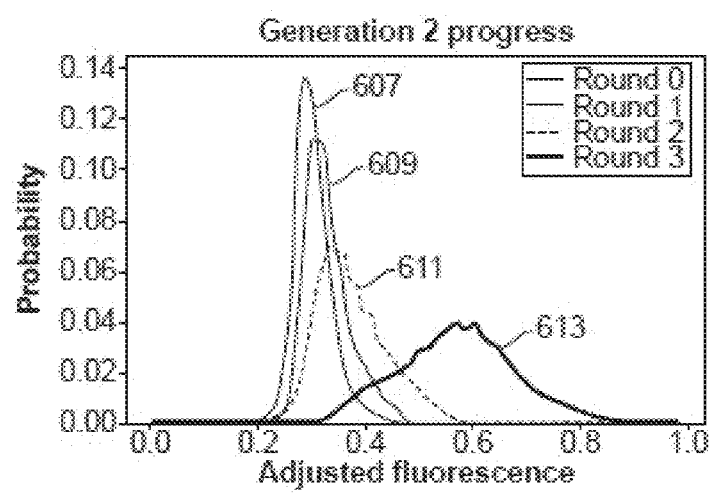
Figure 6C:
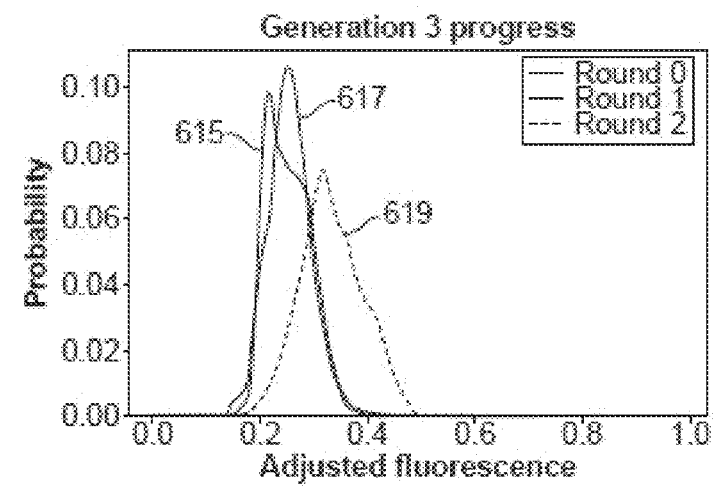

FIGS. 6A-6C shows example data from performing strain optimization over three generations (e.g., three cycles of mutagenesis, partitioning, enriching, and characterization). FIG. 6A shows a histogram of the fluorescence intensity (x-axis), which may be representative of an amount or quantity of a molecule (e.g., enzyme) of interest, of individual cells prior to strain optimization 601, which may not be mutagenized, and after one round 603 of enrichment and after two rounds 605 of enrichment within a first generation. The highest performing variants (e.g., the variants that produce the greatest quantity of the molecule of interest) of the last round of enrichment of the first generation are then further mutagenized, thereby beginning a second generation of mutants. FIG. 6B shows a histogram of the fluorescence intensity (x-axis) of individual cells prior to strain optimization 607, after one round 609, after two rounds 611, and after three rounds 613 during the second generation. FIG. 6C shows a histogram of the fluorescence intensity (x-axis) of individual cells prior to strain optimization 615, after one round 617, after two rounds 619, and after three rounds 613 during the third generation. As can be seen in FIGS. 6A-6C, additional rounds of enrichment lead to increased (right-shifted) intensity, indicative of enhanced performance.

Figure 7:
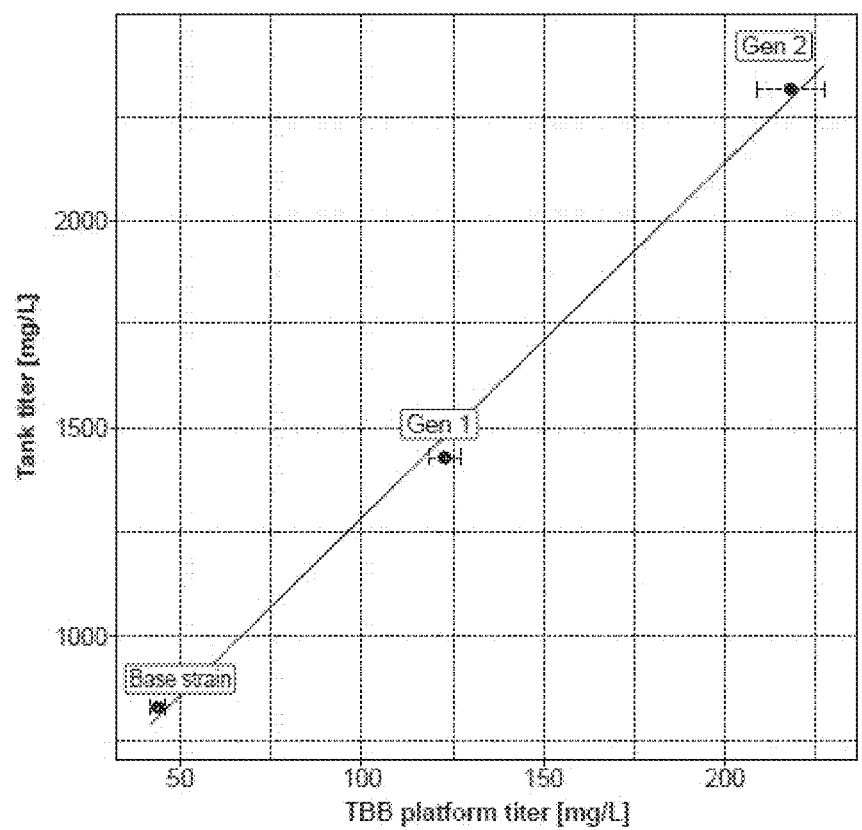
FIG. 7 shows a plot of the amount of a molecule of interest across generations.

FIG. 7 shows an example plot of the concentration of product produced of a mutant obtained over two generations of mutagenesis and multiple rounds of sorting and enrichment, as cultured in a reaction vessel (e.g., as used for high-throughput screening and sorting) (x-axis) as compared to culturing in a bulk-fed batch reactor (y-axis). Each point represents the amount (concentration) of product produced from a single mutant (the highest expressing mutant) from each generation when grown in both microreactor and batch growth conditions. As indicated in FIG. 7, the relationship between the production of the molecule (e.g., protein) of interest in a microreactor scales approximately linearly with the production of the molecule (e.g., protein) of interest on batch scales, thus indicating that the strain optimization process may obtain results on the micro-scale that are representative of batch growth conditions. Altogether, these data indicate how strain optimization may be an effective tool for improving functional performance of a strain in a high-throughput manner.

Example 5: Strain Optimization Via Natural Diversity Libraries

The methods, compositions, and systems herein may enable strain optimization in a high-throughput format with high predictability. In an example, a strain expressing a molecule of interest may be subjected to genetic changes based on large natural and/or engineered diversity sets. The diversity sets may include promoters, 5' untranslated regions, ribozymes, RNA stability sequences, secretion peptides, signal peptides, fusion proteins, DNA binding domains, protein-protein binding regions, codon optimized genes, codon randomized gene, 3' untranslated regions, terminators, non-homologous end joining, etc., which may be introduced to a plurality of cells to generate a library of mutagenized cells. The library of mutagenized cells may comprise, for example, >1,000 variants, >10,000 variants, >100,000 variants, or >1,000,000 variants. The library of mutagenized cells (considered a generation) may be expanded via growth in liquid culture and cells may be treated to ensure the population is comprised of single cells.

To begin a round within a generation, individual cells of the library of mutagenized cells may be partitioned in individual vessels, subjected to fermentation conditions, optionally monitored, and screened as described above (see Example 4) and as shown in FIGS. 4-5.

Figure 8:
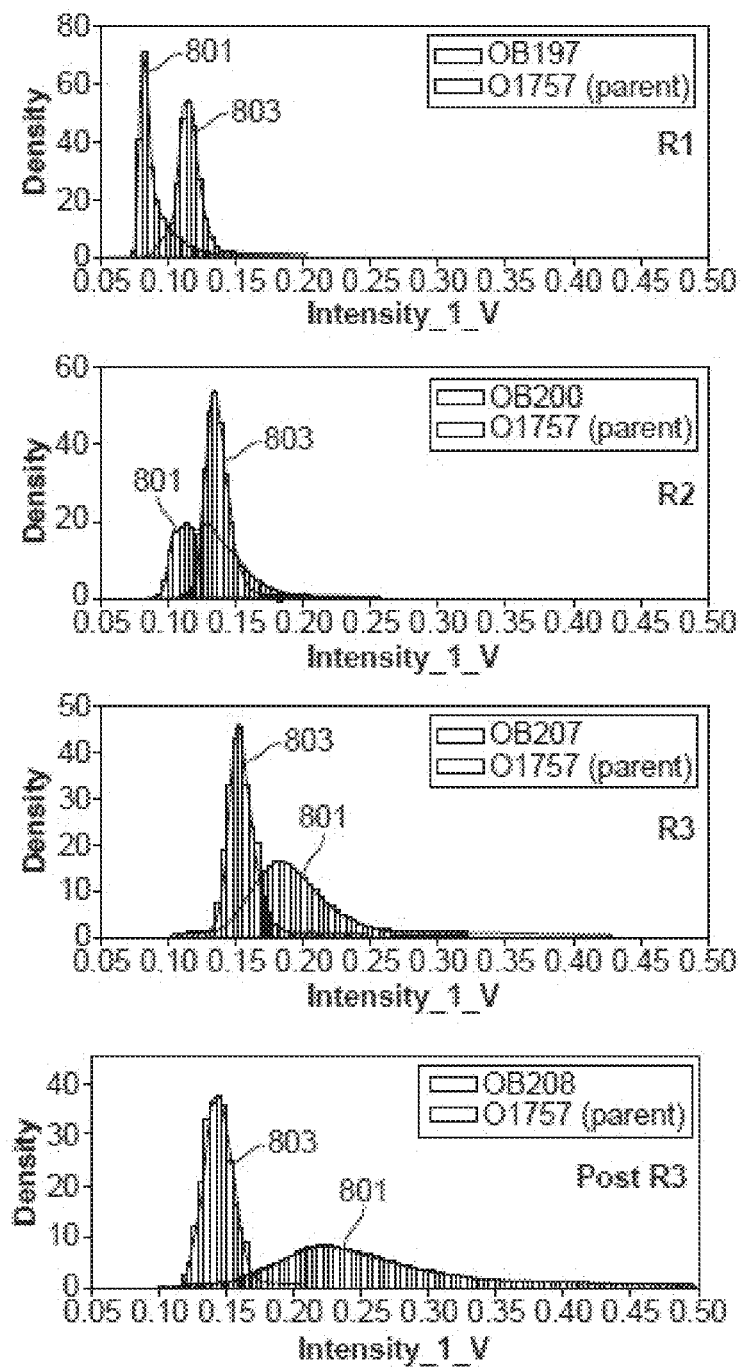
FIG. 8 shows example data obtained from strain optimization across rounds of enrichment within a generation.

FIG. 8 shows example data from performing strain optimization over a single generation (e.g., one cycle of mutagenesis). In FIG. 8, each panel shows a histogram plot of intensity, representative of a quantity of a produced molecule of interest. The non-mutagenized cell 803 (e.g., the cell prior to introduction of mutations) maintains a relatively similar peak profile, as expected, whereas the average of the overall population of mutagenized cells 801 (e.g., mutagenized cells that are partitioned, cultured, and screened) obtained from each round initially show a lower production of the molecule of interest, likely due to deleterious effects of the mutagenesis. Over subsequent rounds of screening (e.g., partitioning, enriching, and optional characterization), the average of the overall population of mutagenized cells 801 show a right-hand peak shift, indicating an increase in intensity, and thus quantity of produced molecule of interest, as a result of the strain optimization and screening process.

Figure 9:
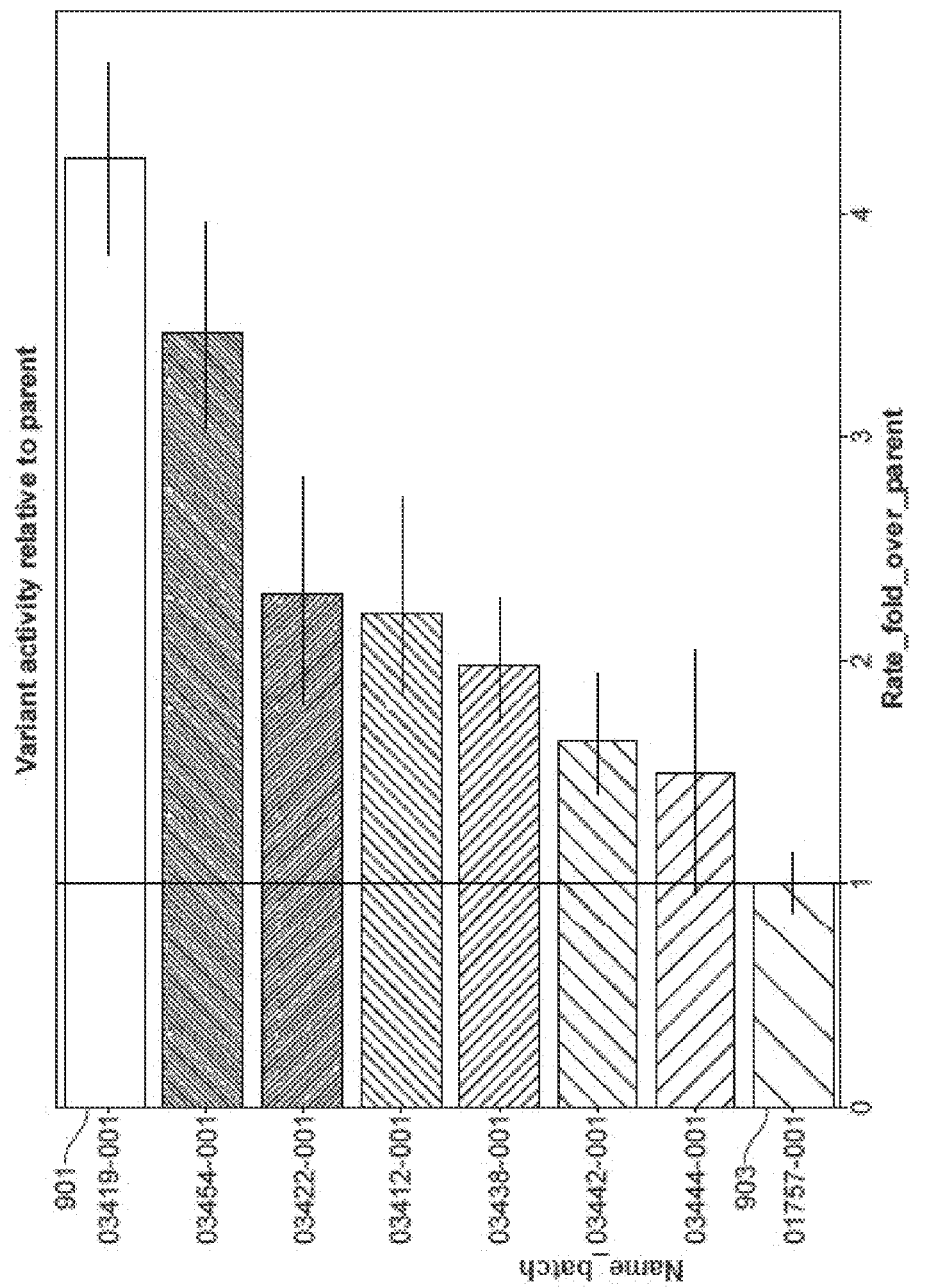
FIG. 9 shows example data obtained from strain optimization across rounds of enrichment.

FIG. 9 shows the result of a plate-based assay for measuring the molecule of interest across each round of screening within a single generation. Each bar represents a measurement of the fold change of intensity (representative of quantity of the produced molecule of interest) over the course of the strain optimization, normalized to the non-mutagenized cell production 903. The mutagenized cells 901 (e.g., mutagenized cells that are partitioned, cultured, and screened) obtained from each round (each set of bars) increase in intensity per round, thus indicating a higher quantity of produced molecule of interest, as a result of the strain optimization process.

Example 6: Molecule Discovery Via Targeted or Non-Targeted Mutagenesis

The methods, compositions, and systems herein may enable molecule discovery, e.g., discovery of genetic variants that result in an improved phenotype. In an example, a cell may be subjected to mutagenesis (e.g., targeted or non-targeted mutagenesis) to generate a library of mutagenized cells. Such a library may comprise, for example, >10,000 variants or >1,000,000 variants. The library of mutagenized cells may be expanded via growth in liquid culture and cells may be treated to ensure the population is comprised of single cells.

Figure 10:
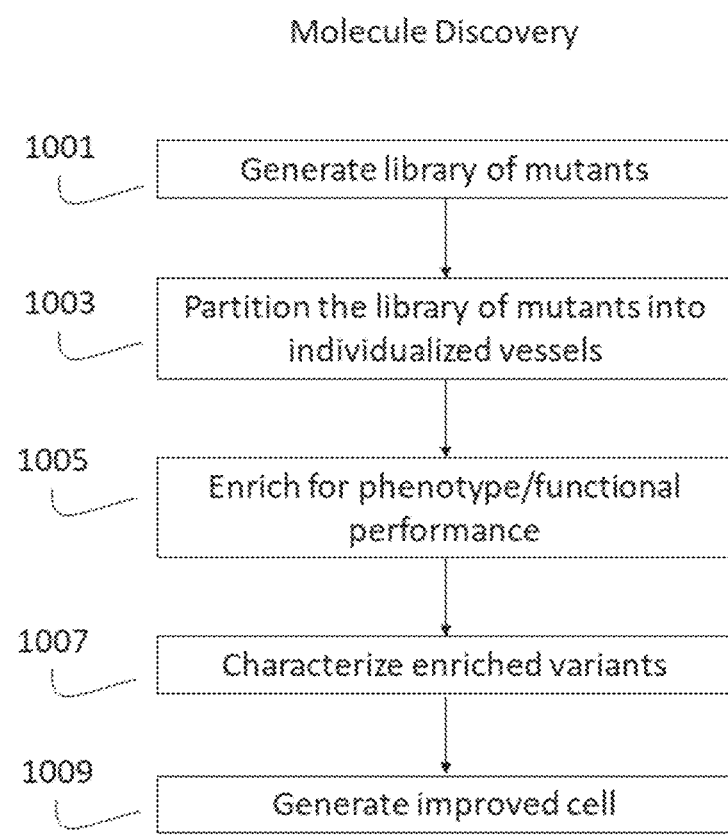
FIG. 10 shows an example workflow for molecule discovery.

FIG. 10 schematically shows an example workflow for performing molecule discovery. The process may be generally similar to that shown in FIG. 4. In process 1001 a library of mutants (or mutagenized cells, also referred to herein as genetic variants) may be generated, as described above, e.g., using targeted or non-targeted mutagenesis. In process 1003, the library of mutants may be partitioned into individual vessels (e.g., microreactors). In some instances, individual or single cells are partitioned into the individual vessels. The partitioning may be assisted by a computer implemented method having a feedback loop that ensures all the individual vessels contain a predefined volume (within a range), which may be useful in ensuring consistent growth between the individual cells in the individual vessels. In some instances, image recognition may be used to ensure the desired number of cells is loaded into the individual vessels.

The individual vessels comprising the individual cells may be subjected to conditions that mimic fermentation conditions (e.g., temperature, carbon source, pH, media components, aeration, etc). The individual vessels may comprise the same set of fermentation conditions, or they may comprise different fermentation conditions, or a subset of the individual vessels may comprise the same set of fermentation conditions and another subset of the individual vessels may comprise a different set of fermentation conditions. The cells in the individual vessels may be incubated in the individual vessels for a time frame that enables cell growth and/or production of the molecule of interest. Growth within microbioreactors may be monitored through imaging and computer image recognition.

In process 1005, the individual vessels may be screened, and based on the screening, one or more cells (of the set of partitioned mutagenized cells) may be enriched (e.g., an improved cell or a cell expressing a desired phenotype may be selected). In one example, the individual vessels or contents therein may be placed into a device that allows for addition of reagents and control of a reaction time. Detection of the molecule(s) of interest may be performed, and based on the detection, one or more cells may be selected. The detection and/or selection may be performed in an automated fashion. For example, the systems described herein may comprise computer-implemented methods that can make decisions on which individual vessels contain cells that display a phenotype of interest by interrogating for molecule production and molecule activity through the addition of detection reagents. The addition of detection reagents can also be used to change the environment of the molecule of interest (e.g., pH, ionic strength, ion types, substrates, inhibitors, enzymes, competitors). Such a change of the environment may be useful in generating conditions that reflect on the amount of molecule produced and/or the function of the molecule produced. At a defined and controllable time after addition of reagents, the individual vessels may be assessed for the molecule(s) of interest via a spectroscopic signal. Instrument design and computer controlled feedback of the instrument may control the timing, reagent additions, assessment of molecule production and decision making on which microbioreactors meet the criteria for selection. In some instances, a PID algorithm may be used to prevent erroneous sorting decisions due to instrument drift (e.g., due to slight deviations in mechanical instruments, liquid viscosities, temperature, etc.) during the course of the strain optimization.

Optionally, following sorting, e.g., upon instrument decision to keep a particular library member (e.g., mutagenized cell), the selected cell may be removed from its vessel by the system and retained in an environment that maximizes organism viability (e.g., under sufficient nutrients conditions, salt conditions, temperature, aeration, etc.). The cells can be expanded via cell growth, and optionally, another round (e.g., processes 1003, and 1005) of screening and enrichment may be performed. Optionally, for each round of screening and enrichment that is performed, more stringent conditions may be applied (e.g., lower oxygen, lower nutrient, change in pH, etc.). Alternatively or in addition to, more stringent performance criteria (e.g., increased expression, catalytic activity, etc.) may be applied during enrichment. Subsequently, the enriched cells may be characterized in process 1007. The enriched cells may be analyzed, e.g., via sequencing or via phenotypic screening. For example, the enriched cells may be analyzed to confirm for the desired phenotypes under additional testing conditions.

In some instances, the characterization of process 1007 comprises gene and/or protein sequencing. For example, the enriched cells may be subjected to DNA or RNA sequencing to determine or identify the presence of one or more mutations or to characterize the mutations. In some instances, based on the DNA or RNA sequence, the amino acid sequence of the resultant transcribed or translated peptide of the DNA or RNA sequence can be determined. The amino acid sequence may be compared to that of the parent (e.g., non-mutagenized) cell to determine specific changes in amino acid sequences (e.g., which residues of a peptide are different) of a protein of interest. Further validation studies may be performed, for example, by transforming or transducing the parent (e.g., non-mutagenized) cell or a daughter cell (e.g., a mutagenized cell derived from the parent cell) with the gene sequence of the enriched variant. Such a process 1009, e.g., of enriching for variants, identifying their nucleic acid or protein sequences, and then transferring those mutants to a cell (e.g., via transformation or transduction), such that the cell comprises those identified nucleic acid or protein sequences of the enriched variants, may result in a cell with improved phenotype or functional performance.

Figure 11:
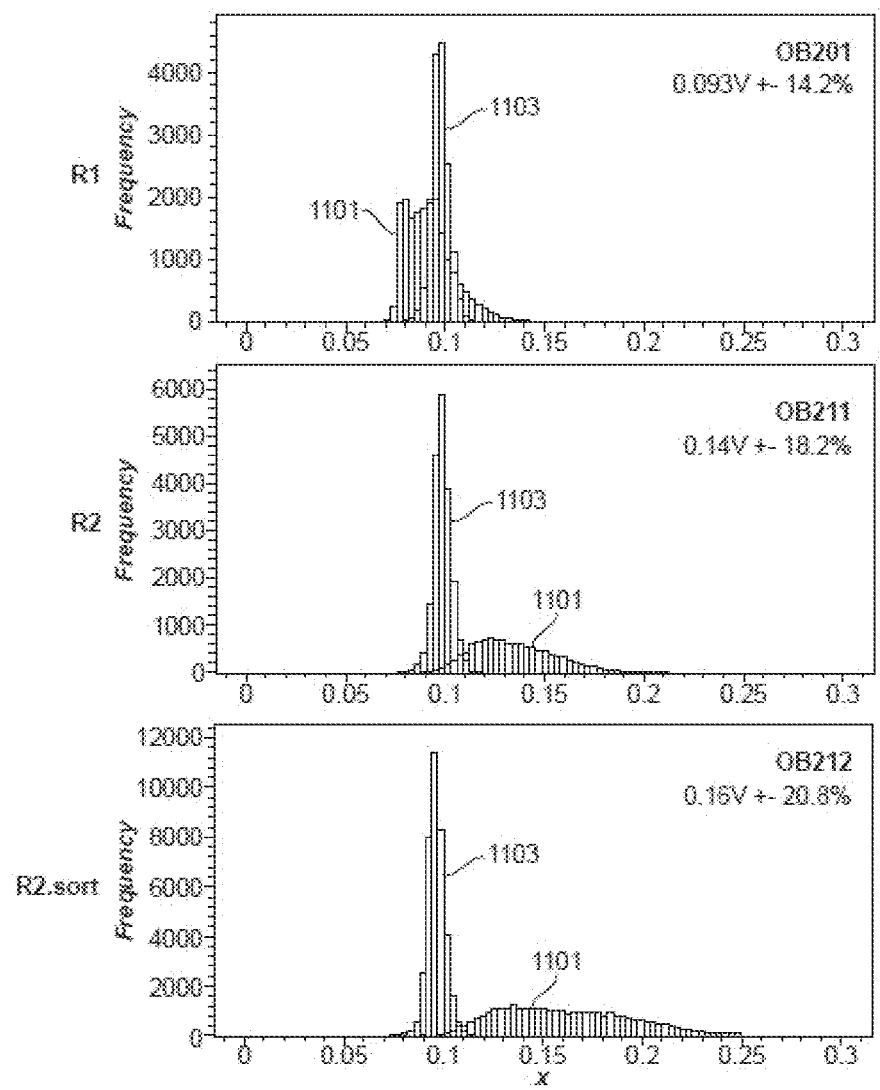
FIG. 11 shows example data obtained from molecule discovery across rounds of enrichment within a generation.

FIG. 11 shows example data from performing molecule discovery using a workflow as described above and as shown in FIG. 10. The molecule discovery is performed for a single generation (e.g., one cycle of mutagenesis) over two rounds of partitioning, enriching, and optional characterization. In FIG. 11, each panel shows a histogram of the intensity, representative of a quantity of a produced molecule of interest (e.g., secreted protein). In an example, the produced molecule of interest may be a reporter protein (e.g., green fluorescent protein), which expression may be driven by a SigA promoter. The higher the activity of SigA, the more reporter protein is expressed, and the higher the signal intensity. The non-mutagenized cell 1103 (e.g., the cell prior to introduction of mutations) maintains a relatively similar peak profile, whereas the mutagenized cells 1101 (e.g., mutagenized cells that are partitioned, cultured, and screened) obtained from each round illustrate a right-hand shift, indicating an increase in intensity, and thus quantity of produced molecule of interest, as a result of the molecule discovery process. The bottom panel shows mutagenized cells 1101 after a second round of gating and sorting, indicating that following sorting and enrichment, an increased phenotype of interest (e.g., higher intensity representative of a greater quantity of a produced molecule of interest) is observed.

Following or concurrently with screening, a population of mutagenized cells may be sorted. For example, the systems described herein may comprise a computer readable medium that sets a threshold functional performance parameter (e.g., a minimum intensity, minimum concentration, minimum quantity of the molecule of interest, etc.) by which the cells are sorted. Cells that are above the threshold may be sorted or enriched in a first bin for further analysis, whereas cells that are below the threshold may be sorted in a second bin.

The cells in the first bin may be further analyzed for mutations, e.g., to determine the nucleic acid or protein sequences, which may help determine which mutations result in improved functional performance.

FIG. 12 shows a table of example mutations obtained from the molecule discovery process, e.g., from the process outlined in FIG. 10. Each mutation is in the format XNNNY, where X indicates the original amino acid residue (e.g., the residue of the non-mutated cell), NNN indicates the amino acid position of the mutation, and Y indicates the mutated original amino acid residue. For example "T31R" refers to a mutation from threonine to arginine on the 31st amino acid residue. Each of the mutations in FIG. 12 are for SigA transcription factor, which can modify the expression of a protein of interest or reporter protein (e.g., GFP). The mutants shown in FIG. 12 lead to higher expression of the protein of interest or reporter protein. The mutations are demonstrated to result in an improved functional performance (e.g., increased secretion or activity of the SigA transcription factor and thus increased expression and intensity of the reporter protein) and are a result of enrichment during the molecule discovery process.

Figure 13:
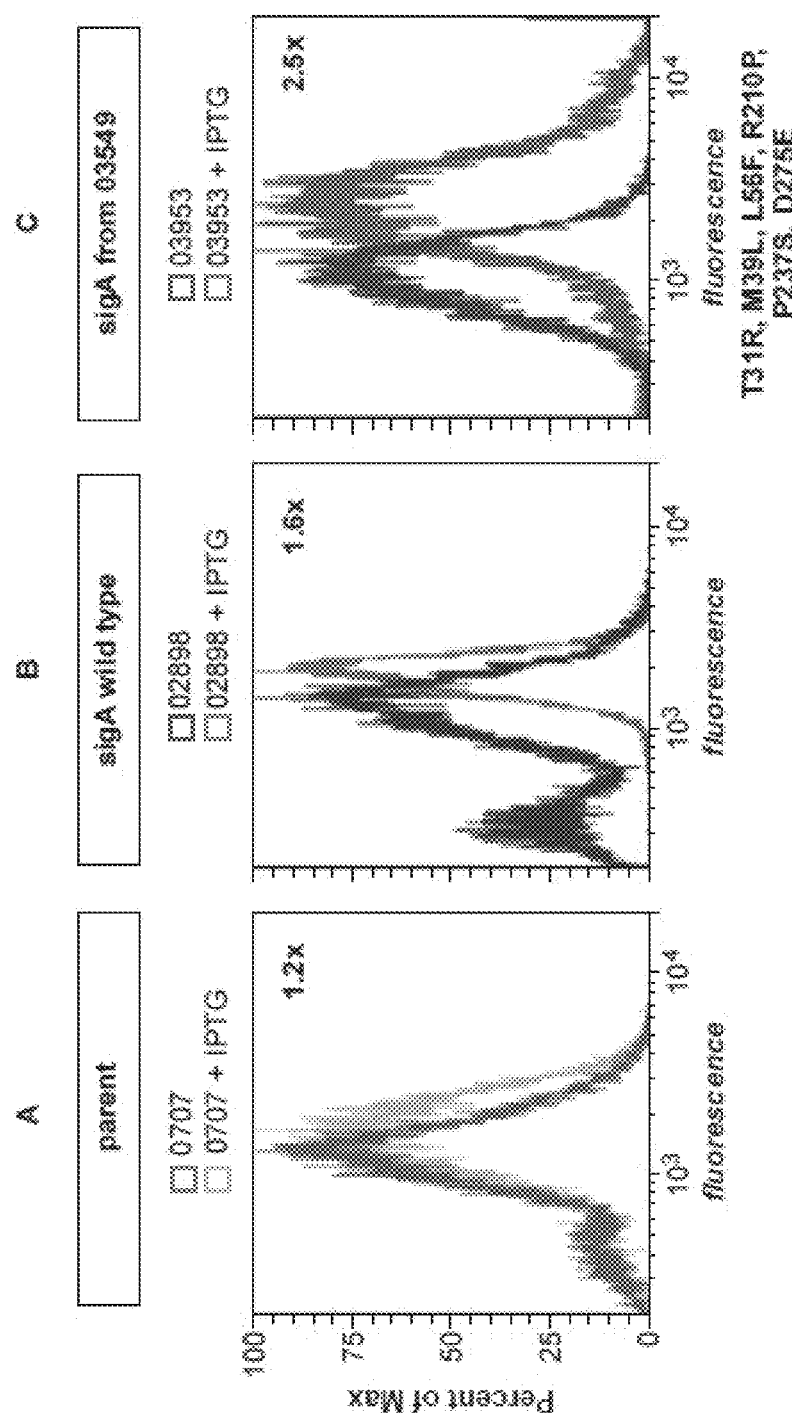
FIG. 13 shows example data of improving functional performance of a molecule through using the molecule discovery process.
Figure 13:
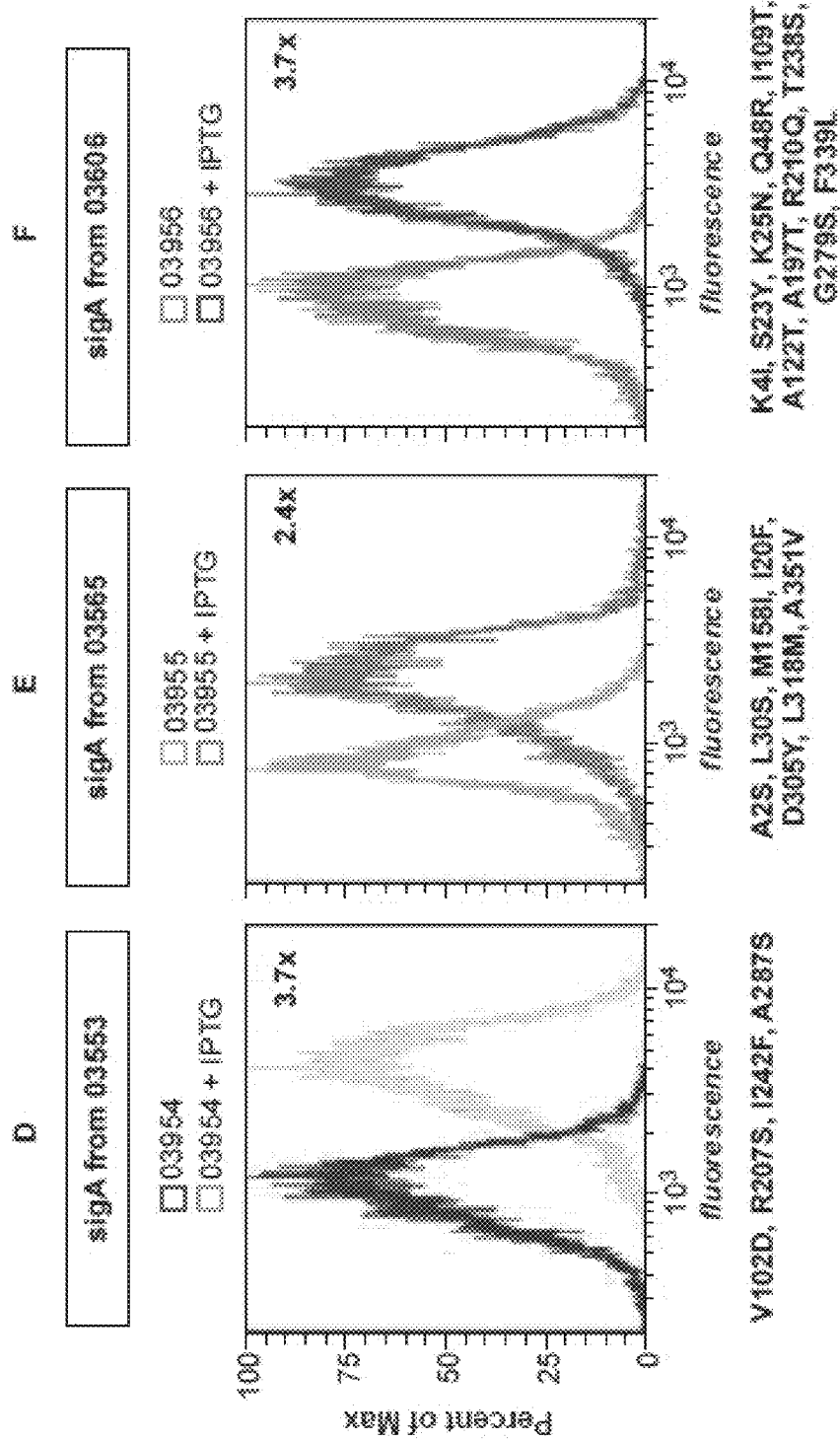

FIG. 13 shows example data of introducing the derived mutations of FIG. 12 into a cell. In such an example, the cell may be a non-mutagenized cell, a parent cell, or a mutagenized cell. The cell may be transformed with a gene variant to express a protein mutant identified in FIG. 12 (e.g., a SigA mutant, which may promote expression of a protein of interest or a reporter protein, such as GFP). Expression of the protein mutant (e.g., SigA mutant) may be controlled by an inducible promoter. FIG. 13 Panel A shows a control group, in which the parent (e.g., non-mutagenized cell) may be transformed with a plasmid vector control with an inducible promoter. Induction of expression (e.g., by turning on the inducible promoter, shown in this example as adding Isopropyl β-d-1-thiogalactopyranoside, IPTG) results in no appreciative difference in fluorescent signal of the reporter protein, indicative of little to no change in expression or activity of the transcription factor (e.g., SigA), as expected. In Panel B, a cell expressing the reporter protein (e.g., GFP, which expression is driven by SigA) which naturally produces the transcription factor (e.g., SigA) is transformed with a plasmid with an inducible gene encoding for the transcription factor (e.g., SigA). Forced expression of the wild-type transcription factor (e.g., SigA) that is already naturally produced by the cell results in an increase in the reporter protein signal, indicative of some increase in quantity or activity of the transcription factor (e.g., SigA). In Panels C-F, expression of the reporter protein (e.g., GFP) is increased for each of the introduced, induced SigA mutants. In each panel of Panels C-F, a cell is transformed with a plasmid comprising one or more of the enriched SigA mutants listed in FIG. 12. Each of the mutant groups (Panels C-F) result in increased expression of the reporter protein upon induction of the inducible promoter by 2.5×, 3.7×, 2.4×, and 3.7×, respectively. Altogether, these results indicate that the molecule discovery systems and methods described herein may be a useful in identification of genetic variants that result in an improved functional performance, e.g., increased protein expression or activity.

Example 7: Molecule Improvement Using Machine Learning

The methods, compositions, and systems herein may enable molecule improvement or optimization e.g., generation of an improved molecular variant. In one example, the methods herein may be used for generating an improved polymer variant, such as a peptide or protein.

Figure 14:
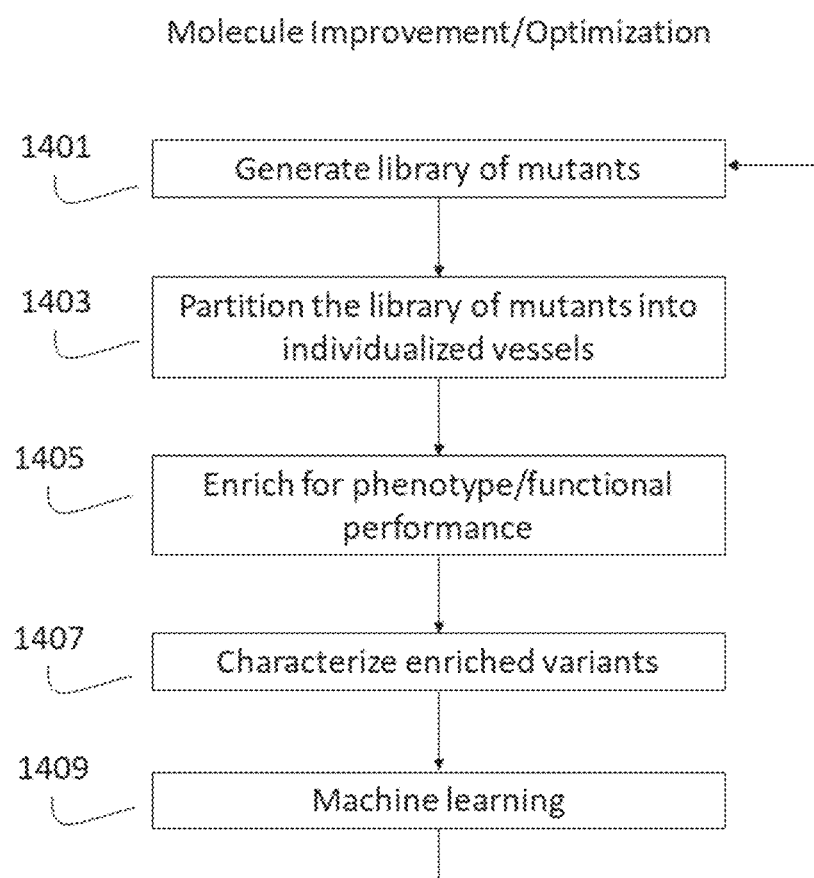
FIG. 14 shows an example workflow for molecule optimization.

FIG. 14 schematically shows an example workflow for performing molecule improvement to generate an improved polymer variant (e.g., protein). In process 1401, a library of polymer variants is generated. In one example, the library of polymer variants may comprise a library of mutants of a gene encoding an enzyme; such a library of mutants may be generated via mutagenesis. For example, for a given gene, mutagenesis may be performed to obtain a Site saturation library (SSL), in which every amino acid position in the protein is changed to all 20 amino acids. Further mutagenesis may be performed, e.g., via gene shuffling and error-prone PCR to obtain the library of mutants. The library of mutants may then be transformed into a plurality of cells (e.g., an appropriate bacterial expression host) such that a cell comprises a single mutant (e.g., a sequence encoding a polymer, peptide, or protein variant).

In process 1403, the library of mutants may be partitioned into individualized vessels. Optionally, the vessels may comprise conditions sufficient for the cells to grow and produce the polymer (e.g., protein or enzyme) of interest. After several hours of growth and production, the cells may then be screened and enriched in process 1405. During the screening, an enzyme substrate in a reaction buffer may be added to each individualized vessel. The individualized vessels are incubated for a precise time and then a function of the polymer variants may be determined to obtain function data. For example, the enzyme activity may be measured (e.g., by measuring the amount of a fluorescent or luminescent product). Concurrently or subsequent to the measurement, the library of mutants may be sorted into several functional gates (e.g., 4 gates) that represent different performances (e.g., enzymatic activity). In some instances, a subset of the library of mutants may not be sorted, which may be set aside as a control population or a comparison (e.g., pre-enrichment) group.

In some examples, the total number of cells measured may be greater than the number of unique polymer variants. For example, following growth and culturing of the variants (e.g., mutagenized cells comprising genetic variants), each variant may comprise a clonal population of the variant. After partitioning single cells into the individual reaction vessels, multiple copies of the same variant may be present within the individual reaction vessels. As such, the total number of cells assayed may be 50-100 times the number of unique variants expected in the library.

In process 1407, the sorted cells, e.g., from one or more of the of the sort gates may be further analyzed. For example, each cell (or population of cells) may be isolated from the vessel, and the DNA sequenced, e.g., using next-gen sequencing to obtain sequence data. The unsorted cells may also be sequenced. Based on the sequence data, the abundance of each mutant, both before (from the unsorted cells) and after (from the sorted cells) enrichment, can be calculated. Enrichment data, e.g., an enrichment factor, for each sequence may be calculated by comparing the abundance of each mutant in the sorted cells to the abundance of each mutant in the unsorted cells. As the enrichment factor is proportional to the functional performance (e.g., catalytic activity) of the mutant, the enrichment factors can be used as a functional label for each sequence in the library. This sequence/function-labeled dataset can then be input and/or analyzed in process 1409 using a machine learning (ML) approach to make recommendations for future designs. The ML algorithms may produce many thousands of designs (e.g., genetic or polymer variants) that are predicted to have a high performance. These predicted variants may then be synthesized (e.g., using oligonucleotide arrays) and assembled into plasmids for transformation into an expression host. The molecule improvement or optimization process (e.g., processes 1401, 1403, 1405, 1407, and 1409) may then be iterated several times (e.g., 2-4 generations) to yield highly active mutants.

Figure 15:
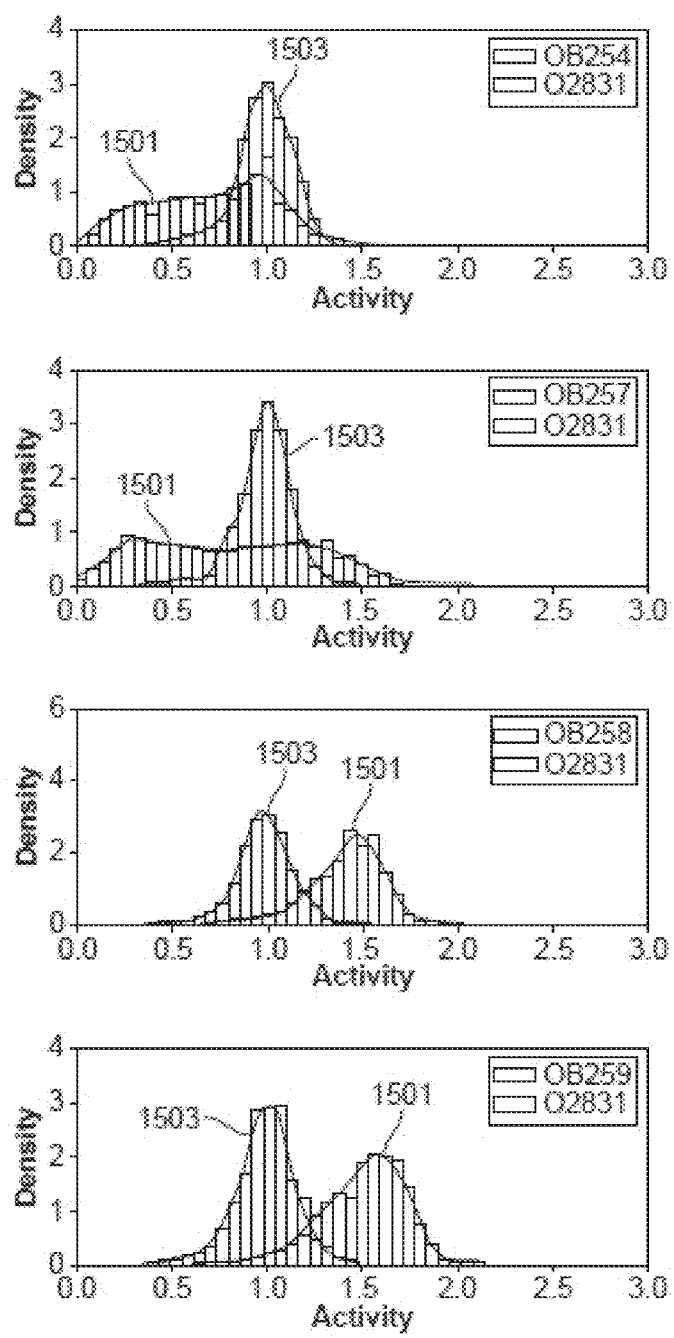
FIG. 15 shows example data obtained from molecule optimization across rounds of enrichment within a generation.

FIG. 15 shows example data of the molecule optimization process. Each panel shows a histogram plot of intensity, representative of a performance (e.g., enzymatic activity level) of a produced molecule of interest over subsequent rounds of enrichment (from top to bottom). The non-mutagenized cell 1503 (e.g., the cell prior to introduction of mutations) maintains a relatively similar peak profile, as expected, whereas the mutagenized cells 1501 (e.g., mutagenized cells that are partitioned, cultured, and screened) obtained from each round initially show a lower performance (e.g., activity level) of the molecule of interest, likely due to deleterious effects of the mutagenesis. Over subsequent rounds of screening (e.g., partitioning, enriching, and optional characterization), the mutagenized cells 1501 show a right-hand peak shift, indicating an increase in intensity, and thus activity level of produced molecule of interest, as a result of the molecule optimization process.

Figure 16:
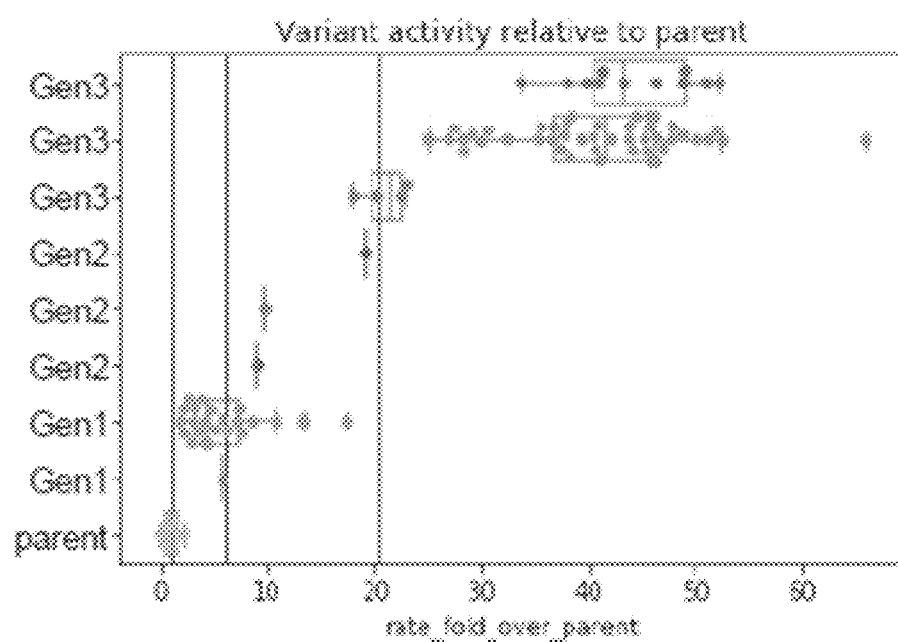
FIG. 16 shows example data obtained from the molecule optimization process across generations.

FIG. 16 shows scattered box plots of the variant activity over the generations of molecule optimization. As can be seen in FIG. 16, the variant activity (x-axis) increases within rounds of several generations.

Example 8: Instrument Control

Also described herein are instrument control algorithms, which may be useful in correcting for drift, noise, and/or creep that occur within the system or during the methods described herein.

In some examples, a computer readable medium may comprise one or more feedback algorithms to control the frequency of partitioning (e.g., controlling droplet frequency), which may include, for example, automatically adjusting flow rates, pressure, temperature, etc. In another example, the sorting gates, e.g., the threshold parameter, may be adjusted to account for noise, creep, etc. For example, during sorting or enrichment, a threshold gate (e.g., minimum intensity threshold or top percentage of a library) may be set. The feedback algorithm may automatically alter or modulate the gating parameters to maintain a collection ratio.

Figure 17:
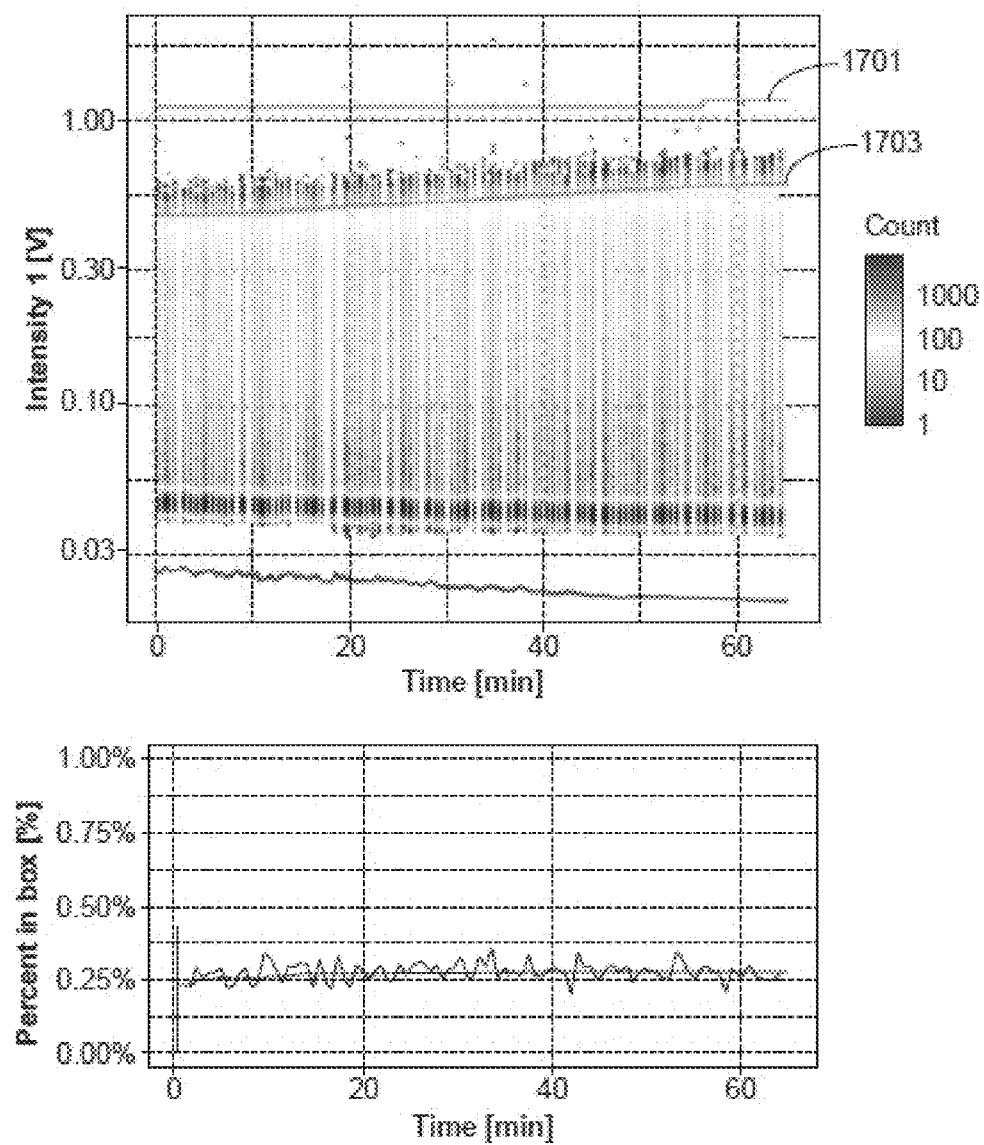
FIG. 17 shows example data of an algorithm for preventing or accounting for drift in the systems described herein.

FIG. 17 shows example data of a sorting gate feedback system. The top plot shows signal intensity of the measured variants as a product of time. The top line 1701 and bottom line 1703 indicate gates. As signal diverts higher and higher with time (drifts with time), the percentage of variants that are enriched between the gates maintains constant, due to the feedback algorithm adjusting for the adjustment of the two gates 1701 and 1703. The bottom plot shows the percentage of variants within the collection range as a function of time, which maintains relatively constant.

Embodiments

In some cases, the present disclosure provides a method according to the following embodiments:
Embodiment 1. A method for generating an improved polymer variant, the method comprising
(a) obtaining a dataset comprising
i) sequence data comprising data on polymer variant sequences; and ii) enrichment data based on an abundance of the polymer variant sequences in a sample sorted based on the polymer variant function; and (b) applying one or more machine learning algorithms to the dataset to design an improved polymer variant.

Embodiment 2. The method of embodiment 1, wherein the polymer variant sequences comprise sequences i) in an unsorted sample and ii) in the sample sorted based on the polymer variant function, wherein the sample sorted based on the polymer variant function and the unsorted sample are from a common sample.

Embodiment 3. The method of embodiment 2, wherein the enrichment data are further based on an abundance of the polymer variant sequences in the unsorted sample.

Embodiment 4. The method of embodiment 3, wherein the abundance of the polymer variant sequences in the sample sorted based on the polymer variant function comprises a sequence count.

Embodiment 5. The method of embodiment 3 or 4, wherein the abundance of the polymer variant sequences in the unsorted sample comprises a sequence count.

Embodiment 6. The method of any one of embodiments 3-5, wherein the enrichment data comprise an enrichment factor for a first polymer variant sequence based on i) an abundance of the first polymer variant sequence in the polymer variant sequences in the unsorted sample and ii) an abundance of the first polymer variant sequence in the polymer variant sequences in the subset of the sample sorted based on the polymer variant function.

Embodiment 7. The method of embodiment 6, wherein the enrichment factor is a functional label for the first polymer variant sequence.

Embodiment 8. The method of any one of embodiments 1-7, wherein the method comprises performing multiple generations of (a) and (b), wherein the improved polymer variant of (b) is used to generate the dataset of (a) in a subsequent generation of the multiple generations.

Embodiment 9. The method of embodiment 8, wherein the multiple generations are at least 3 or 4 generations.

Embodiment 10. The method of any one of embodiments 1-9, wherein the polymer variant comprises a protein.

Embodiment 11. The method of embodiment 10, wherein the protein comprises an enzyme.

Embodiment 12. The method of embodiment 11, wherein the function comprises an activity of the enzyme.

Embodiment 13. The method of any one of embodiments 1-12, wherein the improved polymer variant comprises at least 1000 improved polymer variants.

Embodiment 14. The method of any one of embodiments 1-13, wherein the polymer variant sequences comprise nucleic acid sequences encoding the polymer variant.

Embodiment 15. The method of embodiment 1, further comprising, before obtaining the dataset, providing a library of cells comprising the polymer variant, wherein the polymer variant comprises polymer variants.

Embodiment 16. The method of embodiment 15, further comprising generating the library of cells comprising the polymer variants.

Embodiment 17. The method of embodiment 16, wherein the generating comprises providing a site saturation nucleic acid molecule library (SSL) encoding proteins with each of 20 naturally-occurring amino acids at each position.

Embodiment 18. The method of embodiment 17, further comprising performing gene shuffling and error-prone polymerase chain reaction (epPCR) on the SSL to generate nucleic acid molecules encoding the polymer variants.

Embodiment 19. The method of embodiment 18, further comprising transforming the nucleic acid molecules encoding the polymer variants into cells to generate the library of cells.

Embodiment 20. The method of embodiment 19, wherein the cells comprise bacterial cells.

Embodiment 21. The method of embodiment 15, further comprising partitioning the library of cells to generate a plurality of partitions.

Embodiment 22. The method of embodiment 21, wherein each partition of the plurality of partitions comprises on average one or fewer cells.

Embodiment 23. The method of embodiment 21, further comprising growing the library of cells in the plurality of partitions.

Embodiment 24. The method of embodiment 23, further comprising expressing the polymer variants in the library of cells in the plurality of partitions.

Embodiment 25. The method of embodiment 15, further comprising determining the polymer variant function using the library of cells comprising the polymer variants.

Embodiment 26. The method of embodiment 25, wherein the polymer variants comprise proteins.

Embodiment 27. The method of embodiment 26, wherein the proteins comprise enzymes.

Embodiment 28. The method of embodiment 27, wherein the determining the polymer variant function comprises using an enzyme substrate and a reaction buffer Embodiment 29. The method of embodiment 28, wherein the polymer variant function comprises enzyme activity.

Embodiment 30. The method of embodiment 29, wherein the enzyme activity produces a fluorescent product.

Embodiment 31. The method of embodiment 15, further comprising sorting a subset of the library of cells comprising the polymer variants based on the polymer variant function to provide the sample sorted based on the polymer variant function and an unsorted sample.

Embodiment 32. The method of embodiment 31, wherein the function is an amount of enzyme activity.

Embodiment 33. The method of embodiment 31, wherein the sorting comprises sorting the subset of the library of cells into a plurality of groups based on the function.

Embodiment 34. The method of embodiment 32, wherein the plurality of groups is at least 4 groups.

Embodiment 35. The method of embodiment 31, wherein the subset of the library of cells comprises from about 50 times to about 100 times a number of unique polymer variants expected to exist in the library of cells.

Embodiment 36. The method of embodiment 31, further comprising using the sample sorted based on the polymer variant function to determine the polymer variant sequences.

Embodiment 37. The method of embodiment 36, wherein the sample sorted based on the polymer variant function comprises a fiducial sequence.

Embodiment 38. The method of embodiment 36, wherein using the sample sorted based on the polymer variant function to determine the polymer variant sequences comprises purifying nucleic acid molecules from the sample sorted based on the polymer variant function.

Embodiment 39. The method of embodiment 31, further comprising purifying nucleic acid molecules from the unsorted sample.

Embodiment 40. The method of embodiment 39, wherein the purifying nucleic acid molecules from the sample sorted based on the polymer variant function occurs separately from the purifying nucleic acid molecules from the unsorted sample.

Embodiment 41. The method of embodiment 31, further comprising sequencing the nucleic acid molecules from the sample sorted based on the polymer variant function and the nucleic acid molecules from the unsorted sample to provide the polymer variant sequences.

Embodiment 42. The method of embodiment 41, wherein the sequencing comprises next generation sequencing.

Embodiment 43. The method of embodiment 41, further comprising using the polymer variant sequences to determine the abundance of the polymer variant sequences i) in the sample sorted based on the polymer variant function and ii) in the unsorted sample.

Embodiment 44. The method of embodiment 43, further comprising using the abundance of the polymer variant sequences i) in the sample sorted based on the polymer variant function and ii) in the unsorted sample to determine the enrichment data.

Embodiment 45. The method of embodiment 44, wherein the enrichment data comprises an enrichment factor Embodiment 46. The method of embodiment 1, further comprising synthesizing the improved polymer variant.

Embodiment 47. The method of embodiment 46, wherein the synthesizing comprises synthesis on an oligonucleotide array.

Embodiment 48. The method of embodiment 47, further comprising assembling the improved polymer variant into a vector.

Embodiment 49. The method of embodiment 48, wherein the vector is a plasmid.

Embodiment 50. The method of embodiment 48, further comprising introducing the vector into a host cell.

Embodiment 51. The method of embodiment 8, wherein (a) of a first generation of the multiple generations comprises performing saturation mutagenesis and epPCR to provide a library of cells;
wherein (a) of a second generation of the multiple generations comprises performing epPCR; and
wherein (a) of a third generation of the multiple generations comprises performing epPCR.

Embodiment 52. The method of embodiment 51, wherein each generation of the multiple generations comprises multiple rounds of the sorting of.

Embodiment 53. A non-transitory computer readable medium comprising instructions thereon which when executed by a computer processor cause the computer processor to perform the method of any one of embodiments 1-14.

Embodiment 54. A system comprising a computer processor and the non-transitory computer readable medium of embodiment 53.

Embodiment 55. A method for generating an improved cell comprising
(a) generating a library of mutagenized cells;
(b) partitioning the library of mutagenized cells into a plurality of partitions to yield partitioned mutagenized cells;
(c) screening the partitioned mutagenized cells for a phenotype;
(d) based on the screening, selecting an improved cell from the partitioned mutagenized cells using a threshold gate;
(e) using a feedback controller (i) in (b) to maintain a frequency of generation of the plurality of partitions or (ii) in (d) to regulate the threshold gate; and
(f) using the improved cell to repeat steps (a)-(d).

Embodiment 56. The method of embodiment 55, wherein the method comprises using the feedback controller to maintain a frequency of generation of the plurality of partitions.

Embodiment 57. The method of embodiment 56, wherein the plurality of partitions comprise a plurality of droplets.

Embodiment 58. The method of embodiment 57, wherein the feedback controller adjusts a flow rate to maintain a frequency of generation of the plurality of droplets.

Embodiment 59. The method of embodiment 55, wherein the method comprises using the feedback controller to regulate the threshold gate.

Embodiment 60. The method of embodiment 59, wherein the feedback controller raises or lowers the threshold gate.

Embodiment 61. The method of embodiment 59, wherein the feedback controller regulates the threshold gate to select a target percentage of the partitioned mutagenized cells.

Embodiment 62. The method of embodiment 55, wherein the feedback controller is a proportional-integral-derivative (PID) algorithm.

Embodiment 63. The method of embodiment 59, wherein the feedback controller accounts for deviations in a mechanical instrument, liquid viscosity, or temperature.

Embodiment 64. The method of embodiment 55, wherein generating the library of mutagenized cells comprises contacting the cell with a mutagen.

Embodiment 65. The method of embodiment 55, wherein generating the library of mutagenized cells comprises transposon mutagenesis, multiplex automated genomic engineering (mage), genome shuffling, random recombination, or non-homologous end joining.

Embodiment 66. The method of embodiment 55, wherein the generating the library of mutagenized cells comprises introducing heterologous genetic elements into a cell.

Embodiment 67. The method of embodiment 64, wherein the heterologous genetic elements comprise a promoter, 5' untranslated region, ribozyme, RNA stability sequence, nucleic acid encoding a secretion peptide, nucleic acid encoding a signal peptide, nucleic acid encoding a fusion protein, nucleic acid encoding a DNA binding domain, nucleic acid encoding protein-protein binding region, nucleic acid encoding a codon optimized gene, a 3' untranslated region, or a terminator.

Embodiment 68. The method of embodiment 55, wherein the mutagenized cells comprise at least 1000 cells, at least 10,000 cells, or at least 1,000,000 cells.

Embodiment 69. The method of embodiment 55, further comprising expanding the library of mutagenized cells before (b).

Embodiment 70. The method of embodiment 67, wherein the expanding occurs in liquid culture.

Embodiment 71. The method of embodiment 55, wherein the partitioning is controlled by computer readable medium.

Embodiment 72. The method of embodiment 55, wherein each partition of the plurality of partitions of comprises a volume of liquid within a predefined range.

Embodiment 73. The method of embodiment 55, further comprising imaging each partition of the plurality of partitions before (c).

Embodiment 74. The method of embodiment 71, further comprising ensuring a partition of the plurality of partitions comprises a desired number of mutagenized cells of the mutagenized cells based on the imaging.

Embodiment 75. The method of embodiment 55, further comprising subjecting the plurality of partitions to cell growth conditions between (b) and (c).

Embodiment 76. The method of embodiment 55, wherein the subjecting comprises controlling temperature, carbon source, pH, media components, or aeration of a subset of partitions of the plurality of partitions.

Embodiment 77. The method of embodiment 55, further comprising monitoring cell growth in the plurality of partitions subjected to the cell growth conditions using imaging.

Embodiment 78. The method of embodiment 55, wherein the screening comprises adding a detection reagent to each partition of the plurality of partitions.

Embodiment 79. The method of embodiment 76, wherein the detection reagent changes an environment of each partition of the plurality of partitions.

Embodiment 80. The method of embodiment 76, wherein the detection reagent comprises a pH modifying agent, an ionic strength modifying agent, an ion, a substrate, an inhibitor, and enzyme, or a competitor.

Embodiment 81. The method of embodiment 55, wherein the library of mutagenized cells encodes a molecule of interest Embodiment 82. The method of embodiment 79, wherein the screening comprises detecting the molecule of interest;
measuring an activity of the molecule of interest, wherein the activity is optionally a catalytic activity, wherein the catalytic activity optionally produces a fluorescent product;
determining an amount of the molecule of interest; or determining a function of the molecule of interest.

Embodiment 83. The method of embodiment 55, wherein the screening comprises performing multiple screens.

Embodiment 84. The method of embodiment 55, wherein the multiple screens comprise applying a more stringent threshold for the phenotype of interest in a subsequent screen of the multiple screens relative to a prior screen of the multiple screens.

Embodiment 85. The method of embodiment 55, wherein the selecting a partition comprises performing a spectroscopic measurement.

Embodiment 86. The method of embodiment 55, wherein the selecting a partition comprises applying a threshold.

Embodiment 87. The method of embodiment 55, wherein (f) comprises removing a mutagenized cell from a selected partition to yield the improved cell.

Embodiment 88. The method of embodiment 87, further comprising maintaining viability of the mutagenized cell.

Embodiment 89. The method of embodiment 87, further comprising growing the mutagenized cell.

Embodiment 90. The method of embodiment 55, further comprising screening the improved cell for the phenotype of interest.

Embodiment 91. The method of embodiment 55, wherein the mutagenized cells comprise bacteria.

Embodiment 92. A computer readable medium comprising instruction thereon that when executed by a computer processor cause the computer processor to perform steps (b)-(e) of embodiment 55.

Embodiment 93. A system comprising a computer processor and the computer readable medium of embodiment 92.

Embodiment 94. An integrated system for sorting desired biological variants comprising two or more integrated units selected from the group consisting of: a strain optimization unit, a molecule optimization unit and a molecule discovery unit, wherein
(a) the strain optimization unit comprises a plurality of distinct strain optimization reaction vessels, each with a different strain optimization genetic variant or a fermentation condition(s);
(b) the molecule optimization unit comprises a plurality of distinct molecule optimization reaction vessels, each with a different target protein variant or application condition(s);
(c) the molecule discovery unit comprises a plurality of distinct molecule discovery reaction vessels, each with a different discovery molecule or application condition (s).

Embodiment 95. The integrated system of embodiment 94, wherein the two or more units are integrated via a computer readable medium that is capable of performing one or more of the following functions:
(i) storage of data sets from each of the two or more integrated units in a data repository;
(ii) set a threshold parameter for data to be delivered to the data repository;
(iii) instruct each of the two or more units to repeat an input diversity screen.

Embodiment 96. The integrated system of embodiment 94, wherein the two or more units are integrated via a computer readable medium comprising a machine learning algorithm that integrates data from each of the two or more units for the desired sorting biological variants.

Embodiment 97. The integrated system of embodiment 96, wherein the machine learning algorithm comprises: Elastic-Net Regularized Generalized Linear Models (GLMNET), Support Vector Machine Regression (SVM), Random Forest (RF), Extreme Gradient Boosting (XG-Boost), Multilayer Perceptron (MLP), or a Convolutional Neural Network (CNN).

Embodiment 98. The integrated system of embodiment 94, wherein each of the strain optimization reaction vessels, the molecule optimization reaction vessels, and/or the molecule discovery reaction vessels comprise an average of no more than 1 cell.

Embodiment 99. The integrated system of embodiment 94, wherein each of the strain optimization reaction vessels, the molecule optimization reaction vessels, and/or the molecule discovery reaction vessels comprise an average of more than 1 cell.

Embodiment 100. The integrated system of embodiment 99, wherein the average of more than 1 cell per well is a clonal population.

Embodiment 101. The integrated system of embodiment 99, wherein the average of more than 1 cell per well comprises a diverse cell population.

Embodiment 102. The integrated system of embodiment 94, wherein each of the strain optimization reaction vessels, the molecule optimization reaction vessels, and/or the molecule discovery reaction vessels comprise an average of 10-100 cell.

Embodiment 103. The integrated system of embodiment 97, wherein the strain optimization unit, the molecule optimization unit, and the molecule discovery unit are configured to perform single cell analysis.

Embodiment 104. The integration system of embodiment 99, wherein the strain optimization unit, the molecule optimization unit, or the molecule discovery unit are configured to perform multi-cell analysis.

Embodiment 105. The integrated system of embodiment 94, wherein the strain optimization unit, the molecule optimization unit and/or the molecule discovery unit is configured to screen at least 100 cells per minute.

Embodiment 106. The integrated system of embodiment 94, wherein each of the two or more integrated units comprise a consumable unit.

Embodiment 107. The integrated system of embodiment 106, wherein the consumable unit comprises a microfluidic device.

Embodiment 108. The integrated system of embodiment 107, wherein the microfluidic device comprises one or more functional elements selected from the group comprising: a droplet generator, a droplet condenser, a buffer reservoir, a cell incubator, a fluidic injector, a droplet splitter, a droplet sorter, a delay line, and a droplet singulator.

Embodiment 109. The integrated system of embodiment 94, wherein reaction vessels of the strain optimization reaction vessels, the molecule optimization reaction vessels, or the molecule discovery reaction vessels have a volume that is less than 1 microliter.

Embodiment 110. The integrated system of embodiment 94, wherein reaction vessels of the strain optimization reaction vessels, the molecule optimization reaction vessels, and/or the molecule discovery reaction vessels are in a nanowell array.

Embodiment 111. The integrated system of embodiment 94, wherein reaction vessels of the strain optimization reaction vessels, the molecule optimization reaction vessels, and/or the molecule discovery reaction vessels are droplets, plugs, or wells.

Embodiment 112. The integrated system of embodiment 94, further comprising a detector couple to said one or more units, wherein the detector is selected from the group consisting of: a mass spectrometer, a Raman spectrometer, a microscope, a cell counter, a fluorescence microscope, a light microscope, a flow cytometer, a mass spectrometer, a fluorescence plate reader, a near infrared (NIR) spectrophotometer, and a piezoelectric sensor.

Embodiment 113. The integrated system of embodiment 94, further comprising a reaction vessel movement actuator selected from the group consisting of: a robotic manipulator, a flow generator, an acoustic drop generator, optical tweezers, a thermal drop on demand, a piezoelectric drop on demand.

Embodiment 114. The integrated system of embodiment 94, wherein each of the different strain optimization genetic variant, each of the target protein variant is in a different cell and/or each of the target discovery molecule is in a different cell.

Embodiment 115. The integrated system of embodiment 94, wherein each strain optimization genetic variant is generated by random mutagenesis, Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), or a CRISPR guided DNA polymerase.

Embodiment 116. The integrated system of embodiment 115, wherein the random mutagenesis is saturation mutagenesis.

Embodiment 117. The integrated system of embodiment 94, wherein each target protein variant is generated by random mutagenesis, Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), or a CRISPR guided DNA polymerase.

Embodiment 118. The integrated system of embodiment 117, wherein the random mutagenesis is saturation mutagenesis or circular permutation.

Embodiment 119. The integrated system of embodiment 94, wherein each discovery molecule is a DNA encoded molecule found in a metagenomic library, a DNA-encoded library, a library of DNA from one or more microorganisms, or a Function Generator created library.

Embodiment 120. The integrated system of embodiment 94, wherein the strain optimization unit comprises a strain optimization library comprising a plurality of different genetic variants of a first strain.

Embodiment 121. The integrated system of embodiment 120, wherein the plurality of different genetic variants are classified by metabolic pathway.

Embodiment 122. The integrated system of embodiment 121, wherein the strain optimization library comprises phenotypic, sequence, and metabolic pathway data.

Embodiment 123. The integrated system of embodiment 122, wherein the strain optimization unit comprises a machine learning algorithm.

Embodiment 124. The integrated system of embodiment 123, wherein the machine learning algorithm identifies genetic variants that are optimized across multiple fermentation conditions.

Embodiment 125. The integrated system of embodiment 94, wherein each of the two or more units comprises a recursive cycle that comprises additional input of biological diversity or conditional diversity.

Embodiment 126. The integrated system of embodiment 94, wherein the plurality of discrete reaction volumes comprise at least $10^5$ discrete reaction volumes.

Embodiment 127. The integrated system of embodiment 94, wherein the application conditions comprise one or more of pH, substrate, reaction buffer, and temperature.

Embodiment 128. The integrated system of embodiment 94, wherein the fermentation conditions comprise one or more of pH, oxygenation, carbon source, buffer concentration, and temperature.

Embodiment 129. The integrated system of embodiment 120, wherein the strain optimization library comprises at least 100 different variants of the first strain.

Embodiment 130. The integrated system of embodiment 120, wherein the strain optimization library is generated by random mutagenesis of the strain.

Embodiment 131. The integrated system of embodiment 120, wherein the strain optimization library is selected from the group consisting of a whole-mutagenesis library, a genome-shuffled library, a targeted genomic library, and a transposon library.

Embodiment 132. The integrated system of embodiment 131, wherein the whole-genome mutagenesis library is a whole-genome random mutagenesis library.

Embodiment 133. The integrated system of embodiment 131, wherein the targeted genomic library is a promoter swap library.

Embodiment 134. The integrated system of embodiment 131, wherein the transposon library is a promoter insertion library.

Embodiment 135. The integrated system of embodiment 94, wherein the molecule optimization unit comprises a molecule optimization library comprising a plurality of different genetic variants of a first molecule.

Embodiment 136. The integrated system of embodiment 135, wherein the molecule optimization library is selected from the group consisting of a single gene random mutation library, a site saturation library, a small-insert metagenomic library, and a large-insert metagenomic library.

Embodiment 137. An integrated system for sorting desired biological variants comprising:
a biological diversity data stream, and
a conditional diversity data stream, wherein:
(a) each of the data streams is independently programmable,
(b) the biological diversity data stream comprises data from a screen of different genomic variants of a target protein or a strain expressing the target protein, and
(c) the conditional diversity data stream comprises data from a screen of different conditions of the strain and the target protein; and
(d) the biological diversity data stream and the conditional diversity data stream are integrated into an optimization unit that is configured to receive a target parameter and
i) direct the optimization unit to introduce additional biological diversity or conditional diversity until a target protein or a target strain is identified that matches the target parameter, or
ii) identify a target protein or a target strain that matches the target parameter.

Embodiment 138. The integrated system of embodiment 137, wherein the optimization unit comprises a computer readable medium that is capable of performing one or more of the following functions:
(i) storage of data sets from each of the biological diversity data stream and the conditional diversity data stream in a data repository;
(ii) set a threshold parameter for data to be delivered to the data repository;
(iii) instruct the optimization unit to repeat an input diversity screen.

Embodiment 139. The integrated system of embodiment 137, wherein the optimization unit comprises a computer readable medium comprising a machine learning algorithm that integrates the biological diversity data stream and the conditional diversity data stream for the desired sorting of biological variants.

Embodiment 140. The integrated system of embodiment 139, wherein the machine learning algorithm performs comprises: Elastic-Net Regularized Generalized Linear Models (GLMNET), Support Vector Machine Regression (SVM), Random Forest (RF), Extreme Gradient Boosting (XGBoost), Multilayer Perceptron (MLP), or a Convolutional Neural Network (CNN).

Embodiment 141. The integrated system of embodiment 137, wherein the strain optimization unit is configured to screen 100 different genomic variants of the target protein or the strain expressing the target protein per minute.

Embodiment 142. The integrated system of embodiment 137, wherein the strain optimization unit is configured to screen up 100 cells per minute.

Embodiment 143. The integrated system of embodiment 137, wherein each of the strain optimization unit comprise a consumable unit.

Embodiment 144. The integrated system of embodiment 143, wherein the consumable unit comprises a microfluidic device.

Embodiment 145. The integrated system of embodiment 144, wherein the microfluidic device comprises one or more functional elements selected from the group comprising: a droplet generator, a droplet condenser, a buffer reservoir, a cell incubator, a fluidic injector, a droplet splitter, a droplet sorter, a delay line, and a droplet singulator.

Embodiment 146. The integrated system of embodiment 144, wherein the microfluidic device comprises one or more reaction vessels.

Embodiment 147. The integrated system of embodiment 146, wherein the reaction vessels have a volume that is less than 1 microliter.

Embodiment 148. The integrated system of embodiment 146, wherein the reaction vessels are in a nanowell array.

Embodiment 149. The integrated system of embodiment 146, wherein the reaction vessels are drops, plugs, or wells.

Embodiment 150. The integrated system of embodiment 149, wherein the drops are water-in-oil drops.

Embodiment 151. The integrated system of embodiment 149, wherein the drops are water drops on a surface.

Embodiment 152. The integrated system of embodiment 146, wherein the reaction vessels comprise cells such that there is an average of about 1 cell every 2 or more reaction vessels.

Embodiment 153. The integrated system of embodiment 137, further comprising a detector coupled to said optimization units, wherein the detector is selected from the group consisting of: a mass spectrometer, a Raman spectrometer, a microscope, a cell counter, a fluorescence microscope, a light microscope, a flow cytometer, a mass spectrometer, a fluorescence plate reader, a near infrared (NIR) spectrophotometer and a piezoelectric sensor.

Embodiment 154. The integrated system of embodiment 137, further comprising a reaction vessel movement actuator selected from the group consisting of: a robotic manipulator, a flow generator, an acoustic drop generator, optical tweezers, a thermal drop on demand, a piezoelectric drop on demand.

Embodiment 155. The integrated system of embodiment 137, wherein each of the different genomic variants of the target protein is in a different cell.

Embodiment 156. The integrated system of embodiment 137, wherein each of the different genomic variants of the strain is generated by random mutagenesis, Multiplex Automated Genomic Engineering (MAGE), or CRISPR-enabled trackable genome engineering (CREATE), transposon based mutagenesis, genome shuffling, random recombination, non-homologous end joining, traceable multiplex recombineering (TRMR), or a CRISPR guided DNA polymerase.

Embodiment 157. The integrated system of embodiment 156, wherein the random mutagenesis is saturation mutagenesis or circular permutation.

Embodiment 158. The integrated system of embodiment 137, wherein each of the different genomic variants of the target protein variant is generated by random mutagenesis, Multiplex Automated Genomic Engineering (MAGE), or CRISPR-enabled trackable genome engineering (CREATE).

Embodiment 159. The integrated system of embodiment 158, wherein the random mutagenesis is saturation mutagenesis circular permutation.

Embodiment 160. A method for sorting for a final desirable genetic variant comprising:
combining data from a diversity screen of biologically diverse genetic elements comprising target protein genetic elements and strain genetic elements with data from a conditional screen of diverse conditions comprising target protein expression conditions and target protein performance conditions;
using the combined data set to identify the final desirable genetic variant.

Embodiment 161. The method of embodiment 160, wherein the conditional screen is performed on one or more genetic elements that are part of the diversity screen.

Embodiment 162. The method of embodiment 160, further comprising generating a first library of cells, each cell comprising a different genetic element from a first library of genetic elements.

Embodiment 163. The method of embodiment 162, further comprising generating a second library of cells, each cell comprising a different genetic element from a second library of genetic elements, wherein the first library of genetic elements and the second library of genetic elements are screened under multiple conditions independently.

Embodiment 164. The method of embodiment 163, wherein the first library of genetic elements and the second library of genetic elements are screened using next-generation sequencing (NGS) to identify mutations that are enriched under the multiple conditions.

Embodiment 165. The method of embodiment 160, wherein the diversity screen is performed on variants associated with strain optimization.

Embodiment 166. The method of embodiment 165, wherein the strain optimization results in an increased yield, improved fermentation conditions, increased viability, increased tolerance to ion concentrations.

Embodiment 167. The method of embodiment 166, wherein the increased yield is an increase in protein expression and/or an increase in cell proliferation.

Embodiment 168. The method of embodiment 160, wherein using the combined data set to identify the final desirable genetic variant further comprises a recursive cycle of:
(a) identifying one or more intermediate desirable genetic variants with desirable characteristics,
(b) obtaining a recombinant library based on the genetic elements of the one or more intermediate desirable genetic variants with desirable characteristics,
(c) screening the recombinant library with the conditional screen of diverse conditions, and
(d) identifying the final desirable genetic variant or (a) identifying one or more intermediate desirable genetic variants with desirable characteristics.

Embodiment 169. The method of embodiment 160, wherein the diversity screen is performed on variants associated with target protein discovery.

Embodiment 170. The method of embodiment 160, wherein the diversity screen is performed on variants associated with target protein optimization.

Embodiment 171. The method of embodiment 160, wherein each of the biologically diverse genetic elements is screened in parallel.

Embodiment 172. The method of embodiment 160, wherein each of the biologically diverse genetic elements is screened in series.

Embodiment 173. The method of embodiment 160, wherein the combined data set comprises data from one or more of a fluorogenic assay, a colorimetric assay, and a reporter cell-based assay.

Embodiment 174. The method of embodiment 173, wherein the fluorogenic assay is a direct assay, an indirect assay, a binding assay, or an in-vivo reporter assay.

Embodiment 175. The method of embodiment 160, wherein the conditional screen comprises adjusting temperature, media, oxygenation, salinity, pH, mixing, reaction time, metal ion concentration, additive concentration, feed rate, or a combination thereof.

Embodiment 176. The method of embodiment 160, wherein the conditional screen comprises performing two or more different conditions in tandem on a first genetic element.

Embodiment 177. The method of embodiment 160, wherein each of the diverse conditions are run in parallel.

Embodiment 178. The method of embodiment 160, wherein each of the diverse conditions are run in series.

Embodiment 179. The method of embodiment 160, further comprising generating a library of diverse genetic elements.

Embodiment 180. The method of embodiment 179, wherein the generating is performed by random mutagenesis, site directed mutagenesis, site saturation, or genome-shuffling.

Embodiment 181. The method of embodiment 179, further comprising introducing each genetic element from the library of diverse genetic elements into a cell or a cell-free system.

Embodiment 182. The method of embodiment 179, further comprising separating cells with genetic diversity from the library of diverse genetic elements into different reaction vessels such that each reaction vessel has no more than 1 cell.

Embodiment 183. The method of embodiment 182, wherein the reaction vessel is a drop, plug, or well.

Embodiment 184. The method of embodiment 160, wherein the desired genetic variant is associated with strain optimization, target molecule optimization, or molecule discovery from an environmental DNA or RNA library.

Embodiment 185. The method of embodiment 160, wherein the biological diversity is that of strain optimization.

Embodiment 186. The method of embodiment 185, wherein identifying the final desirable genetic variant comprises measuring one or more characteristics of a strain including expression level, cell viability, cell proliferation, and sensitivity to divalent cation concentration.

Embodiment 187. The method of embodiment 162, further comprising generating a library of modified strains by site-directed mutagenesis, random mutagenesis, Multiplex Automated Genomic Engineering (MAGE), CRISPR-enabled trackable genome engineering (CREATE), transposon based mutagenesis, genome shuffling, random recombination, non-homologous end joining, traceable multiplex recombineering (TRMR), or a CRISPR guided DNA polymerase.

Embodiment 188. The method of embodiment 187, wherein the random mutagenesis is saturation mutagenesis.

Embodiment 189. The method of embodiment 160, wherein the biological diversity is of target protein optimization.

Embodiment 190. The method of embodiment 189, wherein identifying the desirable genetic variant comprises measuring one or more characteristics of a target protein including substrate specificity, substrate state, sensitivity to divalent cation concentration, temperature tolerance, catalytic performance, resistance to protease degradation, pH tolerance, sensitivity to an inhibitor, cofactor preference, enzymatic rate, half life, activity when immobilized to a support, or a sensitivity to a gas.

Embodiment 191. The method of embodiment 190, wherein substrate state is soluble or surface adsorbed.

Embodiment 192. The method of embodiment 190, wherein the diversity screen further comprises enriching the genetic elements based on the one or more characteristics of the target protein.

Embodiment 193. The method of embodiment 160, wherein the target protein genetic elements comprise gene regions, sequence motifs, and protein structural classes.

Embodiment 194. The method of embodiment 190, wherein a gene encoding the target protein is COL1A1 (human Type 1 collagen).

Embodiment 195. The method of embodiment 190, wherein the target protein is a structural protein, an enzyme, a surface receptor protein, a peptide hormone, an immune system component, or a bioactive peptide.

Embodiment 196. The method of embodiment 190, wherein the target protein is an industrial enzyme.

Embodiment 197. The method of embodiment 190, wherein the target protein is a therapeutic protein.

Embodiment 198. The method of embodiment 195, wherein the peptide hormone is insulin or signaling factor.

Embodiment 199. The method of embodiment 195, wherein the structural protein is collagen or a food-based protein.

Embodiment 200. The method of embodiment 195, wherein the enzyme is a lipase or a poly(ethylene terephthalate) hydrolase (PETase).

Embodiment 201. The method of embodiment 160, wherein the biological diversity is of a discovery library.

Embodiment 202. The method of embodiment 201, wherein the discovery library is an environmental DNA (eDNA) library.

Embodiment 203. The method of embodiment 160, wherein the conditional diversity is of one or more fermentation conditions.

Embodiment 204. The method of embodiment 203, wherein the one or more fermentation conditions include: temperature, media, oxygenation, salinity, pH, mixing, feeding schedule, carbon source, or a change in any one or combination thereof.

Embodiment 205. The method of embodiment 203, further comprising identifying industrial fermentation conditions to produce the desirable genetic variant in a volume greater than 100 milliliters.

Embodiment 206. The method of embodiment 160, wherein the conditional diversity is of one or more application conditions.

Embodiment 207. The method of embodiment 206, wherein the application conditions include pH, temperature, substrate, reaction buffer, and attachment to a support.

Embodiment 208. The method of embodiment 160, wherein identifying the desirable genetic variant comprises sequencing.

Embodiment 209. The method of embodiment 208, wherein sequencing comprises performing PCR.

Embodiment 210. The method of embodiment 208, wherein sequencing comprises performing next-generation sequencing (NGS).

Embodiment 211. The method of embodiment 208, wherein identifying comprises identifying open reading frames that encode the desirable genetic variant.

Embodiment 212. A method for identifying a final optimized protein or a final optimized strain that meets a performance criteria comprising:
(a) obtaining a data set comprising:
i) data of a plurality of different genetic elements selected from two or more of a) different genetic variants of a strain, b) different genetic variants of a protein, or c) different genes encoding distinct proteins, and
ii) for each of the plurality of different genetic elements, data of a plurality of different conditions,
(b) integrating the data set to identify or predict a final optimized protein or a final optimized strain that meets the performance criteria or identify additional data to introduce to (a).

Embodiment 213. The method of embodiment 212, wherein the performance criteria include target protein expression level, target protein stability, target protein substrate specificity, target protein activity, strain proliferation, strain tolerance to fermentation conditions, target protein folding, target protein-to-byproduct ratio, or a target protein modification.

Embodiment 214. The method of embodiment 212, wherein the data of the plurality of conditions comprise target protein stability, strain tolerance to divalent cation concentrations, target protein substrate specificity, temperature tolerance, pH tolerance, expression level, or strain viability.

Embodiment 215. The method of embodiment 212, wherein the data set is applied to a machine learning algorithm, wherein the additional data in (b) is identified by the machine learning algorithm.

Embodiment 216. The method of embodiment 215, wherein the additional data is a library of genetic elements or additional conditions.

Embodiment 217. The method of embodiment 212, wherein the data set comprises data from one or more of a fluorogenic assay or a colorimetric assay.

Embodiment 218. The method of embodiment 217, wherein the fluorogenic assay is a direct assay, an indirect assay, a binding assay, or an in-vivo reporter assay.

Embodiment 219. The method of embodiment 212, wherein integrating the data set to identify additional data in (b) further comprises:
i) identifying an intermediate protein of interest or intermediate strain of interest that meets a subset of performance criteria,
ii) identifying an additional plurality of variants with at least 70%, 80%, or 90% homology to the intermediate protein of interest or the intermediate strain of interest as additional data to introduce to (a), and
iii) for each of the additional plurality of variants, obtaining additional data of the plurality of different conditions to introduce to (a).

Embodiment 220. The method of embodiment 219, further comprising obtaining additional data of the plurality of different conditions either a) individually when additional plurality of variants comprises less than 100 members or b) at a population level when the additional plurality of variants comprises more than 100 members.

Embodiment 221. The method of embodiment 212, wherein the genetic variants of the strain is from a library of strain genetic variants.

Embodiment 222. The method of embodiment 221, wherein the library of strain genetic variants is selected from the group consisting of a whole-genome mutagenesis library, a genome-shuffled library, a targeted genomic library, and a transposon library.

Embodiment 223. The method of embodiment 222, wherein the whole-genome mutagenesis library is a whole-genome random mutagenesis library.

Embodiment 224. The method of embodiment 222, wherein the targeted genomic library is a promoter swap library.

Embodiment 225. The method of embodiment 222, wherein the transposon library is a promoter swap library.

Embodiment 226. The method of embodiment 221, wherein the library of strain genetic variants is generated by random mutagenesis, Multiplex Automated Genomic Engineering (MAGE), or CRISPR-enabled trackable genome engineering (CREATE).

Embodiment 227. The method of embodiment 212, wherein the different genetic variants of the protein is a library of target protein-encoding genetic variants.

Embodiment 228. The method of embodiment 227, wherein the data set comprises different protein-encoding genetic variants and the additional data comprises a subsequence library of residue-encoding variants.

Embodiment 229. The method of embodiment 228, wherein the subsequence library is generated by gene shuffling.

Embodiment 230. The method of embodiment 227, wherein the library of target protein-encoding genetic variants is generated by random mutagenesis, Multiplex Automated Genomic Engineering (MAGE) or CRISPR-enabled trackable genome engineering (CREATE).

Embodiment 231. The method of embodiment 227, wherein the library of target protein-encoding genetic variants is selected from the group consisting of a single gene random mutation library, a site saturation library, a small-insert metagenomic library, and a large-insert metagenomic library.

Embodiment 232. The method of embodiment 212, wherein the different genes encoding distinct proteins is an environmental DNA (eDNA) library.

Embodiment 233. A system for processing cells comprising one or more processors and computer readable medium, the computer readable medium comprising instructions thereon that when executed by the one or more processors cause the system to:
(a) partition a population of cells into a plurality of reaction volumes to yield partitioned cells; and
(b) assay the partitioned cells for a phenotype to generate signals for the partitioned cells;
wherein a coefficient of variation (CV) among the signals for the partitioned cells is 11% or less when the population of cells is a homogenous population of cells.

Embodiment 234. The system of embodiment 233, wherein the CV is 10% or less.

Embodiment 235. The system of embodiment 233, wherein the CV is 7% or less.

Embodiment 236. The system of embodiment 233, wherein the CV is from about 5% to about 10%.

Embodiment 237. The system of embodiment 233, wherein the homogenous population of cells comprises at least 1 million cells.

Embodiment 238. The system of embodiment 233, wherein the homogenous population of cells comprises at least 10,000,000 cells.

Embodiment 239. The system of embodiment 233, wherein the reaction volumes comprise droplets.

Embodiment 240. The system of embodiment 233, wherein the assay comprises addition of a detection reagent to the partitioned cells.

Embodiment 241. The system of embodiment 240, wherein the assay comprises control of timing of the addition of the detection reagent to the partitioned cells.

Embodiment 242. The system of embodiment 240, wherein the detection reagent comprises an enzyme substrate.

Embodiment 243. The system of embodiment 233, wherein the assay comprises detection of the signals for the partitioned cells.

Embodiment 244. The system of embodiment 243, wherein the detection comprises optical detection.

Embodiment 245. The system of embodiment 243, wherein the assay comprises control of timing of detection signals for the partitioned cells.

Embodiment 246. The system of embodiment 233, wherein the phenotype comprises an enzyme activity.

Embodiment 247. The system of embodiment 233, wherein (a) comprises control of a volume size of each reaction volume of the plurality of reaction volumes.

Embodiment 248. The system of embodiment 233, wherein the homogenous population of cells comprises a same genetic material.

Embodiment 249. The system of embodiment 233, wherein the homogenous population of cells comprises a same gene of interest with a same sequence.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
(a) subjecting a first plurality of partitions comprising proteins encoded by a first library of different genetic variants to different conditions to generate
a first dataset comprising data on each protein encoded by the first library of different genetic variants in each of the different conditions;
(b) based on the first dataset, identifying one or more of the first library of different genetic variants encoding a first protein that is improved in at least one performance criteria;
(c) generating a second plurality of partitions comprising proteins encoded by a second library of different genetic variants, the proteins encoded by the second library of genetic variants having at least 70% homology to the first protein that is improved in the at least one performance criteria;
(d) subjecting the second plurality of partitions comprising proteins encoded by the second library of different genetic variants to the different conditions to generate a second dataset comprising data on each protein encoded by the second library of different genetic variants in each of the different conditions;
(e) based on the second dataset, identifying one or more of the second library of different genetic variants encoding a second protein that is improved in the at least one performance criteria compared to the first protein that is improved in the at least one performance criteria;

(f) generating a third plurality of partitions comprising proteins encoded by a third library of different genetic variants, the proteins encoded by the third library of different genetic variants having at least 70% homology to the second protein that is improved in the at least one performance criteria;

(g) subjecting the third plurality of partitions comprising proteins encoded by the third library of different genetic variants to the different conditions to generate a third dataset comprising data on each protein encoded by the third plurality of different genetic variants in each of the different conditions;

(h) using a feedback controller to (i) maintain a frequency of generation of the second plurality of partitions or third plurality of partitions or (ii) regulate a threshold gate used to select a target percentage of the first plurality of partitions in (a), the second plurality of partitions in (d), or third plurality of partitions in (g); and (i) based on the third dataset, identifying one or more of the third library of different genetic variants encoding a third protein that is improved in the at least one performance criteria compared to the second protein that is improved in the at least one performance criteria.

2. The method of claim 1, wherein the at least one performance criteria comprise a target protein expression level, a target protein stability, a target protein substrate specificity, a target protein activity, a proliferation of a target protein producing strain, a protein producing strain tolerance to fermentation conditions, target protein folding, a target protein-to-byproduct ratio, and/or a target protein modification.

3. The method of claim 1, wherein the different conditions comprise different: timing each partition of the first plurality of partitions, the second plurality of partitions, and the third plurality of partitions is subject to each condition, divalent cation concentrations, protein target substrates, temperatures, or pH.

4. The method of claim 1, wherein the first library of different genetic variants, the second library of different genetic variants, and the third library of different genetic variants each comprise at least 100 different genetic variants.

5. The method of claim 4, wherein the data in (a), (d), and (g) are acquired at a rate of at least 100 genetic variants/min.

6. The method of claim 1, wherein the first plurality of partitions comprise cells comprising the proteins encoded by the first library of different genetic variants, the second plurality of partitions comprise cells comprising the proteins encoded by the second library of different genetic variants, and the third plurality of partitions comprise cells comprising the proteins encoded by the third library of different genetic variants, and the different conditions comprise: variations in temperature, feed rate, growth or nutrition medium composition, oxygenation, salinity, pH, carbon source, carbon dioxide concentration, buffer concentration, ion concentration, duration of culture, perfusion or mixing, aeration, reaction time, metal ion concentration, additive concentration, feeding schedule, a combination thereof, or a change in any one or combination thereof.

7. The method of claim 1, wherein the third protein functions in an environment that is hypoxic, that has a temperature of about 15° C., that comprises a non-normal pH, and/or that comprises low glucose.

8. The method of claim 1, wherein each genetic variant of the first library of different genetic variants comprises a fiducial sequence.

9. The method of claim 1, further comprising generating the first library of different genetic variants using mutagens.

10. The method of claim 9, wherein the generating the second library of different genetic variants or the third library of genetic variants is performed using the mutagens.

11. The method of claim 9, wherein the mutagens comprise ultraviolet radiation, X-ray radiation, gamma-ray radiation, chemical mutagens, CRISPR-enabled trackable genome engineering, Multiplex Automated Genomic Engineering, transposon-based mutagenesis, genome shuffling, random recombination, non-homologous end joining, traceable multiplex recombineering (TRMR), or a CRISPR guided DNA polymerase.

12. The method of claim 1, wherein the first library of different genetic variants, the second library of different genetic variants, and the third library of different genetic variants each comprises at least 1,000 different genetic variants.

13. The method of claim 12, wherein the first library of different genetic variants, the second library of different genetic variants, and the third library of different genetic variants each comprises at least 1,000,000 different genetic variants.

14. The method of claim 12, further comprising performing at least 10 generations of identifying genetic variants that encode an improved protein.

15. The method of claim 14, comprising performing at least 100 generations of identifying genetic variants that encode the improved protein.

16. The method of claim 15, wherein the improved protein is an enzyme, a food protein, or a nutritional protein.

17. The method of claim 16, wherein the at least one performance criteria comprises an enzyme activity.

18. The method of claim 17, wherein the first plurality of partitions, the second plurality of partitions, and the third plurality of partitions comprise microfluidic reaction vessels.

19. The method of claim 18, further comprising applying one or more machine learning models to the first dataset to design the second plurality of genetic variants.

20. The method of claim 19, wherein the one or more machine learning models is used to predict a gene sequence, an amino acid sequence, a structural motif, and/or an enzymatic activity of the second library of genetic variants.

21. The method of claim 1, comprising using the feedback controller to maintain the frequency of generation of the second plurality of partitions and the third plurality of partitions.

22. The method of claim 21, wherein the second plurality of partitions and the third plurality of partitions comprise droplets.

23. The method of claim 22, comprising using the feedback controller to maintain the frequency of generation of the second plurality of partitions and the third plurality of partitions by automatically adjusting flow rate, pressure, or temperature.

24. The method of claim 22, comprising using the feedback controller to maintain the frequency of generation of the second plurality of partitions and the third plurality of partitions by accounting for deviations in liquid viscosity or temperature.

25. The method of claim 1, comprising using the feedback controller to regulate the threshold gate used to select a target percentage of the first plurality of partitions in (a), the second plurality of partitions in (d), or third plurality of partitions in (g).

26. The method of claim 25, comprising using the feedback controller to adjust the threshold gate to account for noise or drift.

27. The method of claim 26, comprising using the feedback controller to raise or lower the threshold gate.

28. The method of claim 1, wherein the first plurality of partitions, the second plurality of partitions, and the third plurality of partitions comprise droplets.

29. The method of claim 1, wherein the feedback controller comprises a proportional-integral-derivative (PID) algorithm.

* * * * *